(12) United States Patent
Cataldo et al.

(10) Patent No.: US 12,186,713 B2
(45) Date of Patent: Jan. 7, 2025

(54) NON-WOVEN FIBER MEMBRANES

(71) Applicants: MERCK MILLIPORE LTD., Carrigtwohill (IE); THE PROVOST FELLOWS FOUNDATION SCHOLARS AND THE OTHER MEMBERS OF BOARD OF THE COLLEGE OF THE HOLY AND UNDIVIDED TRINITY OF QUEEN ELIZABETH NEAR DUBLIN, Dublin (IE)

(72) Inventors: William Cataldo, Bradford, MA (US); Inga Elkina, Wilmington, MA (US); Kamran Beyzavi, Livingston (GB); Thomas Fitzgerald, Killarney (IE); Dennis Aquino, Chelmsford, MA (US); Daniel Callahan, Acton, MA (US); Michael Mansfield, Bedford, MA (US); Mikhail Kozlov, Lexington, MA (US); Gabriel Tkacik, Bedford, MA (US); Murugan Rajendiran, Carrigtwohill (IE); Ramesh Babu Padamati, Dublin (IE)

(73) Assignees: Merck Millipore Ltd., Carrigtwohill (IE); The Provost Fellows Foundation Scholars and the Other Members of Board of the College of the Holy Cross, Dublin (IE)

( * ) Notice: Subject to any disclaimer, the term of this patent is extended or adjusted under 35 U.S.C. 154(b) by 7 days.

(21) Appl. No.: 16/631,572

(22) PCT Filed: Jul. 20, 2018

(86) PCT No.: PCT/IB2018/000918
§ 371 (c)(1),
(2) Date: Jan. 16, 2020

(87) PCT Pub. No.: WO2019/016605
PCT Pub. Date: Jan. 24, 2019

(65) Prior Publication Data
US 2020/0173076 A1 Jun. 4, 2020

Related U.S. Application Data

(60) Provisional application No. 62/535,586, filed on Jul. 21, 2017.

(51) Int. Cl.
*B01D 71/40* (2006.01)
*B01D 39/16* (2006.01)
(Continued)

(52) U.S. Cl.
CPC ........ *B01D 71/4011* (2022.08); *B01D 69/107* (2022.08); *D01D 5/003* (2013.01);
(Continued)

(58) Field of Classification Search
CPC .......... B01D 39/1623; B01D 2239/025; B01D 2239/0631; B01D 2239/1216;
(Continued)

(56) References Cited

U.S. PATENT DOCUMENTS 500,167 A   6/1893   Surerus et al.
552,291 A   12/1895  Keefer
(Continued)

FOREIGN PATENT DOCUMENTS

CN   2390670 Y   8/2000
CN   1460534 A   12/2003
(Continued)

OTHER PUBLICATIONS

Office Action received for Japanese Patent Application No. 2020-524695 issued on Apr. 5, 2022, 09 pages (5 pages of official Copy & 4 pages of English Translation).
(Continued)

*Primary Examiner* — Arti Singh-Pandey
(74) *Attorney, Agent, or Firm* — EMD Millipore Corporation

(57) ABSTRACT

Provided herein are electrospun or electroblown non-woven fiber membranes, methods of making such membranes and lateral flow diagnostic devices comprising such membranes.

23 Claims, 75 Drawing Sheets

(51) Int. Cl.
*B01D 69/10* (2006.01)
*D01D 5/00* (2006.01)
*D04H 1/728* (2012.01)
*G01N 33/543* (2006.01)

(52) U.S. Cl.
CPC ....... *D04H 1/728* (2013.01); *G01N 33/54388* (2021.08); *B01D 39/1623* (2013.01); *B01D 2239/025* (2013.01); *B01D 2239/0631* (2013.01); *B01D 2239/1233* (2013.01); *B01D 2323/39* (2013.01)

(58) Field of Classification Search
CPC ........ B01D 2239/1233; B01D 2323/39; B01D 69/10; B01D 71/34; B01D 71/40; D04H 1/728; D04H 1/43838; D01D 5/0007; D01D 5/003; D01F 6/12; D01F 6/16; D01F 6/48; D01F 6/52
See application file for complete search history.

(56) References Cited

U.S. PATENT DOCUMENTS

| | | |
|---|---|---|
| 692,631 A | 2/1902 | Cooley |
| 705,691 A | 7/1902 | Morton |
| 1,699,615 A | 1/1929 | Kiyohiko |
| 1,975,504 A | 10/1934 | Formhals |
| 1,975,594 A | 10/1934 | Stroud et al. |
| 2,048,651 A | 7/1936 | Norton |
| 2,158,415 A | 5/1939 | Formhals |
| 2,158,416 A | 5/1939 | Formhals |
| 2,160,962 A | 6/1939 | Formhals |
| 2,168,027 A | 8/1939 | Gladding |
| 2,349,950 A | 5/1944 | Formhals |
| 3,585,126 A | 6/1971 | Cannon et al. |
| 3,620,970 A | 11/1971 | Klug et al. |
| 3,864,289 A | 2/1975 | Rendall |
| 3,876,738 A | 4/1975 | Marinaccio et al. |
| 3,994,258 A | 11/1976 | Simm |
| 4,043,331 A | 8/1977 | Martin et al. |
| 4,069,026 A | 1/1978 | Simm et al. |
| 4,127,706 A | 11/1978 | Martin et al. |
| 4,143,196 A | 3/1979 | Simm et al. |
| 4,261,834 A | 4/1981 | Dewinter |
| 4,323,525 A | 4/1982 | Bornat |
| 4,510,047 A | 4/1985 | Thompson |
| 4,604,326 A | 8/1986 | Seiichi et al. |
| 4,629,563 A | 12/1986 | Wrasidlo |
| 4,650,506 A | 3/1987 | Barris et al. |
| 4,657,793 A | 4/1987 | Fisher |
| 4,704,324 A | 11/1987 | Davis et al. |
| 4,717,498 A | 1/1988 | Maxon |
| 4,778,601 A | 10/1988 | Lopatin et al. |
| 4,824,568 A | 4/1989 | Allegrezza, Jr. et al. |
| 4,839,203 A | 6/1989 | Davis et al. |
| 4,849,127 A | 7/1989 | Maxon |
| 4,853,129 A | 8/1989 | Wan |
| 4,938,869 A | 7/1990 | Bayerlein et al. |
| 4,983,268 A | 1/1991 | Kirkpatrick et al. |
| 4,983,288 A | 1/1991 | Karbachsch et al. |
| 5,096,473 A | 3/1992 | Sassa et al. |
| 5,228,994 A | 7/1993 | Tkacik et al. |
| 5,238,106 A | 8/1993 | Nguyen et al. |
| 5,238,568 A | 8/1993 | Fely et al. |
| 5,248,424 A | 9/1993 | Cote et al. |
| 5,264,165 A | 11/1993 | Knight |
| 5,283,106 A | 2/1994 | Seiler et al. |
| 5,435,957 A | 7/1995 | Degen et al. |
| 5,500,167 A | 3/1996 | Degen |
| 5,507,847 A | 4/1996 | George et al. |
| 5,522,601 A | 6/1996 | Murphy |
| 5,522,991 A | 6/1996 | Tuccelli et al. |
| 5,536,413 A | 7/1996 | Bormann et al. |
| 5,620,790 A | 4/1997 | Holzki et al. |
| 5,652,050 A | 7/1997 | Pall et al. |
| 5,672,399 A | 9/1997 | Kahlbaugh et al. |
| 5,693,231 A | 12/1997 | Johnson et al. |
| 5,731,164 A | 3/1998 | Becker et al. |
| 5,739,316 A | 4/1998 | Beer et al. |
| 5,846,438 A | 12/1998 | Pall et al. |
| 5,968,650 A | 10/1999 | Tennent et al. |
| 5,985,112 A | 11/1999 | Fischer |
| 6,045,899 A | 4/2000 | Wang et al. |
| 6,074,869 A | 6/2000 | Pall et al. |
| 6,113,794 A | 9/2000 | Kumar et al. |
| 6,143,675 A | 11/2000 | McCollam et al. |
| 6,153,098 A | 11/2000 | Bayerlein et al. |
| 6,171,684 B1 | 1/2001 | Kahlbaugh et al. |
| 6,315,805 B1 | 11/2001 | Strauss |
| 6,321,915 B1 | 11/2001 | Wilson et al. |
| 6,464,881 B2 | 10/2002 | Thoraval |
| 6,513,666 B2 | 2/2003 | Meyering et al. |
| 6,554,881 B1 | 4/2003 | Healey |
| 6,598,749 B2 | 7/2003 | Paul et al. |
| 6,604,925 B1 | 8/2003 | Dubson |
| 6,616,435 B2 | 9/2003 | Lee et al. |
| 6,713,011 B2 | 3/2004 | Chu et al. |
| 6,743,273 B2 | 6/2004 | Chung et al. |
| 6,746,517 B2 | 6/2004 | Benson et al. |
| 6,770,204 B1 | 8/2004 | Koslow |
| 6,796,169 B2 | 9/2004 | Makino et al. |
| 6,797,169 B1 | 9/2004 | Ide et al. |
| 6,835,311 B2 | 12/2004 | Koslow |
| 6,858,057 B2 | 2/2005 | Healey |
| 6,866,704 B2 | 3/2005 | Koslow |
| 6,866,794 B1 | 3/2005 | Zhang et al. |
| 6,872,311 B2 | 3/2005 | Koslow |
| 6,913,154 B2 | 7/2005 | Koslow |
| 6,924,028 B2 | 8/2005 | Chung et al. |
| 6,953,604 B2 | 10/2005 | Koslow |
| 6,955,775 B2 | 10/2005 | Chung et al. |
| 6,959,820 B2 | 11/2005 | Koslow |
| 6,974,490 B2 | 12/2005 | Gillingham et al. |
| 6,994,811 B2 | 2/2006 | Kools |
| 6,998,058 B2 | 2/2006 | Koslow |
| 7,008,465 B2 | 3/2006 | Graham et al. |
| 7,008,537 B2 | 3/2006 | Koslow |
| 7,070,640 B2 | 7/2006 | Chung et al. |
| 7,070,836 B2 | 7/2006 | Czado |
| 7,090,712 B2 | 8/2006 | Gillingham et al. |
| 7,090,715 B2 | 8/2006 | Chung et al. |
| 7,097,694 B1 | 8/2006 | Jaroszczyk et al. |
| 7,105,228 B2 | 9/2006 | Averdung et al. |
| 7,108,791 B2 | 9/2006 | Tkacik et al. |
| 7,109,136 B2 | 9/2006 | Senecal et al. |
| 7,115,150 B2 | 10/2006 | Johnson et al. |
| 7,144,533 B2 | 12/2006 | Koslow |
| 7,179,317 B2 | 2/2007 | Chung et al. |
| 7,229,665 B2 | 6/2007 | Kools |
| 7,235,122 B2 | 6/2007 | Bryner et al. |
| 7,270,692 B2 | 9/2007 | Gillingham et al. |
| 7,270,693 B2 | 9/2007 | Chung et al. |
| 7,318,853 B2 | 1/2008 | Chung et al. |
| 7,341,663 B2 | 3/2008 | Offeman et al. |
| 7,378,020 B2 | 5/2008 | Eraci et al. |
| 7,419,601 B2 | 9/2008 | Cooper et al. |
| 7,459,085 B2 | 12/2008 | Koguma et al. |
| 7,470,639 B2 | 12/2008 | Angelini et al. |
| 7,555,195 B2 | 6/2009 | Yamashita et al. |
| 7,585,437 B2 | 9/2009 | Jirsak et al. |
| 7,743,929 B2 | 6/2010 | Kools |
| 7,789,930 B2 | 9/2010 | Ensor et al. |
| 7,790,135 B2 | 9/2010 | Lennhoff |
| 7,875,380 B2 | 1/2011 | Chun et al. |
| 7,927,885 B2 | 4/2011 | Nishita |
| 7,993,523 B2 | 8/2011 | Chen et al. |
| 7,993,567 B2 | 8/2011 | Scott-carnell et al. |
| 8,002,990 B2 | 8/2011 | Schroeder et al. |
| 8,038,013 B2 | 10/2011 | Chen et al. |
| 8,222,166 B2 | 7/2012 | Chu et al. |
| 8,282,712 B2 | 10/2012 | Chi et al. |
| 8,361,180 B2 | 1/2013 | Lim et al. |
| 8,366,797 B2 | 2/2013 | Chung et al. |
| 8,679,217 B2 | 3/2014 | Chi et al. |

(56) References Cited

U.S. PATENT DOCUMENTS

| | | |
|---|---|---|
| 8,689,985 B2 | 4/2014 | Bate et al. |
| 8,906,447 B2 | 12/2014 | Zhamu et al. |
| 9,174,152 B2 | 11/2015 | Dai et al. |
| 9,180,393 B2 | 11/2015 | Chen et al. |
| 9,272,247 B2 | 3/2016 | Qi et al. |
| 9,623,352 B2 | 4/2017 | Kas et al. |
| 9,750,829 B2 | 9/2017 | Kozlov et al. |
| 9,889,214 B2 | 2/2018 | Kozlov et al. |
| 9,943,616 B2 | 4/2018 | Kozlov et al. |
| 10,064,965 B2 | 9/2018 | Kozlov et al. |
| 10,252,199 B2 | 4/2019 | Kas et al. |
| 10,633,766 B2 | 4/2020 | Haff et al. |
| 10,675,588 B2 | 6/2020 | Cataldo et al. |
| 10,722,602 B2 | 7/2020 | Kozlov et al. |
| 11,154,821 B2 | 10/2021 | Kas et al. |
| 2002/0046656 A1 | 4/2002 | Benson et al. |
| 2002/0084178 A1 | 7/2002 | Dubson et al. |
| 2002/0096246 A1 | 7/2002 | Sennet et al. |
| 2002/0100725 A1 | 8/2002 | Lee et al. |
| 2002/0117439 A1 | 8/2002 | Paul et al. |
| 2002/0124953 A1 | 9/2002 | Sennett et al. |
| 2002/0175124 A1 | 11/2002 | Tkacik et al. |
| 2003/0010002 A1 | 1/2003 | Johnson et al. |
| 2003/0026985 A1 | 2/2003 | Greiner et al. |
| 2003/0106294 A1 | 6/2003 | Chung et al. |
| 2003/0121844 A1 | 7/2003 | Koo et al. |
| 2003/0137083 A1 | 7/2003 | Ko et al. |
| 2003/0177909 A1 | 9/2003 | Koslow |
| 2003/0213218 A1 | 11/2003 | Dubson |
| 2003/0213744 A1 | 11/2003 | Kools et al. |
| 2004/0017011 A1 | 1/2004 | Narita et al. |
| 2004/0036014 A1 | 2/2004 | Simon |
| 2004/0038013 A1 | 2/2004 | Schaefer et al. |
| 2004/0038014 A1 | 2/2004 | Schaefer et al. |
| 2004/0070118 A1 | 4/2004 | Czado |
| 2004/0080083 A1 | 4/2004 | Czado |
| 2004/0116025 A1 | 6/2004 | Gogins et al. |
| 2004/0118770 A1 | 6/2004 | Sale et al. |
| 2004/0159609 A1 | 8/2004 | Chase |
| 2004/0206693 A1 | 10/2004 | Charkoudian et al. |
| 2004/0206694 A1 | 10/2004 | Charkoudian |
| 2004/0207126 A1 | 10/2004 | Czado |
| 2004/0255783 A1 | 12/2004 | Graham et al. |
| 2005/0008707 A1 | 1/2005 | Hovey et al. |
| 2005/0026526 A1 | 2/2005 | Verdegan et al. |
| 2005/0048274 A1 | 3/2005 | Rabolt et al. |
| 2005/0051487 A1 | 3/2005 | Koslow |
| 2005/0053782 A1 | 3/2005 | Sen et al. |
| 2005/0067732 A1 | 3/2005 | Kim et al. |
| 2005/0073075 A1 | 4/2005 | Chu et al. |
| 2005/0123688 A1 | 6/2005 | Craighead et al. |
| 2005/0142973 A1 | 6/2005 | Bletsos et al. |
| 2005/0163955 A1 | 7/2005 | Schaefer et al. |
| 2005/0210844 A1 | 9/2005 | Kahlbaugh et al. |
| 2005/0235619 A1 | 10/2005 | Heinz et al. |
| 2005/0247236 A1 | 11/2005 | Frey et al. |
| 2005/0260381 A1 | 11/2005 | Ditter et al. |
| 2005/0272925 A1 | 12/2005 | Charkoudian et al. |
| 2006/0016748 A1 | 1/2006 | Koguma et al. |
| 2006/0053782 A1 | 3/2006 | Kobayashi et al. |
| 2006/0057377 A1 | 3/2006 | Harrison et al. |
| 2006/0060519 A1 | 3/2006 | Tkacik et al. |
| 2006/0068668 A1 | 3/2006 | Kameoka et al. |
| 2006/0084340 A1 | 4/2006 | Bond et al. |
| 2006/0084341 A1 | 4/2006 | Bodaghi et al. |
| 2006/0086657 A1 | 4/2006 | Kools |
| 2006/0094320 A1 | 5/2006 | Chen et al. |
| 2006/0096912 A1 | 5/2006 | Nussbaumer et al. |
| 2006/0097431 A1 | 5/2006 | Hovanec |
| 2006/0135020 A1 | 6/2006 | Weinberg et al. |
| 2006/0137317 A1 | 6/2006 | Bryner et al. |
| 2006/0137318 A1 | 6/2006 | Lim et al. |
| 2006/0138710 A1 | 6/2006 | Bryner et al. |
| 2006/0138711 A1 | 6/2006 | Bryner et al. |
| 2006/0144782 A1 | 7/2006 | Buck |
| 2006/0149561 A1 | 7/2006 | Govender |
| 2006/0151094 A1 | 7/2006 | Angelini et al. |
| 2006/0160064 A1 | 7/2006 | Carbonell |
| 2006/0213829 A1 | 9/2006 | Rutledge et al. |
| 2006/0230731 A1 | 10/2006 | Kalayci et al. |
| 2006/0242933 A1 | 11/2006 | Webb et al. |
| 2006/0246798 A1 | 11/2006 | Reneker et al. |
| 2006/0264139 A1 | 11/2006 | Czado |
| 2006/0264140 A1 | 11/2006 | Andrady et al. |
| 2006/0286446 A1 | 12/2006 | Chun et al. |
| 2006/0286886 A1 | 12/2006 | Komura et al. |
| 2006/0290031 A1 | 12/2006 | Jirsak et al. |
| 2006/0293116 A1 | 12/2006 | Hocknell et al. |
| 2006/0293169 A1 | 12/2006 | Srinivasan et al. |
| 2007/0009736 A1 | 1/2007 | Chuang et al. |
| 2007/0018361 A1 | 1/2007 | Xu |
| 2007/0021021 A1 | 1/2007 | Verdegan et al. |
| 2007/0040305 A1 | 2/2007 | Armantrout et al. |
| 2007/0042069 A1 | 2/2007 | Armantrout et al. |
| 2007/0062855 A1 | 3/2007 | Chase et al. |
| 2007/0074628 A1 | 4/2007 | Jones et al. |
| 2007/0075015 A1 | 4/2007 | Bates et al. |
| 2007/0084786 A1 | 4/2007 | Smithies |
| 2007/0107399 A1 | 5/2007 | Schwandt et al. |
| 2007/0113530 A1 | 5/2007 | Morozov et al. |
| 2007/0125700 A1 | 6/2007 | Ding et al. |
| 2007/0134151 A1 | 6/2007 | Jo et al. |
| 2007/0151921 A1 | 7/2007 | Nakano et al. |
| 2007/0163217 A1 | 7/2007 | Frey et al. |
| 2007/0175196 A1 | 8/2007 | Tepper et al. |
| 2007/0196401 A1 | 8/2007 | Naruse et al. |
| 2007/0240576 A1 | 10/2007 | von Blucher et al. |
| 2007/0298072 A1 | 12/2007 | Kitazono et al. |
| 2008/0004205 A1 | 1/2008 | Tkacik et al. |
| 2008/0004206 A1 | 1/2008 | Rosen et al. |
| 2008/0010959 A1 | 1/2008 | Gillingham et al. |
| 2008/0020192 A1 | 1/2008 | Yen et al. |
| 2008/0022024 A1 | 1/2008 | Mao |
| 2008/0026041 A1 | 1/2008 | Tepper et al. |
| 2008/0034967 A1 | 2/2008 | Ping |
| 2008/0060328 A1 | 3/2008 | Devine |
| 2008/0070463 A1 | 3/2008 | Arora et al. |
| 2008/0073296 A1 | 3/2008 | Dema et al. |
| 2008/0099398 A1 | 5/2008 | Hu et al. |
| 2008/0110342 A1 | 5/2008 | Ensor et al. |
| 2008/0110822 A1 | 5/2008 | Chung et al. |
| 2008/0134652 A1 | 6/2008 | Lim et al. |
| 2008/0136063 A1 | 6/2008 | Chuang et al. |
| 2008/0149561 A1 | 6/2008 | Chu et al. |
| 2008/0150192 A1 | 6/2008 | Perret et al. |
| 2008/0150197 A1 | 6/2008 | Chang et al. |
| 2008/0164214 A1 | 7/2008 | Emner et al. |
| 2008/0207076 A1 | 8/2008 | Jirsak et al. |
| 2008/0213574 A1 | 9/2008 | Mckee et al. |
| 2008/0217239 A1 | 9/2008 | Chen et al. |
| 2008/0217241 A1 | 9/2008 | Smithies et al. |
| 2008/0217807 A1 | 9/2008 | Lee et al. |
| 2008/0220241 A1 | 9/2008 | Abdelsalam et al. |
| 2008/0237934 A1 | 10/2008 | Reneker et al. |
| 2008/0242171 A1 | 10/2008 | Huang et al. |
| 2008/0264258 A1 | 10/2008 | Mares et al. |
| 2008/0264259 A1 | 10/2008 | Leung |
| 2008/0274312 A1 | 11/2008 | Schelling et al. |
| 2008/0284050 A1 | 11/2008 | Mares et al. |
| 2008/0302074 A1 | 12/2008 | Gebert et al. |
| 2009/0026137 A1 | 1/2009 | Chen et al. |
| 2009/0065436 A1 | 3/2009 | Kalayci et al. |
| 2009/0091065 A1 | 4/2009 | Katti et al. |
| 2009/0110873 A1 | 4/2009 | Jiang et al. |
| 2009/0199717 A1 | 8/2009 | Green et al. |
| 2009/0220241 A1 | 9/2009 | Katagiri et al. |
| 2010/0037576 A1 | 2/2010 | Claasen et al. |
| 2010/0096066 A1 | 4/2010 | Ramaswamy et al. |
| 2010/0139224 A1 | 6/2010 | Lim et al. |
| 2010/0173070 A1 | 7/2010 | Niu |
| 2010/0193428 A1 | 8/2010 | Hane et al. |
| 2010/0206803 A1 | 8/2010 | Ward et al. |
| 2010/0222771 A1 | 9/2010 | Mitchell et al. |

(56) References Cited

U.S. PATENT DOCUMENTS

| | | | |
|---|---|---|---|
| 2010/0226823 A1* | 9/2010 | Rakhman | B01D 69/04 264/129 |
| 2010/0316988 A1 | 12/2010 | Sehgal | |
| 2011/0124941 A1 | 5/2011 | Verdegan et al. | |
| 2011/0163035 A1 | 7/2011 | Cheng et al. | |
| 2011/0168647 A1 | 7/2011 | Wieczorek et al. | |
| 2011/0198282 A1 | 8/2011 | Chu et al. | |
| 2011/0206973 A1 | 8/2011 | Brant et al. | |
| 2011/0233152 A1 | 9/2011 | Wieczorek et al. | |
| 2011/0240550 A1 | 10/2011 | Moore et al. | |
| 2011/0266213 A1 | 11/2011 | Jo et al. | |
| 2011/0305872 A1 | 12/2011 | Li et al. | |
| 2012/0061314 A1 | 3/2012 | Choi et al. | |
| 2012/0061332 A1 | 3/2012 | Kas et al. | |
| 2012/0091072 A1 | 4/2012 | Kozlov et al. | |
| 2012/0125847 A1 | 5/2012 | Sehgal | |
| 2012/0125866 A1 | 5/2012 | Fantini | |
| 2012/0318752 A1 | 12/2012 | Velu et al. | |
| 2013/0092622 A1 | 4/2013 | Kas et al. | |
| 2014/0061114 A1 | 3/2014 | Ramire | |
| 2014/0116945 A1 | 5/2014 | Kas et al. | |
| 2014/0227602 A1 | 8/2014 | Sumida et al. | |
| 2014/0284264 A1 | 9/2014 | Klein et al. | |
| 2015/0037055 A1 | 2/2015 | Kitagawa et al. | |
| 2015/0136693 A1 | 5/2015 | Hwang et al. | |
| 2015/0298070 A1 | 10/2015 | Koslov et al. | |
| 2015/0360157 A1 | 12/2015 | Hwang et al. | |
| 2016/0016124 A1 | 1/2016 | Zheng et al. | |
| 2016/0113340 A1 | 4/2016 | Levit et al. | |
| 2016/0136558 A1 | 5/2016 | Zheng et al. | |
| 2016/0136584 A1 | 5/2016 | Hwang et al. | |
| 2016/0166961 A1 | 6/2016 | Haberkamp et al. | |
| 2016/0175748 A1 | 6/2016 | Park | |
| 2016/0193555 A1 | 7/2016 | Park | |
| 2016/0243478 A1 | 8/2016 | Park | |
| 2016/0361270 A1 | 12/2016 | Stoddard et al. | |
| 2017/0100912 A1 | 4/2017 | Tricoli et al. | |
| 2017/0173509 A1 | 6/2017 | Giglia et al. | |
| 2017/0173511 A1 | 6/2017 | Kas et al. | |
| 2017/0260652 A1 | 9/2017 | Kinoshita | |
| 2017/0360969 A1 | 12/2017 | Kozlov et al. | |
| 2018/0025842 A1 | 1/2018 | Muraoka et al. | |
| 2018/0085710 A1 | 3/2018 | Cataldo et al. | |
| 2018/0142379 A1 | 5/2018 | Poss et al. | |
| 2018/0159139 A1 | 6/2018 | Radacsi et al. | |
| 2019/0015533 A1 | 1/2019 | Kozlov et al. | |
| 2019/0292686 A1 | 9/2019 | Kimiya et al. | |
| 2019/0314746 A1 | 10/2019 | Leung | |
| 2020/0173076 A1 | 6/2020 | Cataldo et al. | |
| 2021/0180255 A1 | 6/2021 | Huang et al. | |
| 2021/0355606 A1 | 11/2021 | Kas et al. | |
| 2021/0403971 A1 | 12/2021 | Hira et al. | |
| 2022/0018039 A1 | 1/2022 | Siheng et al. | |
| 2022/0168705 A1 | 6/2022 | Wong et al. | |
| 2022/0169779 A1 | 6/2022 | Noda et al. | |
| 2022/0243363 A1 | 8/2022 | Wong | |
| 2022/0281208 A1 | 9/2022 | Leung et al. | |
| 2022/0403097 A1 | 12/2022 | Noda et al. | |

FOREIGN PATENT DOCUMENTS

| | | |
|---|---|---|
| CN | 1471421 A | 1/2004 |
| CN | 1625429 A | 6/2005 |
| CN | 1625434 A | 6/2005 |
| CN | 1942616 A | 4/2007 |
| CN | 101189368 A | 5/2008 |
| CN | 101272840 A | 9/2008 |
| CN | 101318090 A | 12/2008 |
| CN | 101534954 A | 9/2009 |
| CN | 101653676 A | 2/2010 |
| CN | 102170950 A | 8/2011 |
| CN | 102227247 A | 10/2011 |
| CN | 102917777 A | 2/2013 |
| CN | 103459006 A | 12/2013 |
| CN | 104540531 A | 4/2015 |
| CN | 104906871 A | 9/2015 |
| CN | 105120991 A | 12/2015 |
| CN | 105377433 A | 3/2016 |
| CN | 106457079 A | 2/2017 |
| CN | 103972452 B | 3/2017 |
| CN | 106480517 A | 3/2017 |
| DE | 19545701 C1 | 5/1997 |
| EP | 0257635 A2 | 3/1988 |
| EP | 0320033 A1 | 6/1989 |
| EP | 0497594 A1 | 8/1992 |
| EP | 168783 B1 | 6/1994 |
| EP | 0781600 A2 | 7/1997 |
| EP | 1743975 A1 | 1/2007 |
| EP | 1745808 A1 | 1/2007 |
| EP | 1829603 A1 | 9/2007 |
| EP | 1878482 A1 | 1/2008 |
| EP | 1673493 B1 | 7/2009 |
| EP | 2174703 A1 | 4/2010 |
| EP | 2323174 A2 | 5/2011 |
| EP | 2599908 A1 | 6/2013 |
| EP | 2222385 B1 | 6/2016 |
| EP | 3279373 A1 | 2/2018 |
| GB | 1519070 A | 7/1978 |
| JP | S62-181797 A | 8/1987 |
| JP | 2-161954 A | 6/1990 |
| JP | 4-351645 A | 12/1992 |
| JP | 7-213876 A | 8/1995 |
| JP | 2000-61277 A | 2/2000 |
| JP | 2000-325764 A | 11/2000 |
| JP | 2004-028875 A | 1/2004 |
| JP | 2005-065647 A | 3/2005 |
| JP | 2005-515880 A | 6/2005 |
| JP | 2005-270965 A | 10/2005 |
| JP | 2005-333886 A | 12/2005 |
| JP | 2005-536347 A | 12/2005 |
| JP | 2006-82006 A | 3/2006 |
| JP | 2006-326579 A | 7/2006 |
| JP | 2006-299459 A | 11/2006 |
| JP | 2006-328562 A | 12/2006 |
| JP | 2006-336173 A | 12/2006 |
| JP | 2006-341233 A | 12/2006 |
| JP | 2006-527911 A | 12/2006 |
| JP | 2007-075739 A | 3/2007 |
| JP | 2007-105724 A | 4/2007 |
| JP | 2007-301436 A | 11/2007 |
| JP | 2007-332342 A | 12/2007 |
| JP | 2008-502920 A | 1/2008 |
| JP | 2008-049239 A | 3/2008 |
| JP | 2008-162098 A | 7/2008 |
| JP | 2008-525195 A | 7/2008 |
| JP | 2008-190055 A | 8/2008 |
| JP | 2009-050851 A | 3/2009 |
| JP | 2009-509754 A | 3/2009 |
| JP | 2009-127150 A | 6/2009 |
| JP | 2009-148746 A | 7/2009 |
| JP | 2009-148748 A | 7/2009 |
| JP | 2009-183879 A | 8/2009 |
| JP | 2009-233550 A | 10/2009 |
| JP | 2010-094962 A | 4/2010 |
| JP | 2011-122258 A | 6/2011 |
| JP | 2011-214168 A | 10/2011 |
| JP | 2011-529778 A | 12/2011 |
| JP | 2012-501518 A | 1/2012 |
| JP | 2012-520761 A | 9/2012 |
| JP | 2012-189355 A | 10/2012 |
| JP | 2012-523320 A | 10/2012 |
| JP | 2013-073618 A | 4/2013 |
| JP | 53-55828 B1 | 9/2013 |
| JP | 2014-504951 A | 2/2014 |
| JP | 2014-514958 A | 6/2014 |
| JP | 2014-208342 A | 11/2014 |
| JP | 2015-045114 A | 3/2015 |
| JP | 2015-183334 A | 10/2015 |
| JP | 59-31118 B2 | 5/2016 |
| JP | 2016-164319 A | 9/2016 |
| JP | 2017-506339 A | 3/2017 |
| JP | 2017-113884 A | 6/2017 |
| JP | 68-32889 B2 | 2/2021 |

(56) References Cited

FOREIGN PATENT DOCUMENTS

| | | |
|---|---|---|
| KR | 2002-0012674 A | 2/2002 |
| KR | 10-2005-0077304 A | 2/2005 |
| KR | 10-2005-0037906 A | 4/2005 |
| KR | 2005-0077304 A | 8/2005 |
| KR | 1020060079211 A | 7/2006 |
| KR | 2007-0073851 A | 7/2007 |
| KR | 10-0871440 B1 | 12/2008 |
| KR | 10-2010-0023152 A | 3/2010 |
| KR | 10-2010-0037055 A | 4/2010 |
| SG | 185659 A1 | 12/2012 |
| WO | 97/20622 A1 | 6/1997 |
| WO | 97/42835 A1 | 11/1997 |
| WO | 99/16810 A1 | 4/1999 |
| WO | 00/05358 A1 | 2/2000 |
| WO | 00/45933 A1 | 8/2000 |
| WO | 00/56804 A1 | 9/2000 |
| WO | 00/58388 A1 | 10/2000 |
| WO | 01/01047 A1 | 1/2001 |
| WO | 01/07599 A1 | 2/2001 |
| WO | 01/14047 A1 | 3/2001 |
| WO | 03/016601 A1 | 2/2003 |
| WO | 03/37959 A1 | 5/2003 |
| WO | 03/064013 A1 | 8/2003 |
| WO | 03/080905 A1 | 10/2003 |
| WO | 2004/018079 A2 | 3/2004 |
| WO | 2004/112183 A1 | 12/2004 |
| WO | 2005/024101 A1 | 3/2005 |
| WO | 2005/073441 A1 | 8/2005 |
| WO | 2005/123952 A2 | 12/2005 |
| WO | 2006/016800 A1 | 2/2006 |
| WO | 2006/068100 A1 | 6/2006 |
| WO | 2006/131061 A1 | 12/2006 |
| WO | 2006/131081 A1 | 12/2006 |
| WO | 2007/001405 A2 | 1/2007 |
| WO | 2007/011477 A2 | 1/2007 |
| WO | 2007/041311 A2 | 4/2007 |
| WO | 2007/054039 A1 | 5/2007 |
| WO | 2007/054040 A2 | 5/2007 |
| WO | 2007/054050 A1 | 5/2007 |
| WO | 2007/054054 A3 | 8/2007 |
| WO | 2007/098889 A1 | 9/2007 |
| WO | 2007/111477 A1 | 10/2007 |
| WO | 2007/137530 A2 | 12/2007 |
| WO | 2007/144189 A2 | 12/2007 |
| WO | 2008/034190 A1 | 3/2008 |
| WO | 2008/073507 A2 | 6/2008 |
| WO | 2008/106803 A1 | 9/2008 |
| WO | 2008/106903 A2 | 9/2008 |
| WO | 2008/109117 A1 | 9/2008 |
| WO | 2008/142023 A2 | 11/2008 |
| WO | 2009/010020 A2 | 1/2009 |
| WO | 2009/017086 A1 | 2/2009 |
| WO | 2009/032040 A1 | 3/2009 |
| WO | 2009/063067 A2 | 5/2009 |
| WO | 2009/064757 A1 | 5/2009 |
| WO | 2009/064767 A2 | 5/2009 |
| WO | 2009/071909 A1 | 6/2009 |
| WO | 2009/119638 A1 | 10/2009 |
| WO | 2009/140385 A1 | 11/2009 |
| WO | 2010/042647 A2 | 4/2010 |
| WO | 2010/042706 A1 | 4/2010 |
| WO | 2010/049535 A1 | 5/2010 |
| WO | 2010/069296 A1 | 6/2010 |
| WO | 2010/107503 A1 | 9/2010 |
| WO | 2010/120668 A1 | 10/2010 |
| WO | 2010/127634 A1 | 11/2010 |
| WO | 2011/019686 A1 | 2/2011 |
| WO | 2011/151314 A1 | 12/2011 |
| WO | 2012/021208 A2 | 2/2012 |
| WO | 2012/021308 A2 | 2/2012 |
| WO | 2012/088205 A1 | 6/2012 |
| WO | 2012/135679 A2 | 10/2012 |
| WO | 2012/135679 A9 | 1/2013 |
| WO | 2013/013241 A2 | 1/2013 |
| WO | 2014/093345 A1 | 6/2014 |
| WO | 2014159124 A1 | 10/2014 |
| WO | 2014/184151 A1 | 11/2014 |
| WO | 2015/091181 A2 | 6/2015 |
| WO | 2015/123154 A1 | 8/2015 |
| WO | 2015200239 A1 | 12/2015 |
| WO | 2016/158967 A1 | 10/2016 |
| WO | 2016/194707 A1 | 12/2016 |
| WO | 2017/060476 A1 | 4/2017 |

OTHER PUBLICATIONS

Reis, et al., "Membrane Separations in Biotechnology", Current Opinion in Biotechnology 2001, pp. 208-211.
Wang, et al., "Electrospun Nanofibrous Membranes for High Flux Microfiltration", Journal of Membrane Science, vol. 392-393, Mar. 1, 2012, pp. 167-174.
Yarin, et al., "Upward Needleless Electrospinning of Multiple Nanofibers", Polymer, vol. 45, Issue 9, Apr. 2004, pp. 2977-2980.
Yoon, "High Flux Ultrafiltration Membranes based on Electrospun Nanofibrous PAN Scaffolds and Chitosan Coating", Polymer, vol. 47, Issue 7, Mar. 22, 2006, pp. 2434-2441.
Yoshimatsu, et al., "Selective Molecular Adsorption using Electrospun Nanofiber Affinity membranes", Biosensors and Bioelectronics, vol. 23, Feb. 28, 2008, pp. 1208-1215.
Yun, et al., "Nanoparticle Filtration by Electrospun Polymer Fibers", Chemical Engineering Science, vol. 62, Issue 17, Jun. 16, 2007, pp. 4751-4759.
Zeman, et al., "Steric Rejection of Polymeric Solutes by Membranes with Uniform Pore Size Distribution", Separation Science and Technology, vol. 16, No. 3, Apr. 1981, pp. 275-290.
Zhao, et al., "Preparation and Properties of Electrospun Poly (Vinylidene Fluoride) Membranes", Journal of Applied Polymer Science, vol. 97, Apr. 2005, pp. 466-474.
Zwijnenberg, et al., "Acetone-Stable Nanofiltration Membranes in Deacidifying Vegetable Oil", Journal of the American Oil Chemists' Society, vol. 76, No. 1, 1999, pp. 83-87.
Gopal, et al., "Electrospun Nanofibrous Polysulfone Membranes as pre-filters: Particulate removal", Journal of Membrane Science, vol. 289, 2007, pp. 210-219.
Granath, et al., "Molecular Weight Distribution Analysis by Gel Chromatography on Sephadex", Journal of Chromatography A, vol. 28, 1967, pp. 69-81.
Grzenia, et al., "Tangential flow filtration for virus purification", Journal of Membrane Science 321, 2008, 373-380., 2008, pp. 373-380.
Guo, et al., "Cellulose Membrane used as Stationary Phase of Membrane Affinity Chromatography", Chinese Chemical Letters, vol. 5, No. 10, 1994, pp. 869-872.
Hou, et al., "Poly (p-xylylene) Nanotubes by Coating and Removal of Ultrathin Polymer Template Fibers", Macromolecules, vol. 35, 2002, pp. 2429-2431.
Huang, et al., "A review on polymer nanofibers by electro-spinning applications in nanocomposites", Composites Sci. Tech., 2003, vol. 63, pp. 2223-2253.
Huang, et al., "Electrospun Polymer Nanofibres with Small Diameters", Nanotechnology, vol. 17, No. 6, Feb. 21, 2006, pp. 1558-1563.
Jiang, et al., "Professional Knowledge of Traditional Chinese Pharmacology", Jun. 2007, 233 pages.
Kim, et al., "Characterization and Properties of P(VdF-HFP)Based Fibrous Polymer Electrolyte Membrane Prepared by Electrospinning", Journal of The Electrochemical Society, vol. 152, No. 2, Jan. 2005, pp. A295-A300.
Lev, et al., "Water Filtration by Nanotextiles", Oct. 14, 2010, 6 pages.
Levit, et al., "Supercritical CO2-Assisted Electrospinning", The Journal of Supercritical Fluids, vol. 31, Issue 3, Nov. 2004, pp. 329-333.
Li, et al., "Collecting Electrospun Nanofibers with Patterned Electrodes", Nano Letters, vol. 5, No. 5, 2005, pp. 913-916.
Lin, et al., "Preparation of Poly(ether sulfone) Nanofibers by Gas-Jet/Electrospinning", Journal of Applied Polymer Science, vol. 107, 2008, pp. 909-917.

(56) References Cited

OTHER PUBLICATIONS

Lyons, et al., "Melt Electrospinning of Polymers: A Review", Polymer News, vol. 30, No. 6, 2005, pp. 170-178.
Ma, et al., "Electrospun Cellulose Nanofiber as Affinity Membrane", Journal of Membrane Science, vol. 265, Issues 1-2, Nov. 15, 2005, pp. 115-123.
Ma, et al., "Surface Modified Nonwoven Polysulphone (PSU) Fiber Mesh by Electrospinning: A Novel Affinity Membrane", Journal of Membrane Science, vol. 272, Issues 1-2, Mar. 15, 2006, pp. 179-187.
Ma, et al., "Ultra-Fine Cellulose Nanofibers: New Nano-Scale Materials for Water Purification", Journal of Materials Chemistry, May 2011, 21(21):7507-7510.
Meltzer, "In Filtration in the Pharmaceutical Industry", Marcel Dekker: New York, 1987, pp. 103.
Mohammadzadehmoghadam, et al., "Electrospinning: Current Status and Future Trends", Nano-size polymers, 2016, pp. 89-154.
Na, et al., "Effect of Hot-Press on Electrospun Poly(vinylidene fluoride) Membranes", Polymer Engineering & Science, vol. 48, No. 5, May 2008, pp. 934-940.
International Preliminary Report on Patentability received for PCT Application No. PCT/ US2013/074132, mailed on Jun. 25, 2015, 5 pages.
International Preliminary Report on Patentability received for PCT Application No. PCT/US2010/000826 mailed on Sep. 29, 2011, 9 pages.
International Search Report received for PCT Application No. PCT/US2010/000826 mailed on Aug. 16, 2010, 12 pages.
International Preliminary Report on Patentability for PCT Application No. PCT/US2011/045805 mailed on Feb. 7, 2013, 7 pages.
International Preliminary Report on Patentability received for PCT Patent Application No. PCT/US2011/045905, mailed on Feb. 21, 2013, 7 pages.
International Search Report and Written Opinion received for PCT patent Application No. PCT/US2011/045905, mailed on Mar. 19, 2012, 13 pages.
International Preliminary Report on Patentability received for PCT Patent Application No. PCT/US2012/031549, mailed on Oct. 10, 2013, 10 pages.
International Search Report and Written Opinion received for PCT Patent Application No. PCT/US2012/031549, mailed on Nov. 28, 2012, 15 pages.
International Search Report and Written Opinion received for PCT Application No. PCT/US2012/047665 mailed on Jan. 10, 2012, 8 pages.
International Preliminary Report on Patentability for PCT Application No. PCT/US2012/047865, mailed on Jan. 21, 2014, 10 pages.
International Search Report and Written Opinion received for PCT Patent Application No. PCT/US2012/047865, mailed on Feb. 26, 2013, 18 pages.
International Search Report received for PCT Application No. PCT/US2013/074132, mailed on Mar. 21, 2014, 3 pages.
International Preliminary Report on Patentability for PCT Application No. PCT/US2015/037055 mailed on Jan. 5, 2017, 7 pages.
International Search Report and Written Opinion Received for PCT Application No. PCT/US2015/037055, mailed on Sep. 15, 2015, 7 pages.
International Search Report and Written Opinion Received for PCT Application No. PCT/US2016/018146, mailed on Jun. 7, 2016, 11 pages.
Raghavan, et al., "Novel electrospun poly(vinylidene fluoride-co-hexafluoropropylene)—in situ SiO2 composite membrane-based polymer electrolyte for lithium batteries", Journal of Power Sources, vol. 184, Issue 2, Oct. 1, 2008, pp. 437-443.
Roche, et al., "Methods Used to Validate Microporous Membranes for the Removal of Mycoplasma.", BioPharm ,, Apr. 1992, vol. 5, Issue 3, pp. 22-23.
Rutledge, et al., "Formation of Fibers by Electrospinning", Advanced Drug Delivery Reviews, vol. 59, Issue 14, Dec. 10, 2007, pp. 1384-1391.
Sajid, "Designs, formats and applications of lateral flow assay: A literature review", Journal of Saudi Chemical Society, Sep. 16, 2014, vol. 19, pp. 689-705.
Sang, et al., "Filtration by a novel nanofiber membrane and alumina adsorption to remove copper(II) from groundwater", Journal of Hazardous Materials, vol. 153, Issues 1-2, May 1, 2008, pp. 860-866.
Sang, et al., "Heavy Metal-Contaminated Groundwater Treatment by a Novel Nanofiber Membrane", Desalination, vol. 223, Issues 1-3, Mar. 1, 2008, pp. 349-360.
Schwartz, "Diafiltration for Desalting or Buffer Exchange", BioProcess International, May 2003, pp. 43-49.
Segers, et al., "Classification of Pseudomonas diminuta Leifson and Hugh 1954 and Pseudomonas vesicularis Busing, Doll, and Freytag 1953 in Brevundimonas gen. nov. as Brevundimonas diminuta comb. nov. and Brevundimonas vesicularis comb. nov., Respectively", International Journal of Systematic BActeriology, vol. 44, No. 3, Jul. 1994, pp. 499-510.
Sill, et al., "Electrospinning: Applications in Drug Delivery and Tissue Engineering", Biomaterials, vol. 29, Issue 13, May 2008, pp. 1989-2006.
Smit, et al., "Continuous Yarns from Electrospun Fibers", Polymer, vol. 46, Issue 8, Mar. 29, 2005, pp. 2419-2423.
Sterlitech Corporation, "What is Cross Flow Velocity? | Environmental XPRT", Available online at https://www.environmental-expert.com/articles/what-is-cross-flow-velocity-703133. Obtained online Aug. 29, 2019., May 26, 2017, 5 pages.
Strathmann, "Preparation of Microporous Membranes by Phase Inversion Processes", Membranes and Membrane Processes, 1986, pp. 115-135.
Tan, et al., "Systematic Parameter Study for Ultra-Fine Fiber Fabrication via Electrospinning Process", Polymer, vol. 46, Issue 16, Jul. 25, 2005, pp. 6128-6134.
Tang, et al., "Design and Fabrication of Electrospun Polyethersulfone Nanofibrous Scaffold for High-flux Nanofiltration Membranes", Journal of Polymer Science, vol. 47, Aug. 16, 2009, pp. 2288-2300.
Teo, et al., "A Review on Electrospinning Design and Nanofibre Assemblies", Nanotechnology, vol. 17, No. 14, Jun. 30, 2006, pp. R89-R106.
Extended European Search Report issued in European Application No. 12814718.8, mailed on Feb. 20, 2015, 8 pages.
Extended European Search Report received for European Patent Application No. 12765651.0, mailed on Oct. 16, 2014, 9 pages.
ASTM International, "Standard Test Method for Determining Bacterial Retention of Membrane Filters Utilized for Liquid Filtration", Designation: F838-15a, 2015, 6 pages.
ASTM International, "Standard Test Method for Determining Bacterial Retention of Membrane Filters Utilized for Liquid Filtration", ASTM F838-05, 2005, 6 pages.
Jung et al., "Detection and Treatment of Mycoplasma Contamination in Cultured Cells", Chang Gung Medical Journal, vol. 26, No. 4, Apr. 2003, pp. 250-258.
Ladewig et al., "Fundamentals of Membrane Processes", Chapter 2, Fundamentals of Membrane Bioreactors, Springer, Singapore, 2017, pp. 13-37.
Wisher Martin, "Biosafety and Product Release Testing Issues Relevant to Replication-Competent Oncolytic Viruses", Cancer Gene Therapy, vol. 9, Sep. 12, 2002, pp. 1056-1061.
Reinholt et al., "Developing New Materials for Paper-based Diagnostics using Electrospun Nanofibers", Analytical and Bioanalytical Chemistry, vol. 406, No. 14, Sep. 26, 2013, pp. 3297-3304.
Office Action received for Chinese Patent Application No. 202110189947.1 mailed on Feb. 16, 2022, 10 Pages. (4 pages of english translation & 6 pages of Official Copy).
ASTM E1294-89 Withdrawal Notice, 2008, 1 page.
ASTM International, Designation: F838-83, "Standard Test Method for Determining Bacterial Retention of Membrane Filters Utilized for Liquid Filtration," pp. 1-9, 2005, 8 pages.
ATCC 19146 Product Data Sheet, Brevundimonas diminuta, pp. 1-2.
Office Action received for Japanese Patent Application No. 2014-502850, mailed on Apr. 11, 2016.

(56) References Cited

OTHER PUBLICATIONS

Restriction Requirement received for U.S. Appl. No. 13/194,227, mailed on Jul. 31, 2013, 10 pages.
Extended European Search Report received for EP patent Application No. 07114167.5, mailed on Nov. 6, 2007, 7 pages.
Extended European Search Report received for EP Patent Application No. 10181774.0, mailed on Nov. 25, 2010, 5 pages.
Office Action received for Korean Patent Application No. 10-2013-7031748, mailed on Mar. 28, 2016, 15 pages.
Final Office Action received for U.S. Appl. No. 13/194,227, mailed on Aug. 21, 2014, 9 pages.
Final Office Action received for U.S. Appl. No. 13/194,227, mailed on Sep. 1, 2015, 8 pages.
Non Final Office Action received for U.S. Appl. No. 13/194,227, mailed on Jun. 14, 2016, 8 pages.
Non Final Office Action received for U.S. Appl. No. 13/194,227, mailed on Mar. 3, 2015, 7 pages.
Non Final Office Action received for U.S. Appl. No. 13/194,227, mailed on Oct. 31, 2013, 8 pages.
Final Office Action received for U.S. Appl. No. 13/257,501, mailed on Aug. 7, 2014, 23 pages.
Final Office Action received for U.S. Appl. No. 13/257,501, mailed on Jul. 11, 2016, 28 pages.
Non Final Office Action received for U.S. Appl. No. 13/257,501, mailed on Sep. 30, 2015, 27 pages.
Non Final Office Action received for U.S. Appl. No. 13/257,501, mailed on Dec. 13, 2013, 21 pages.
Final Office Action received for U.S. Appl. No. 13/436,043, mailed on Apr. 30, 2014, 15 pages.
Final Office Action received for U.S. Appl. No. 13/436,043, mailed on Oct. 14, 2015, 15 pages.
Non Final Office Action received for U.S. Appl. No. 13/436,043, mailed on Mar. 24, 2015, 15 pages.
Non Final Office Action received for U.S. Appl. No. 13/436,043, mailed on Oct. 23, 2013, 16 pages.
Supplementary Search Report received for European Patent Application No. 13863417.5, mailed on Jul. 20, 2016, 8 pages.
Non Final Office Action received for U.S. Appl. No. 14/118,490, mailed on Apr. 12, 2016, 17 pages.
Extended Search Report received for European Patent Application No. 17195327.6, mailed on Aug. 16, 2018, 10 pages.
Office Action received for Japanese Patent Application No. 2013-524096, mailed on Mar. 18, 2014.
Office Action received for Chinese Patent Application No. 201380070873.3, mailed on Feb. 29, 2016.
Office Action received for Japanese Patent Application No. 2014-521858, Apr. 7, 2015.
Office Action received for Japanese Patent Application No. 2015-545930, mailed on Jun. 7, 2016, 7 pages.
Aranha, Hazel, "Ensuring Safety of Biopharmaceuticals: Virus and Prion Safety Considerations", Chapter 20, Edited by Meltzer et al., Filtration and Purification in the Biopharmaceutical Industry, 2nd edition, Informa Healthcare USA, Inc.,, 2008, pp. 543-577.
ASTM International, "Standard Method for Thickness of Textile Materials", Designation: D 1777-64, Reapproved 1975, pp. 477-478.
ASTM International, "Standard Test Method for Pore Size Characteristics of Membrane Filters using Automated Liquid Porosimeter", E 1294-89, Reapproved 1999, 2 pages., Reapproved 1999, 2 pages.
ASTM International, "Standard Test Method for Thickness of Textile Materials", ASTM D1777-96 (Reapproved 2015), Sep. 2015, 5 pages.
ASTM International, "Standard Test Methods for Pore Size Characteristics of Membrane Filters by Bubble Point and Mean Flow Pore Test", ASTM International, Designation: F316-03 (Reapproved 2011), 2011, 7 pages.
ASTM International, "Standard Test Methods for Pore Size Characteristics of Membrane Filters by Bubble Point and Mean Flow Pore Test1", Designation: F316-03, 2003, pp. 1-7.
Aussawasathien, et al., "Separation of micron to sub-micron particles from water: Electrospun nylon-6 nanofibrous membranes as pre-filters", Journal of Membrane Science, vol. 315, 2008, pp. 11-19.
Barhate, et al., "Nanofibrous Filtering Media: Filtration Problems and Solutions from Tiny Materials", Journal of Membrane Science, vol. 296, Issues 1-2, Jun. 15, 2007, pp. 1-8.
Barhate, et al., "Preparation and Characterization of Nanofibrous Filtering Media", Journal of Membrane Science, vol. 283, Issues 1-2, Oct. 20, 2006, pp. 209-218.
Bhanushali, et al., "Advances in Solvent-Resistant Nanofiltration Membranes: Experimental Observations and Applications", Annals of the New York Academy of Sciences, vol. 984, Mar. 2003, pp. 159-177.
Bjorge, et al., "Performance assessment of electrospun nanofibers for filter applications", Desalination, doi:10.1016/i.desal.2009.06.064, 2009, 7 pages.
Blackwell, "Mycoplasma—Recent Developments in Detecting and in Preventing Bioreactor Contamination", BioProcess Technology Consultants, Inc., ISPE Annual Meeting Scottsdale, Arizona, Nov. 6-10, 2005, 38 pages.
Blanchard, "Quantifying Sterilizing Membrane Retention Performance", BioProcess International, vol. 5, No. 5, May 2007, 6 pages.
Blond, et al., "Strong, Tough, Electrospun Polymer-Nanotube Composite Membranes with Extremely Low Density", Advanced Functional Materials, vol. 18, Issue 17, Sep. 10, 2008, pp. 2618-2624.
Database WPI, "Week 200935", Thomson Scientific London, GB, 2009-F08014; XP002726900, 2 pages.
Deitzel, et al., "The Effect of Processing Variables on the Morphology of Electrospun Nanofibers and Textiles", Polymer, vol. 42, Issue 1, Jan. 2001, pp. 261-272.
Dimmock, et al., "Introduction to Modern Virology", Blackwell Publishing Limited, Appendixes: Survey of Virus Properties, Viruses with ssDNA genomes (class 2), 2007, p. 450.
Doshi, et al., "Electrospinning Process and Applications of Electrospun Fibers", Journal of Electrostatics, vol. 35, Issues 2-3, Aug. 1995, pp. 151-160.
Duan, et al., "Preparing Graphitic Nanoribbons from Ultrathin Electrospun Poly( methyl methacrylate) Nanofibers by Electron Beam Irradiation", 2nd IEEE International Nanoelectronics Conference (INEC 2008), Mar. 24-27, 2008, pp. 33-38.
Ebert, et al., "Solvent Resistant Nanofiltration Membranes in Edible Oil Processing", Membrane Technology, vol. 107, 1999, pp. 5-8.
Galka, Ned, "Life Sciences: Trends in Biopharmaceutical Filtration and Clarification", Filtration & Separation, Apr. 2007, vol. 44, No. 3, 4 pages.
Gibson, et al., "Transport Properties of Porous Membranes Based on Electrospun Nanofibers", Colloids and Surfaces A: Physicochemical and Engineering Aspects, vols. 187-188, Aug. 31, 2001, pp. 469-481.
Hou Xiang-Lin, "China Oil Refining Technologies", China Petrochemical Press, 1st Edition, Dec. 1991, p. 677.
Office Action received for Chinese Patent Application No. 201880061113.9 mailed on May 7, 2022, 19 Pages (11 Pages of English Translation & 8 Pages of Official Copy).
Final Office Action Received for U.S. Appl. No. 14/118,490, mailed on Jun. 16, 2022, 14 Pages.
Non Final Office Action Received for U.S. Appl. No. 15/301,781, mailed on May 10, 2022, 20 Pages.
Final Office Action Received for U.S. Appl. No. 14/648,925, mailed on Jul. 19, 2022, 16 Pages.
Office Action received for Chinese Patent Application No. 201880061113.9 mailed on Oct. 26, 2022, 19 Pages (13 Pages of English translation & 6 Pages of Official copy).
Office Action received for Korean Patent Application No. 10-2022-7017603, mailing date Feb. 28, 2023, 14 Pages (7 Pages of English Translation & 7 Pages of Official Copy).
Final Office Action Received for U.S. Appl. No. 15/301,781, mailing date May 8, 2023, 20 Pages.
Non Final Office Action Received for U.S. Appl. No. 15/301,781, mailed on Jan. 23, 2023, 22 Pages.

(56) References Cited

OTHER PUBLICATIONS

Office Action received for Chinese Patent Application No. 202110189947.1 mailed on Sep. 15, 2022, 5 Pages (2 Pages of English Translation and 3 Pages of Official Copy).
Communication pursuant to Article 94(3) EPC received for European Patent Application No. 12814718.8 mailed on Jul. 29, 2022, 5 Pages.
Non Final Office Action Received for U.S. Appl. No. 14/118,490, mailed on Oct. 3, 2022, 12 Pages.
final Office Action Received for U.S. Appl. No. 15/301,781, mailed on Oct. 3, 2022, 18 Pages.
Office Action received for Chinese Patent Application No. 202110189947.1 mailing date Mar. 24, 2023, 8 Pages (4 Pages of English Translation and 4 Pages of Official copy).
Communication pursuant to Article 94(3) EPC received for European Patent Application No. 18765711.9 mailing date Jul. 27, 2023, 5 Pages.
Examination Report received for Canadian Patent Application No. 3,116,905 issued on Feb. 25, 2022, 4 pages.
International Preliminary Report on Patentability received for PCT Patent Application No. PCT/US2019/059027, mailing date May 14, 2021, 8 pages.
International Search Report and Written Opinion received for PCT Patent Application No. PCT/US2019/059027 mailing date Jan. 20, 2020, 10 pages.
Invitation to Respond to Written Opinion received for Singapore Application No. 10201600617P, mailing date Nov. 3, 2021, 4 Pages.
Office Action received for Korean Patent Application No. 10-2021-7013160, mailing date Jul. 20, 2022, 17 Pages (5 Pages of English translation & 12 Pages of Official Copy).
Office Action received for Korean Patent Application No. 10-2021-7013160, mailing date May 26, 2023, 7 Pages (3 Pages of English Translation & 4 Pages of Official copy).
Communication pursuant to Article 94(3) EPC received for European Patent Application No. 16708843.4 mailing date Feb. 10, 2023, 4 Pages.
Communication pursuant to Article 94(3) EPC received for European Patent Application No. 16708843.4 mailing date May 3, 2022, 6 Pages.
Communication pursuant to Article 94(3) EPC received for European Patent Application No. 16708843.4 mailing date Oct. 7, 2020, 6 Pages.
Non Final Office Action Received for U.S. Appl. No. 17/290,024, mailing date Apr. 13, 2023, 28 Pages.
Communication pursuant to Article 94(3) EPC received for European Patent Application No. 17195327.6 mailing date Apr. 14, 2020, 6 Pages.
Communication pursuant to Article 94(3) EPC received for European Patent Application No. 17195327.6 mailing date Oct. 12, 2020, 6 Pages.
Office Action received for Chinese Patent Application No. 201510849372.6 mailing date Dec. 29, 2020, 13 Pages (5 Pages of English Translation and 8 Pages of Official Copy).
Office Action received for Chinese Patent Application No. 201510849372.6 mailing date Sep. 11, 2020, 9 Pages (4 Pages of English translation & 5 Pages of official copy).
First Examination Report received for Indian Application No. 201717028987 mailing date Dec. 27, 2019, 5 Pages.
Office Action received for Chinese Patent Application No. 201810258257.5 mailing date Jan. 4, 2021, 14 Pages (8 Pages of English Translation & 6 Pages of Official Copy).
Office Action received for Chinese Patent Application No. 201810258257.5 mailing date Mar. 19, 2020, 15 Pages (7 Pages of English translation & 8 Pages of official copy).
First Examination Report received for Indian Application No. 201918002024 mailing date Sep. 10, 2020, 7 Pages.
Office Action received for Chinese Patent Application No. 201980081896.1 mailing date Jun. 15, 2022, 26 Pages (14 Pages of English Translation & 12 Pages of Official Copy).
Office Action received for Chinese Patent Application No. 201980081896.1 mailing date Apr. 28, 2023, 19 Pages (13 Pages of English translation & 6 Pages of Official copy).
Office Action received for Chineses Patent Application No. 201980081896.1 mailing date Dec. 13, 2022, 19 Pages (13 Pages of English Translation & 6 Pages of Official copy).
Office Action received for Japanese Patent Application No. 2020171157 mailing date Oct. 26, 2021, 7 Pages (3 Pages of English Translation & 4 Pages of Official copy).
Office Action received for Japanese Patent Application No. 2021523066 mailing date Jul. 12, 2022., 18 Pages (14 Pages of English Translation & 4 Pages of Official copy).
Office Action received for Japanese Patent Application No. 2021-523066 mailing date Mar. 22, 2023, 8 Pages (4 Pages of English Translation and 4 Pages of Official copy).
Office Action received for Canadian Patent Application No. 3,116,905 mailing date Nov. 8, 2022, 5 Pages.
Office Action received for Canadian Patent Application No. 3,116,905 mailing date Jul. 12, 2023, 4 Pages.
Communication pursuant to Article 94(3) EPC received for European Patent Application No. 16708843.4 mailing date Jan. 24, 2024, 6 Pages.
Li, Jun,"HygieneCourse of Medicine GMP", China Pharmaceutical Science and Technology Press, Nov. 2003, 5 Pages.
Liu, Zheng, "Practical Manual of Laboratory Biosafety Management and Laboratory Safety Assessment Accreditation Standards", Ningxia Dadi audiovisual publishing house, vol. 2, Jun. 2004, 5 pages.
Office Action received for Chinese Patent Application No. 201810258257.5 mailing date Nov. 21, 2023, 12 Pages (6 Pages of English Translation & 6 Pages of Official Copy).
Office Action received for Japanese Patent Application No. 2022-163021 mailing date Dec. 12, 2023, 5 Pages (2 Page of English translation and 3 pages of official copy).
Office Action received for Korean Patent Application No. 10-2022-7017603 mailing date Sep. 22, 2023, 15 Pages (7 Pages of English translation & 8 Pages of official copy).
Office Action received for Korean Patent Application No. 10-2022-7017603 mailing date May 27, 2024, 9 Pages (4 Pages of English translation & 5 Pages of official copy).
Office Action received for Chinese Patent Application No. 201810258257.5 mailing date Jun. 11, 2024, 17 Pages (06 Pages of English Translation & 11 Pages of Official Copy).
Dotti, F. et al., "Electrospun porous mats for high efficiency filtration", Journal of Industrial Textiles, vol. 37, No. 2, Oct. 2007, pp. 151-162.
Hutten, I., "Testing of Nonwoven Filter media", Chapter 6 in Handbook of Nonwoven Filter Media, 2007, pp. 245-290.
Patel, S. U., "Improving performance and drainage of coalescing filters", Doctoral dissertation, University of Akron, 2010, 226 pages.

* cited by examiner

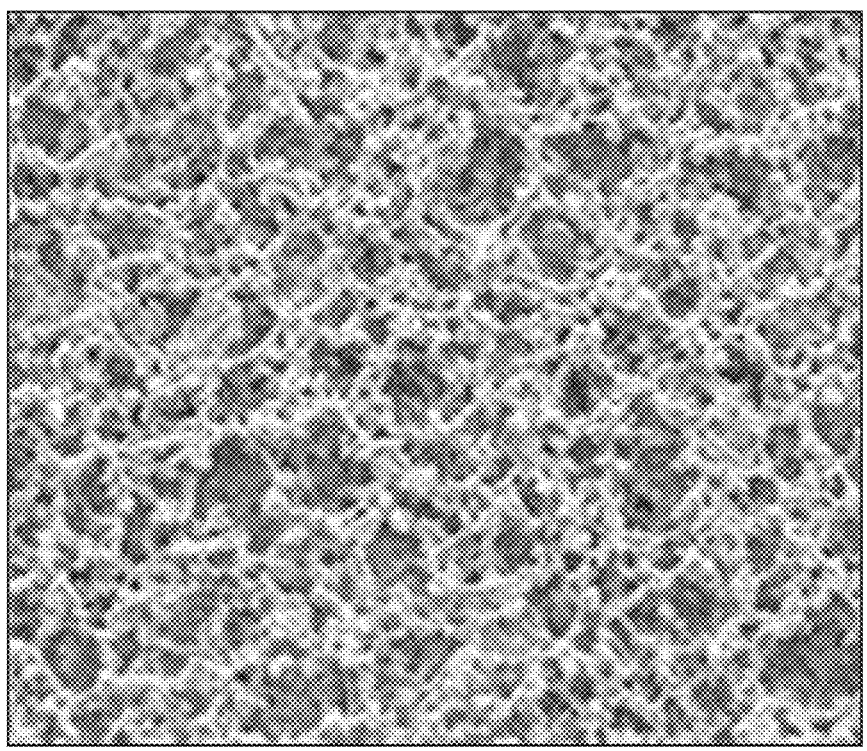
Figure 3.1
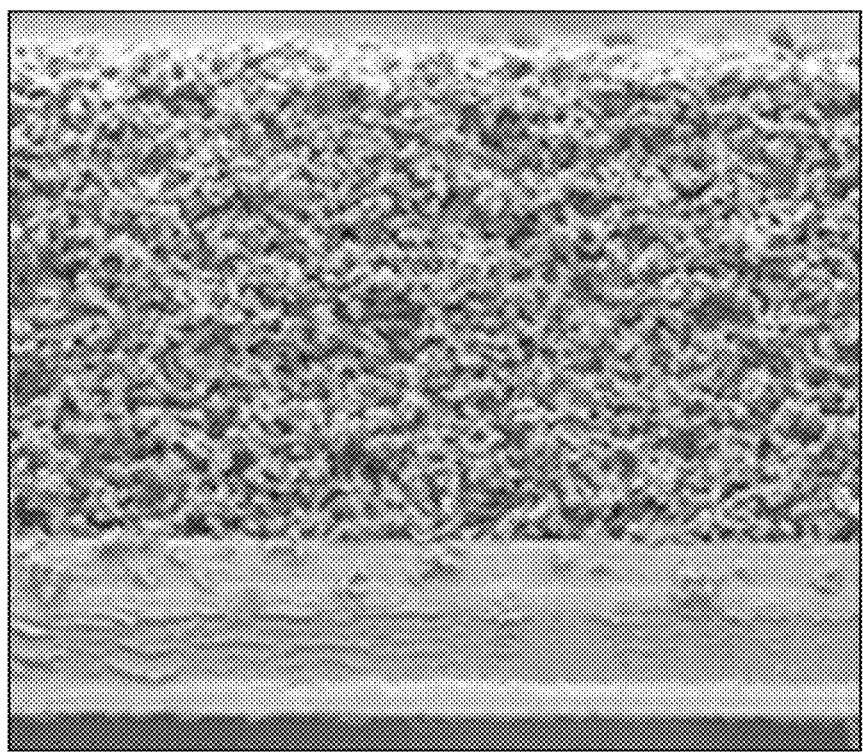
Figure 3.2

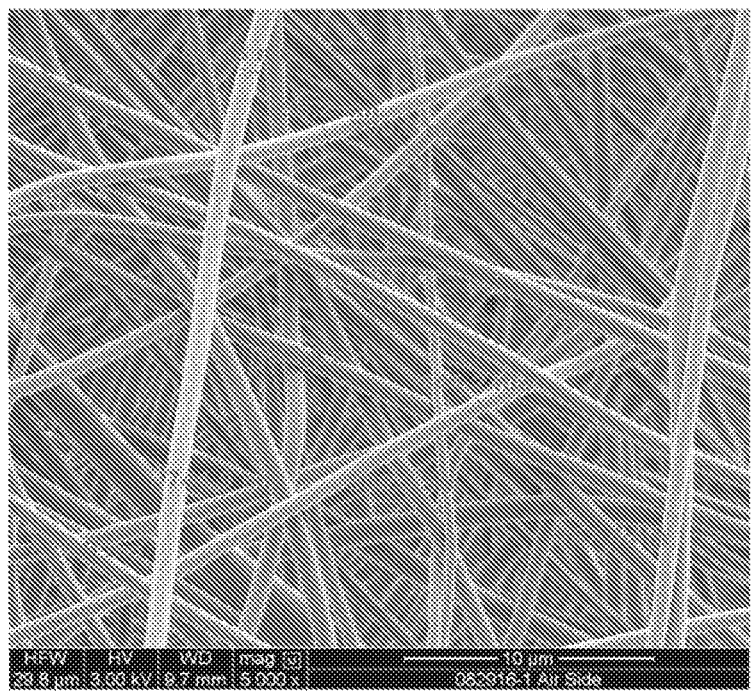
Figure 26.1
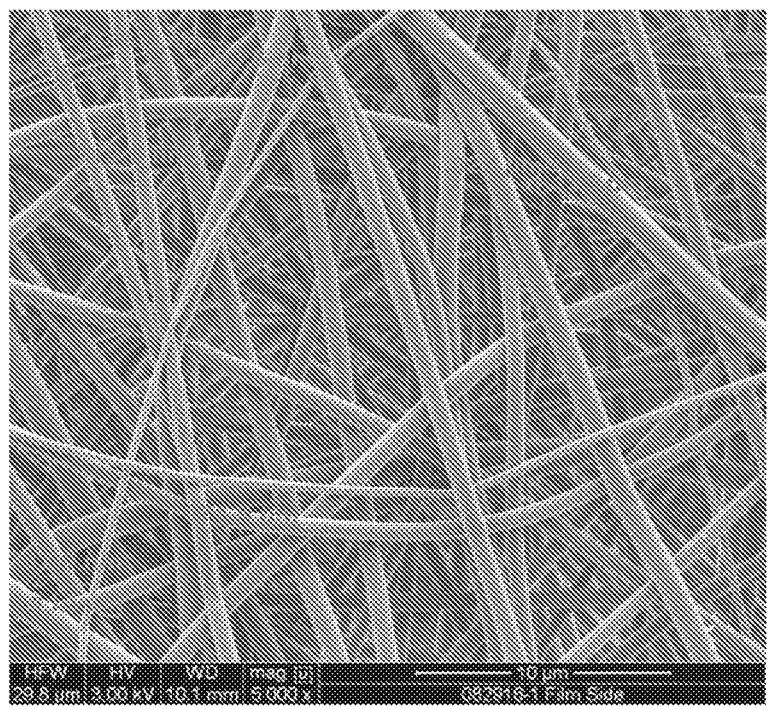
Figure 26.2

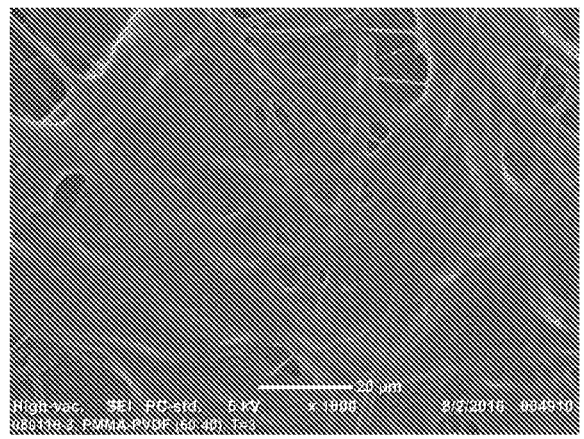
Figure 28.1
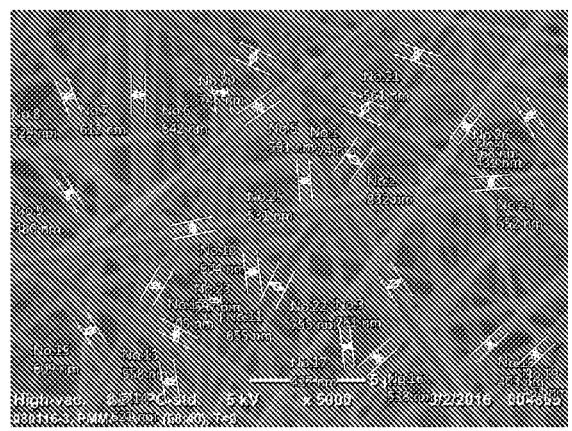
Figure 28.2
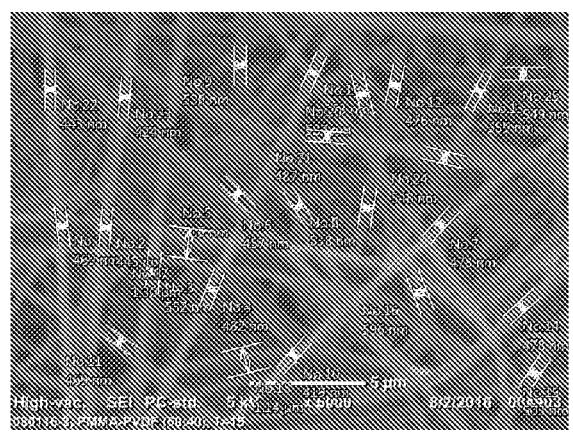
Figure 28.3

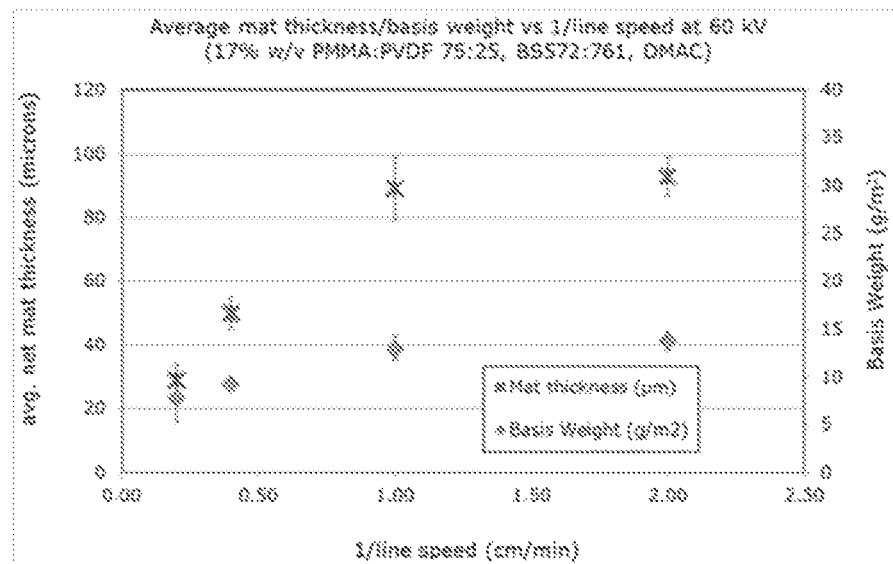
Figure 33.1
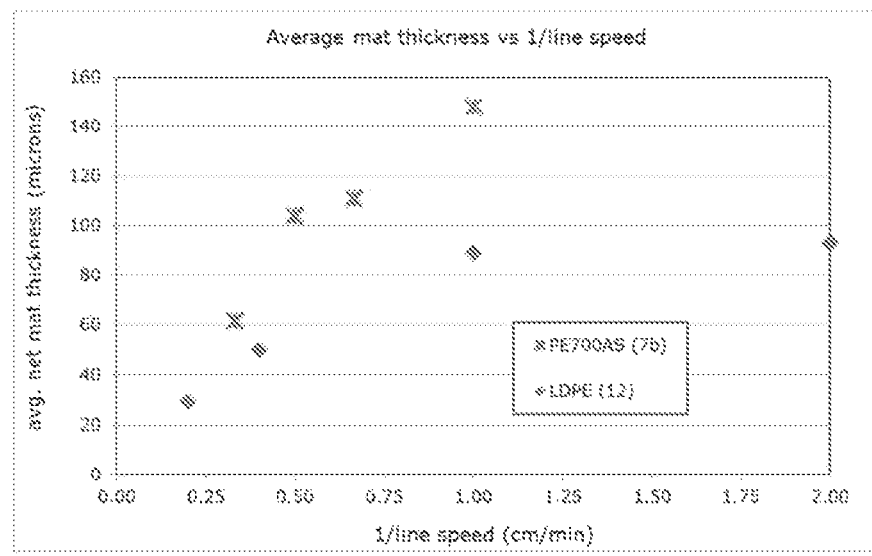
Figure 33.2

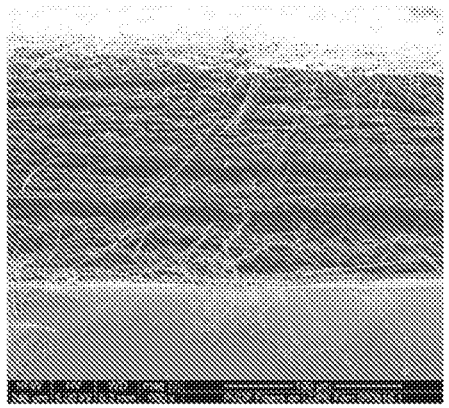
Figure 36.1
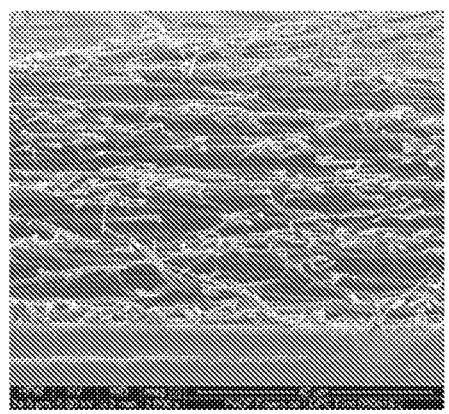
Figure 36.2
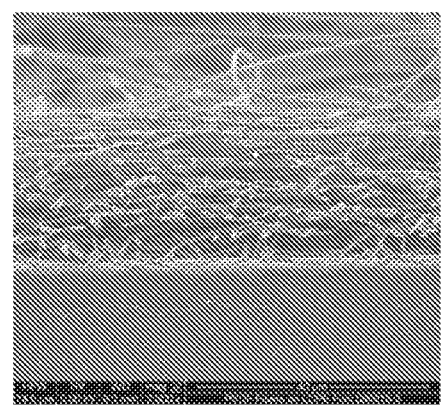
Figure 36.3

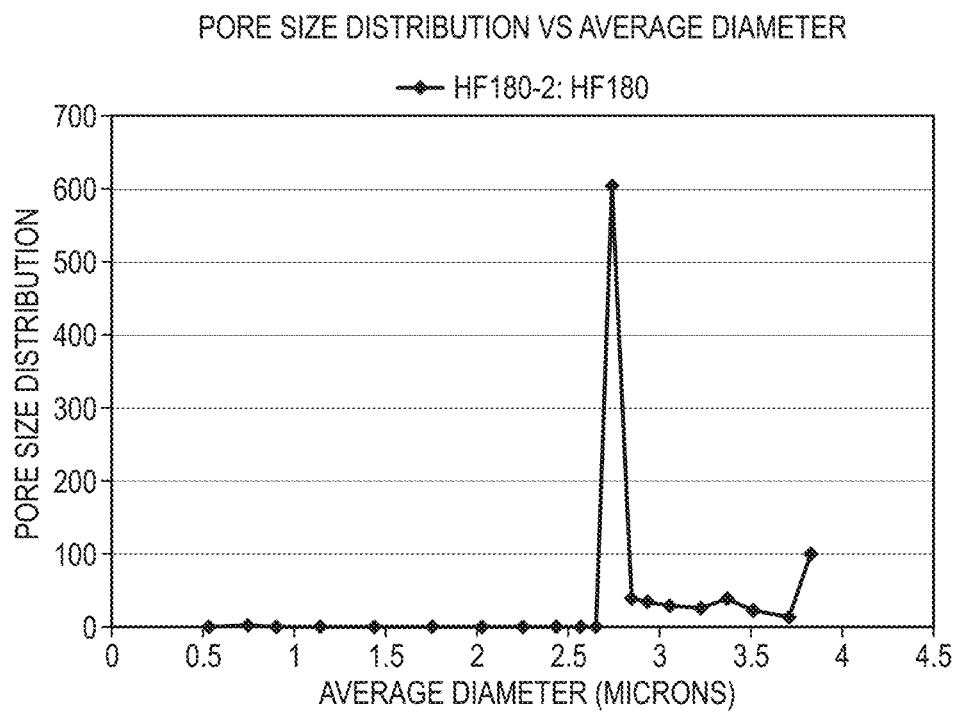
Figure 38.1
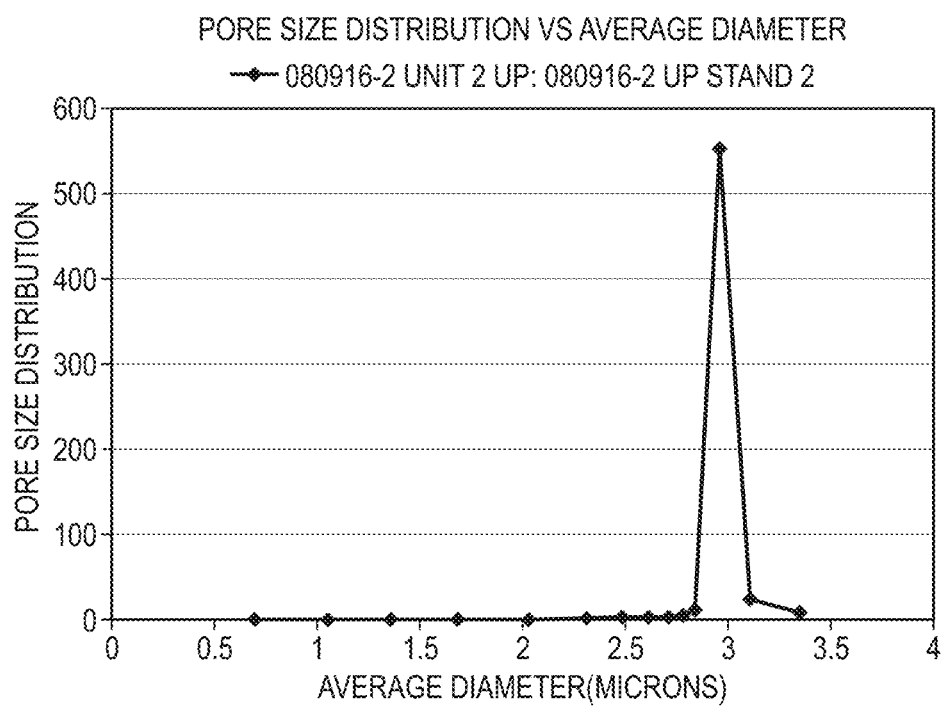
Figure 38.2

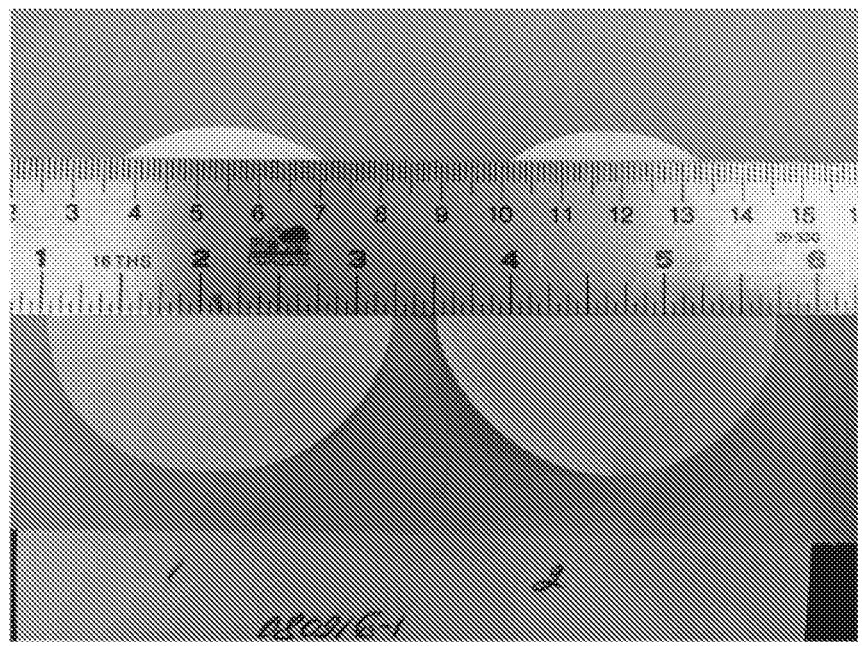
Figure 43.1
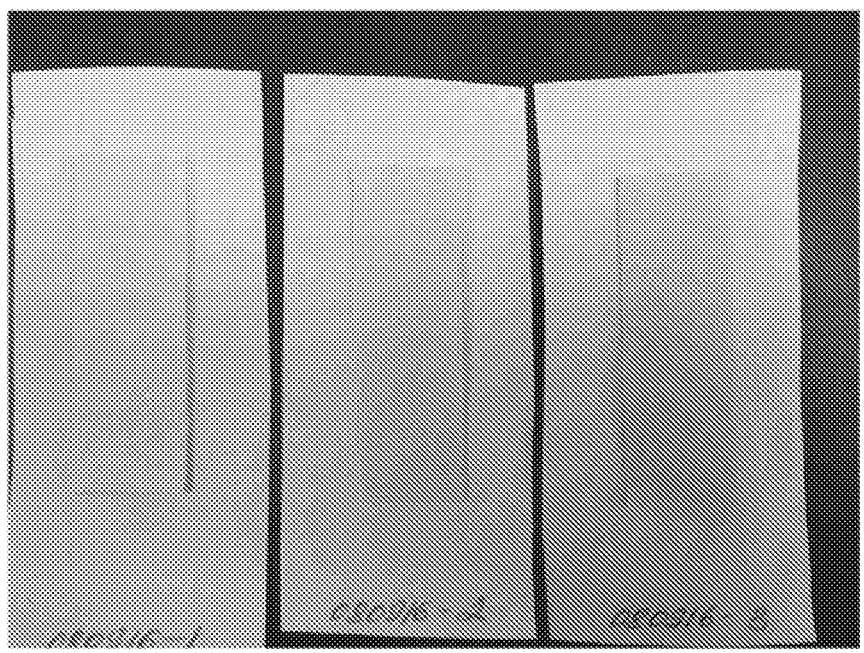
Figure 43.2

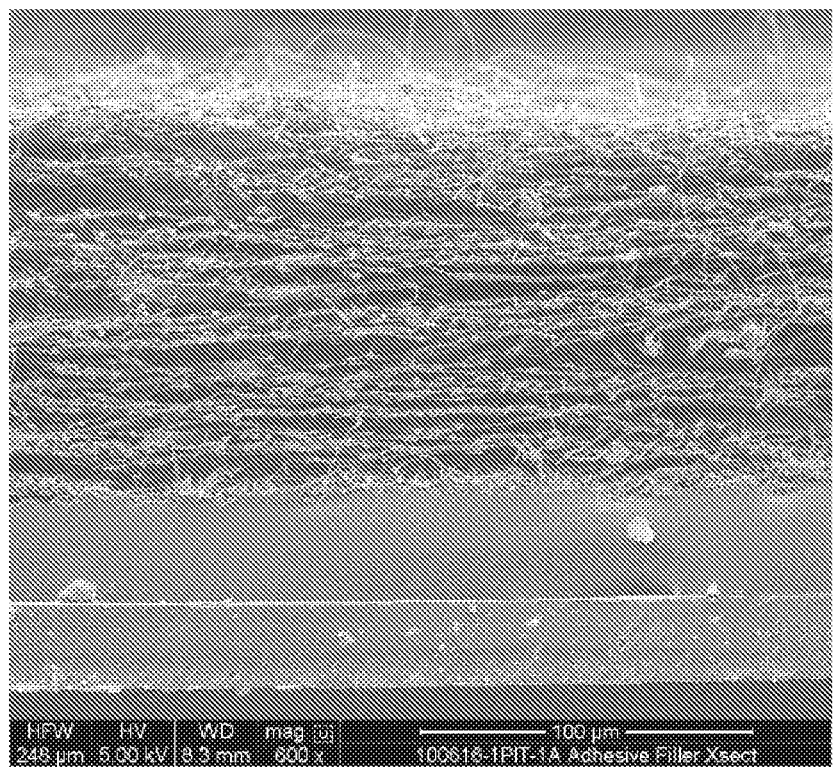
Figure 44.1
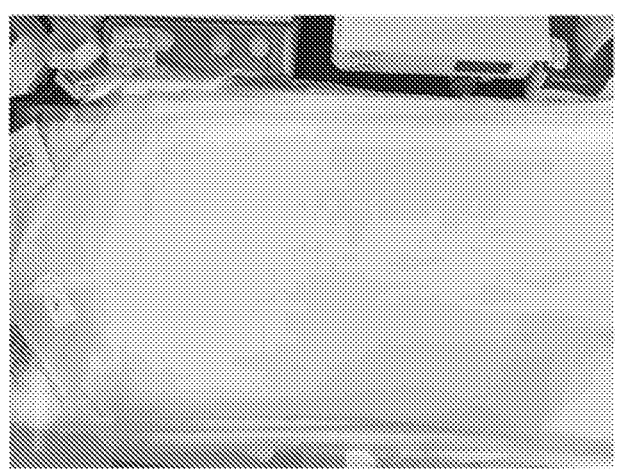
Figure 44.2

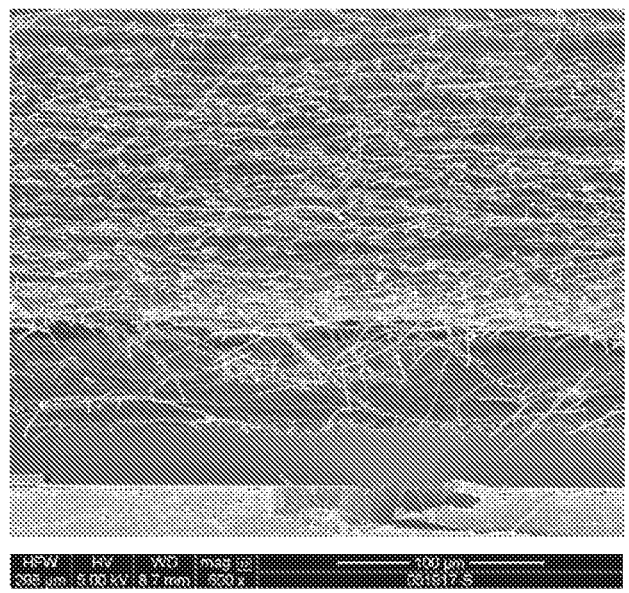
Figure 44.3
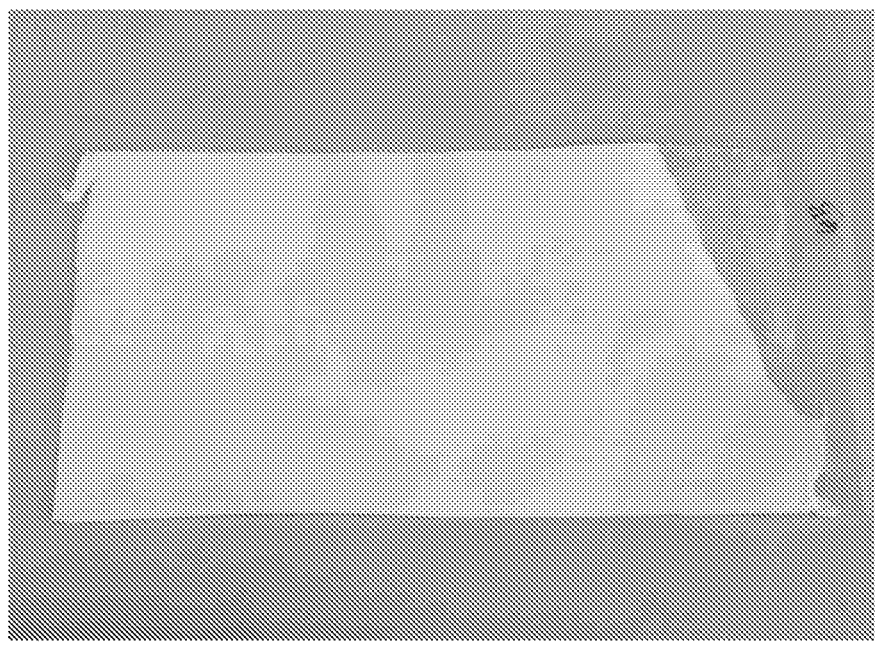
Figure 44.4

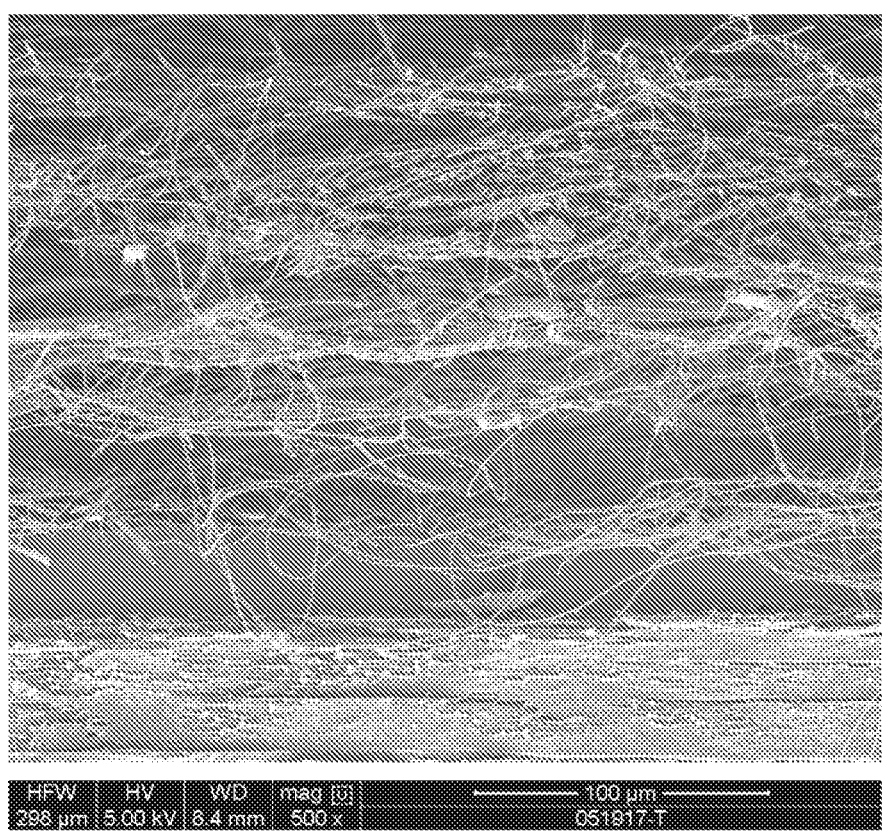
Figure 44.5

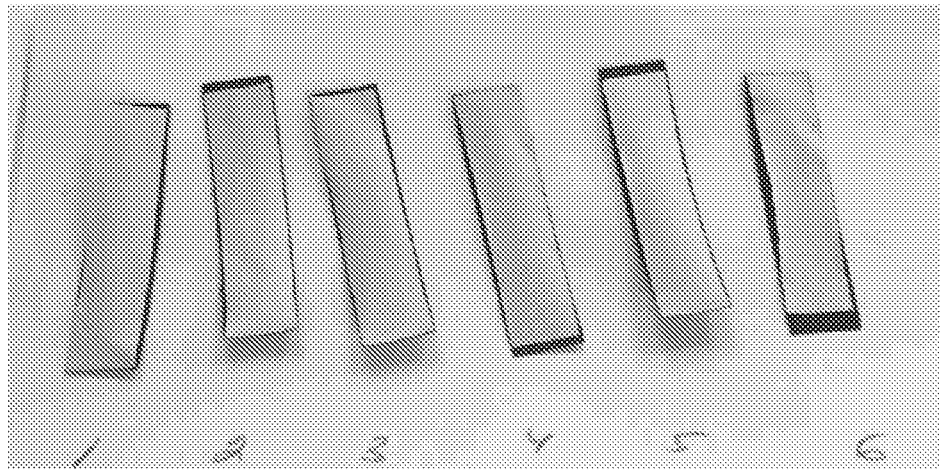
Figure 45.1
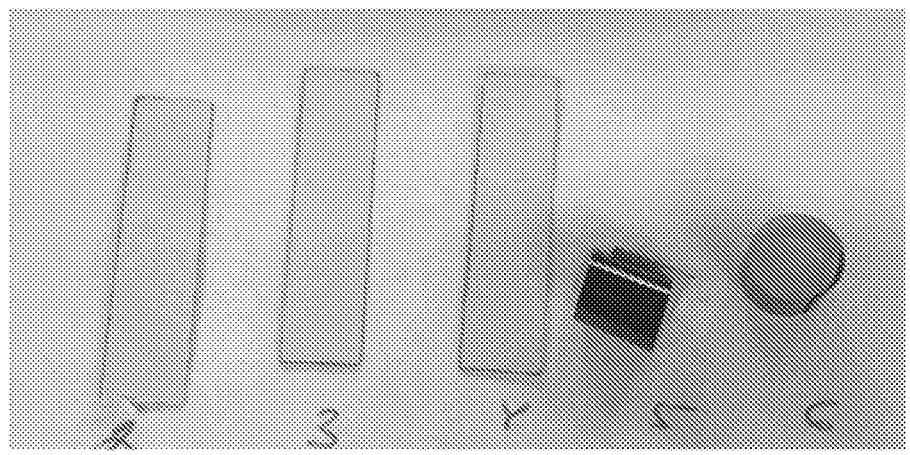
Figure 45.2

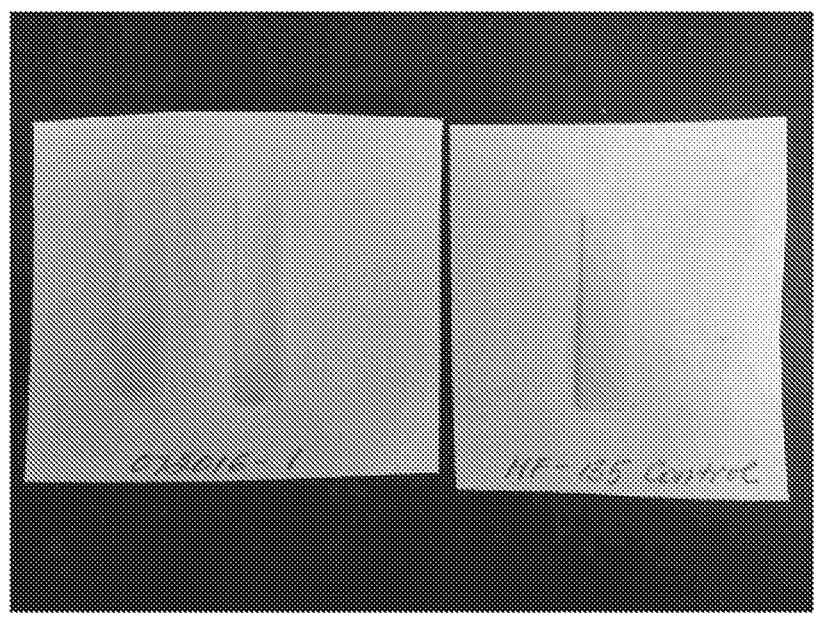
Figure 47.1
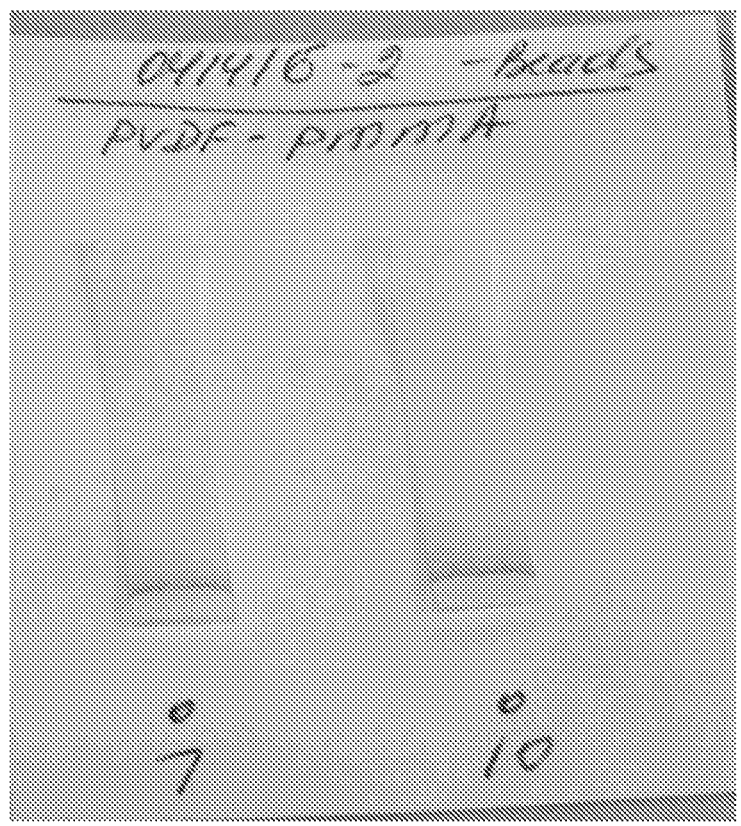
Figure 47.2

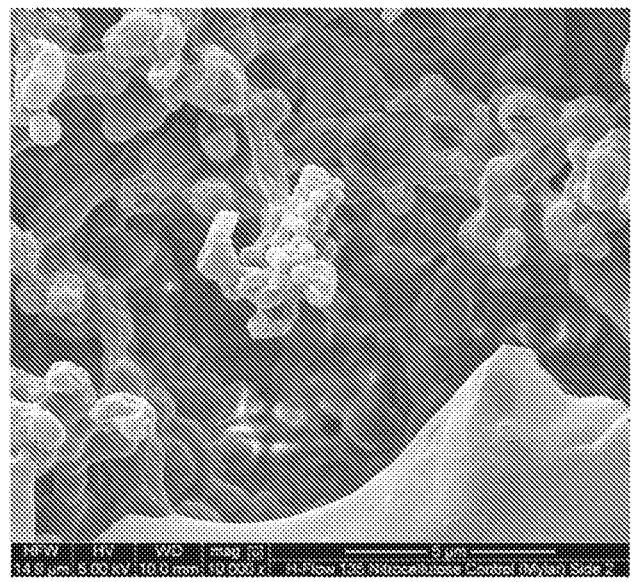
Figure 48.1
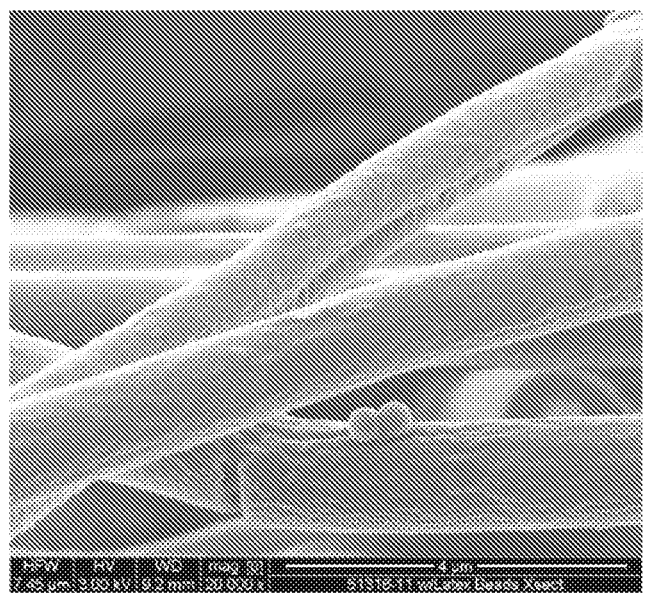
Figure 48.2

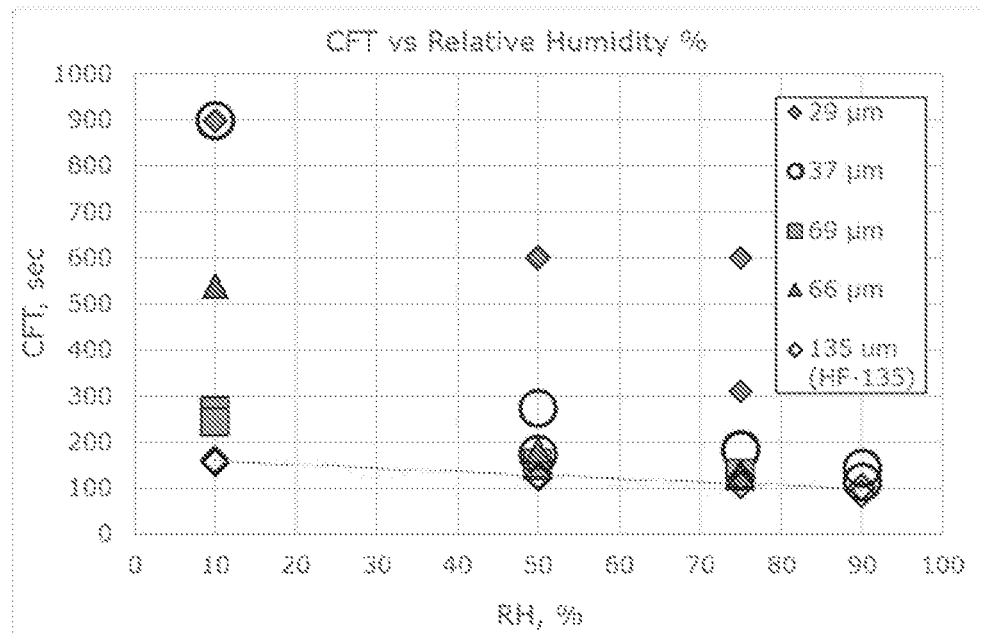
Figure 52.1
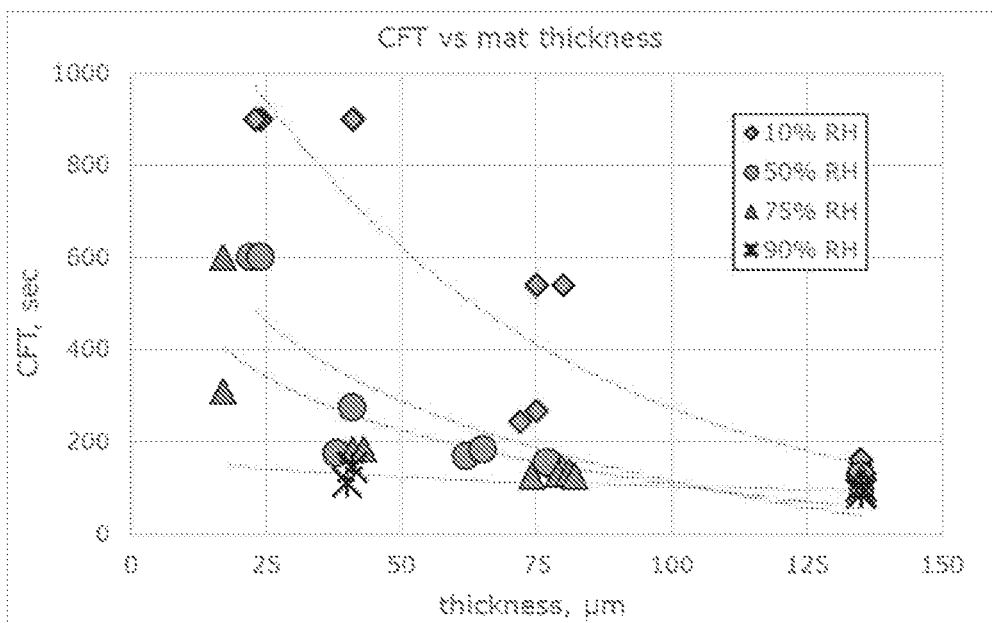
Figure 52.2

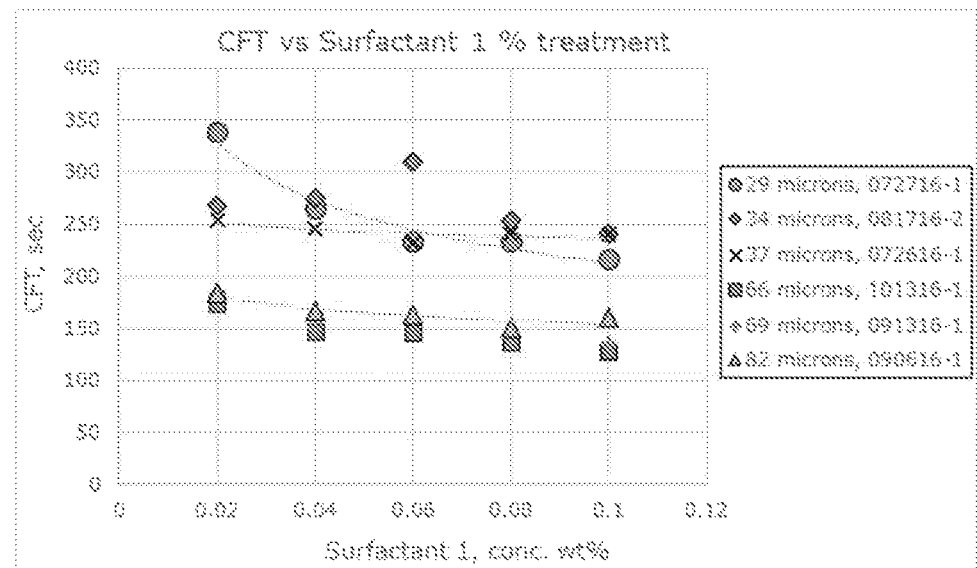
Figure 54.1
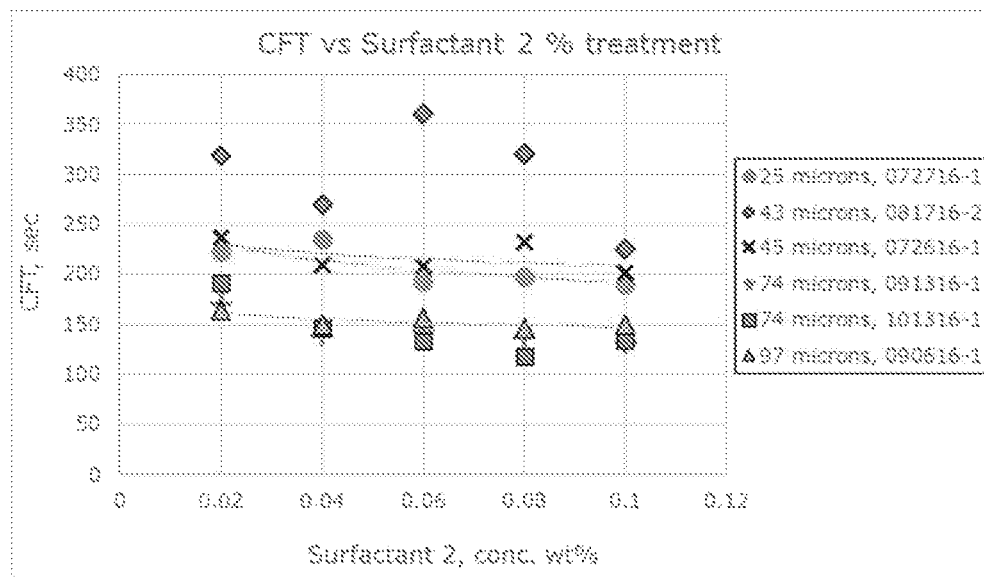
Figure 54.2

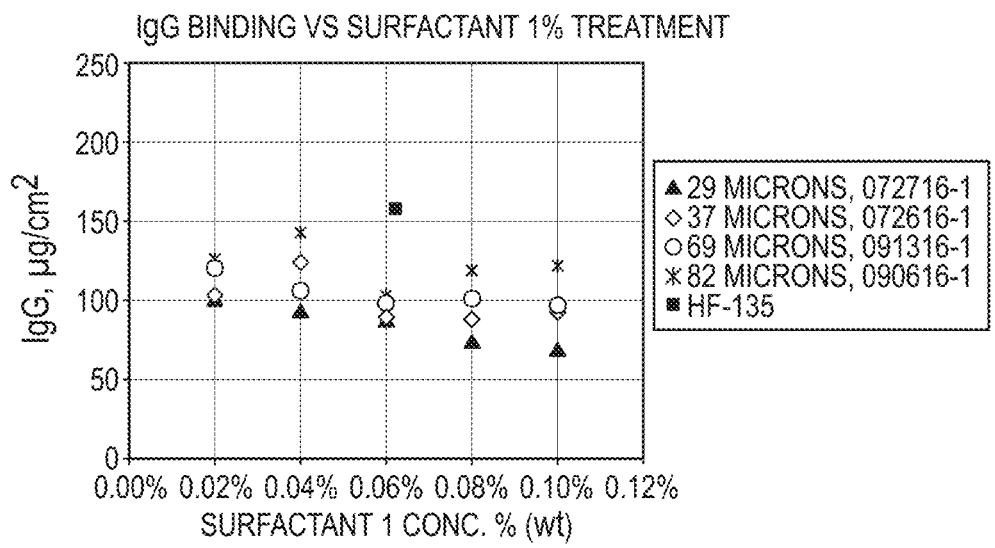
Figure 56.1
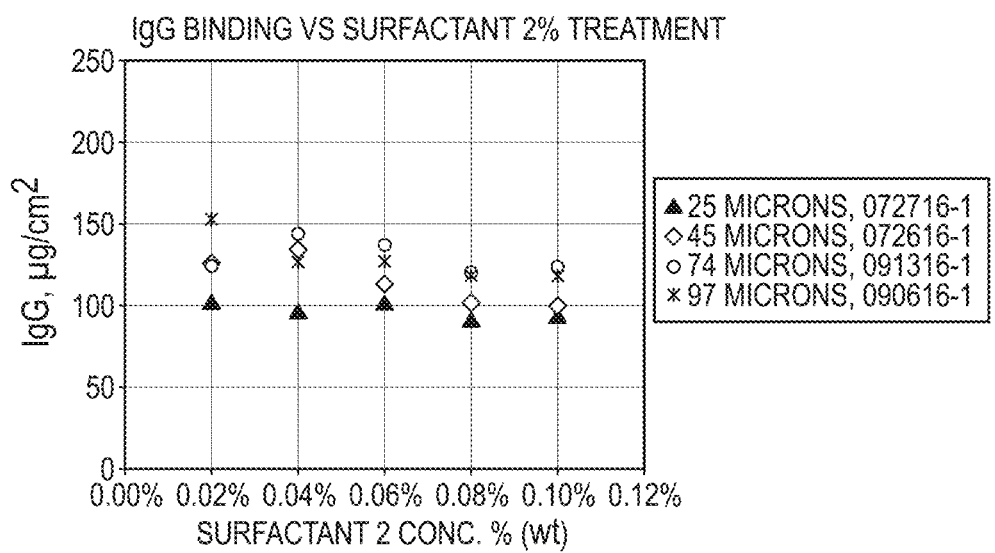
Figure 56.2

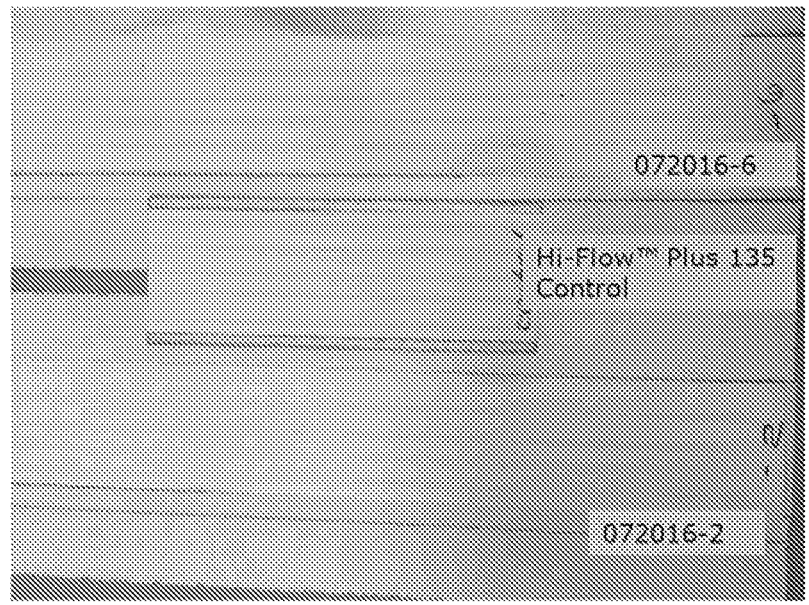
Figure 58.1
Figure 58.2

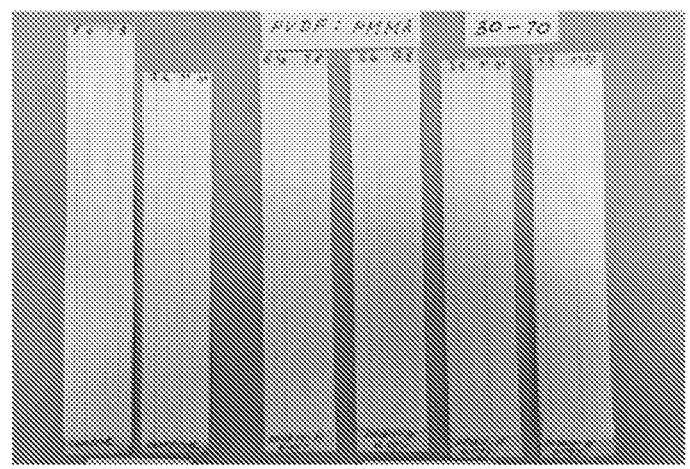
Figure 58.3

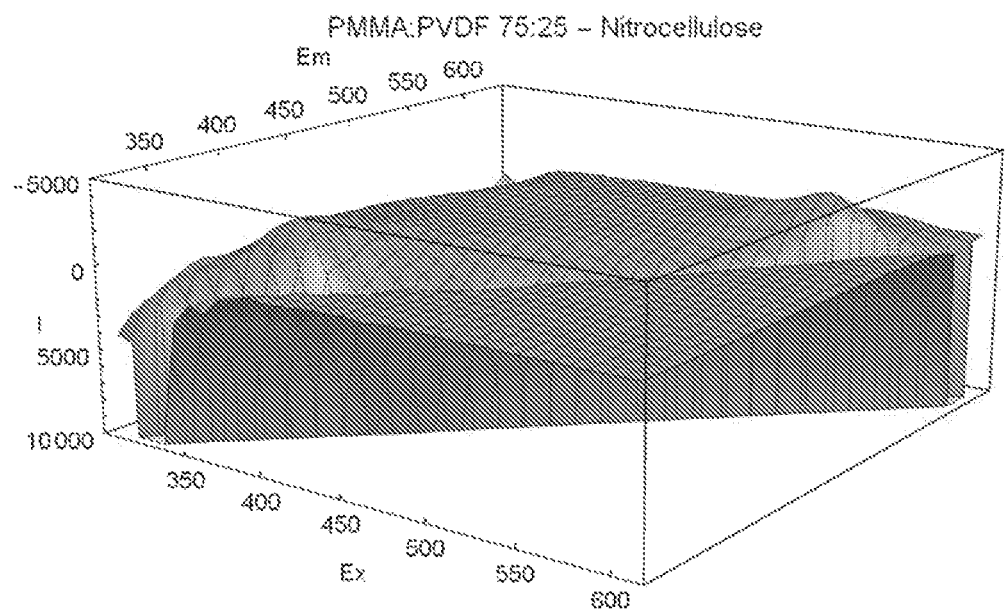
Figure 60.1
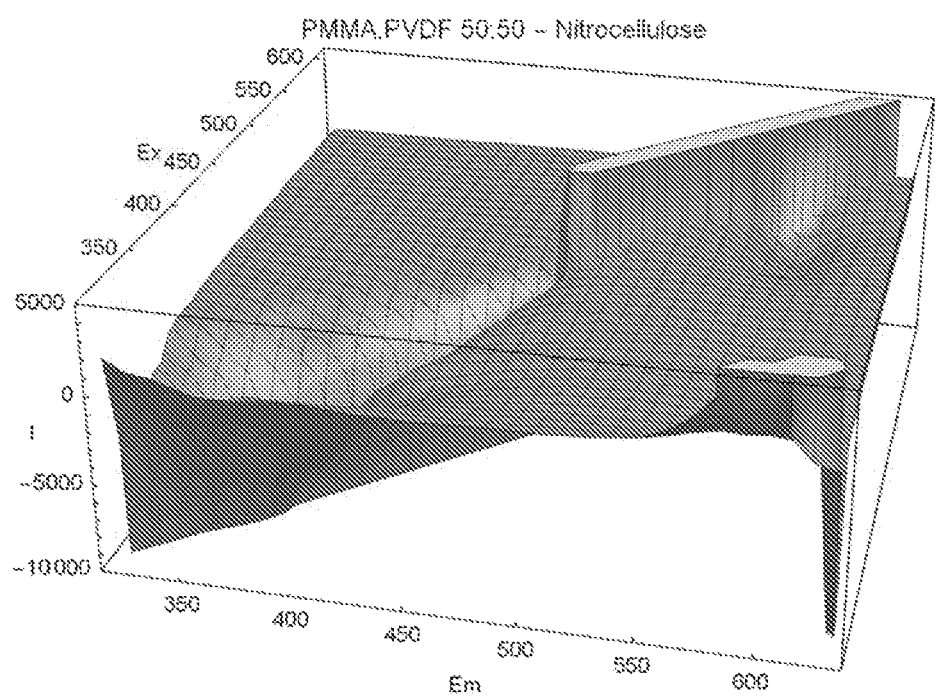
Figure 60.2

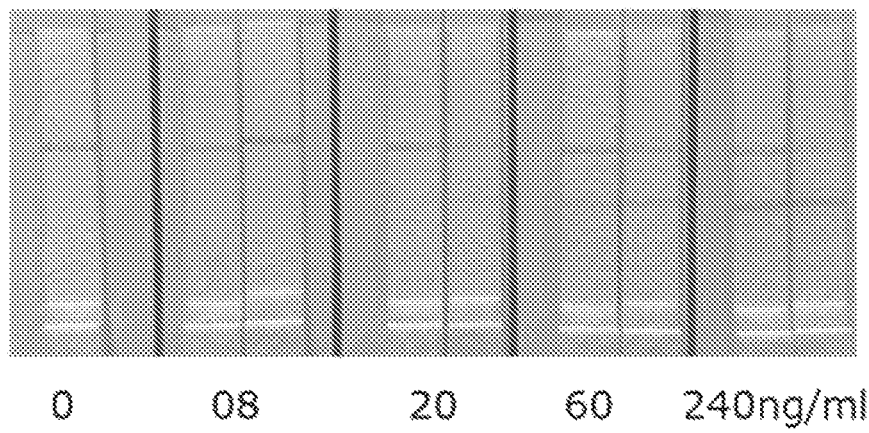
Figure 71.1
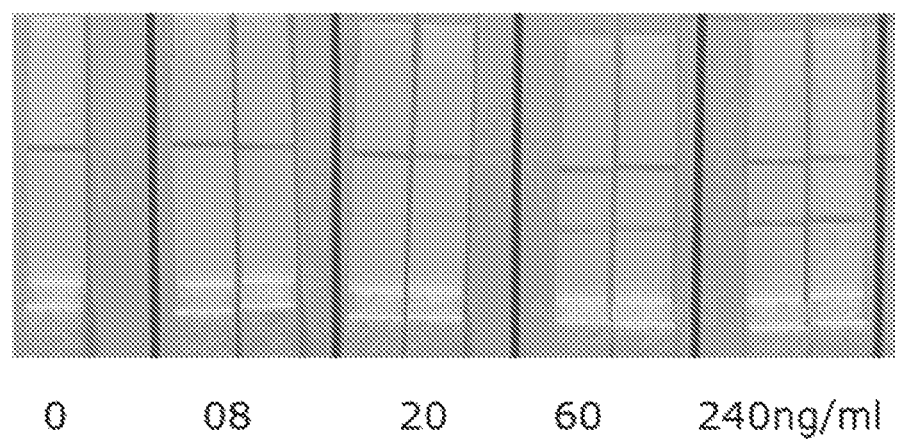
Figure 71.2

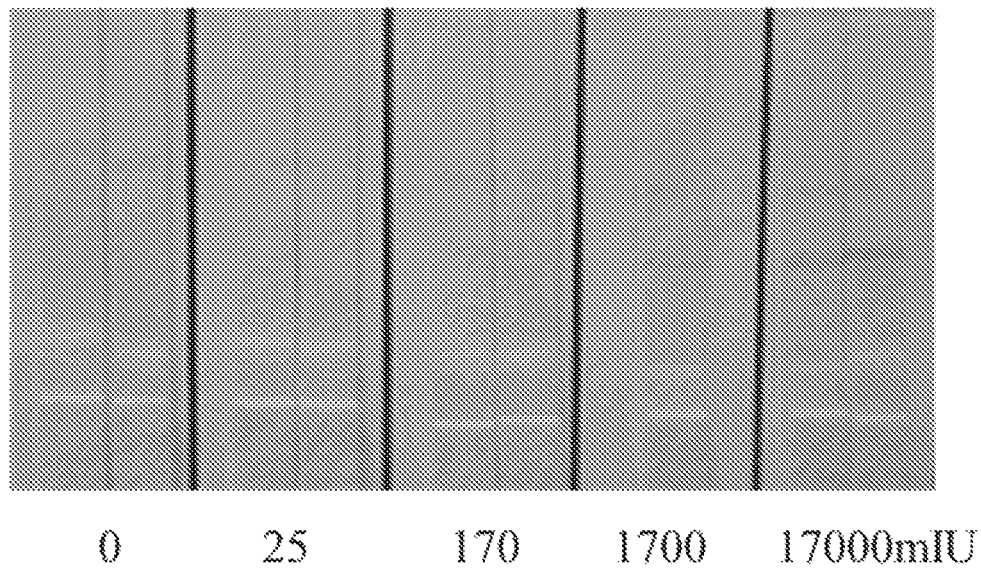
Figure 72.1
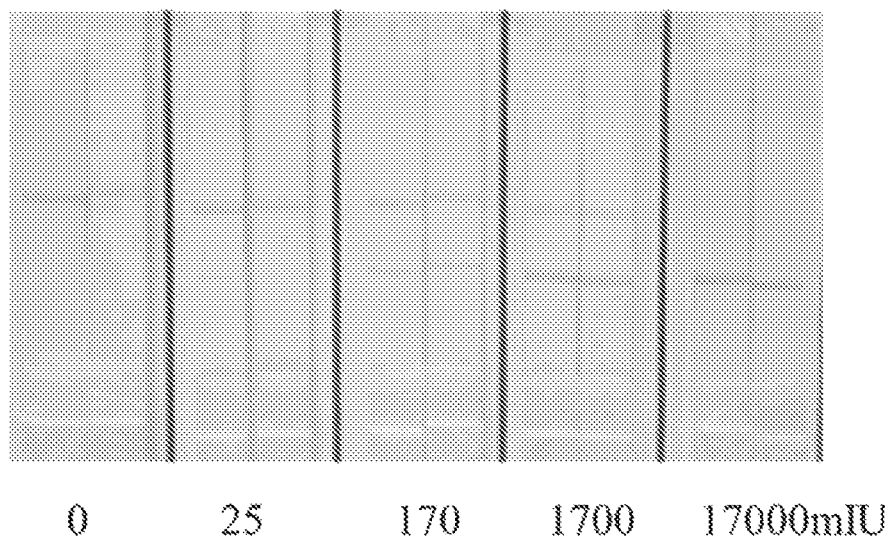
Figure 72.2

NON-WOVEN FIBER MEMBRANES

RELATED APPLICATIONS

The present application is a US National Stage application of International Application No. PCT/IB2018/000918, filed Jul. 20, 2018, which claims the benefit of priority to U.S. Provisional Patent Application Ser. No. 62/535,586 filed Jul. 21, 2017, each of which is hereby incorporated by reference in its entirety.

BACKGROUND

Lateral flow diagnostic devices require a structure through which aqueous media and nanoparticles (e.g., gold or latex beads) pass by capillary flow. This structure, typically a porous membrane, must possess sufficient pore size and porosity to achieve suitable flow rates and allow nanoparticle mobility while also having adequate protein binding capacity to allow antigen binding to the surface. Membranes for use in lateral flow diagnostic devices are conventionally produced using either air casting or a phase inversion method. These methods are complex, slow, and sensitive to environmental conditions and various process parameters, for example, polymer solution conditions (% solids, solvent compositions), temperature, humidity, and substrate, and can produce variable pore sizes and thicknesses cross and down-web in the same production run.

Air-casting is conventionally preferred over non-solvent induced phase separation (NIPS) membrane casting because it has better capabilities to produce symmetric membranes with a mean flow pore diameter (MFP) of greater than 2 microns and a higher porosity. Air-cast nitrocellulose membranes are manufactured on large, expensive machines at slow line speeds of about 1 ft/min by solvent evaporation on a moving web from a nitrocellulose polymer solution. Air-casting nitrocellulose membrane has its challenges both in manufacturing and with the end-users, particularly in terms of consistency, handling, shelf-life, and the flammability of nitrocellulose. Also, nitrocellulose membrane cast onto non-porous films often has handling issues, including brittleness and delamination, making it challenging to use in assay manufacturing.

In lateral flow diagnostic devices, the detector particles are typically 40 nm gold or 400 nm latex beads, which have to freely migrate with the liquid front in the membrane for proper assay functionality in forming test and control lines. Higher MFP and porosity are needed in lateral flow diagnostic devices for sufficiently fast capillary flow time (CFT) and to allow for detector particle bead mobility without liquid-bead flow front separation.

Thus, there is a need in the art for improved membranes useful in lateral flow diagnostic devices and more efficient manufacturing processes for the creation of such membranes.

SUMMARY

In certain aspects, provided herein are non-woven fiber membranes that are suitable for use in the assay developing regions of lateral flow diagnostic devices. In some embodiments, the membrane comprises a non-woven fiber mat. In certain embodiments, the non-woven fiber membranes comprise nanofibers having an average fiber diameter between 200 nm to 1000 nm, wherein the membranes have MFPs of greater than about 1.5 microns and porosities of at least 80% to 90%. In certain embodiments, the non-woven fiber membranes comprise nanofibers produced by electrospinning a polymer or a blend of polymers, for example, polymethacrylate (PMMA), poly(vinylidene fluoride) (PVDF), or a blend thereof. In some embodiments, the non-woven fiber membranes comprise nanofibers produced by electroblowing.

In some aspects, provided herein are lateral flow diagnostic devices designed for detecting an analyte in a sample. In some embodiments, the lateral flow diagnostic devices provided herein can comprise a sample port designed to receive a sample, a conjugate pad, an assay developing region comprising the non-woven fiber membrane, and/or an absorbent pad. In some embodiments, the conjugate pad, the non-woven fiber membrane, and the absorbent pad are connected to permit capillary flow communication with each other.

In certain aspects, provided herein are methods of using such lateral flow diagnostic devices to detect an analyte, such as a metabolite, a hormone, a therapeutic drug, a drug of abuse, a peptide, an antibody, and/or an antigen in a biological sample.

Further, in some aspects provided herein are methods of producing the non-woven fiber membranes, electrospun membranes and/or electroblown membranes described herein. In some embodiments, the method comprises electrospinning (e.g., needleless electrospinning) or electroblowing a polymer preparation onto a non-porous film or porous substrate. In certain embodiments, the methods of producing the non-woven fiber membranes comprise electrospinning (e.g., needleless electrospinning) a solution containing about 15% to 20% PMMA and/or PVDF in a solvent N,N-Dimethylacetamide (DMAC) and/or N,N-Dimethylformamide (DMF).

In one embodiment the present invention contemplates a non-woven fiber membrane comprising nanofibers having an average fiber diameter from 200 nm to 1000 nm, wherein the membrane has a mean flow pore diameter of greater than about 1 micron and a porosity of at least 80%.

In another embodiment, the present invention contemplates that the non-woven fiber membrane is generated by electrospinning or electroblowing.

In still another embodiment the present invention contemplates that the non-woven fiber membrane has a mean flow pore diameter is about or greater than about 2 microns.

In still yet another embodiment the present invention contemplates that the non-woven fiber membrane has a porosity that is at least 85%.

In still yet another embodiment the present invention contemplates that the non-woven fiber membrane comprises nanofibers that comprise a polymer or a polymer blend.

In still yet another embodiment the present invention contemplates that the polymer or the polymer blend is selected from one or more of: nylon-46, nylon-66, polyurethane (PU), polybenzimidazole, polycarbonate, polyacrylonitrile, polyvinyl alcohol, polylactic acid (PLA), polyethylene-co-vinyl acetate (PEVA), PEVA/PLA, polymethylmethacrylate (PMMA), PMMA/tetrahydroperfluorooctylacrylate (TAN), polyethylene oxide (PEO), collagen-PEO, polystyrene (PS), polyaniline (PANI)/PEO, PANI/PS, polyvinylcarbazole, polyethylene terephthalate (PET), polyacrylic acid-polypyrene methanol (PAA-PM), polyamide (PA), silk/PEO, polyvinylphenol (PVP), polyvinylchloride (PVC), cellulose acetate (CA), PAA-PM/PU, polyvinyl alcohol (PVA)/silica, polyacrylamide (PAAm), poly(lactic-co-glycolic acid) (PLGA), polycarprolactone (PCL), poly(2-hydroxyethyl methacrylate) (HEMA), poly(vinylidene difluoride) (PVDF), PVDF/PMMA, polyether imide (PEI), polyethylene glycol (PEG), poy(ferrocenyldimethylsilane) (PFDMS), Nylon6/montmorillonite (Mt), poly(ethylene-co-vinyl alcohol), polyacrylonitrile (PAN)/TiO$_2$, polycaprolactone (PCL)/metal, polyvinyl porrolidone, polymetha-phenylene isophthalamide, polyethylene (PE), polypropylene (PP), nylon-12, polyethylene terephthalate (PET), polyethylene naphthalate (PEN), polyether sulfone (PES), polyvinyl butyral (PVB), PET/PEN.

In still yet another embodiment the present invention contemplates that the polymer is selected from PMMA, PVDF, or a blend of PMMA and PVDF.

In still yet another embodiment the present invention contemplates that the blend of PMMA and PVDF has the weight ratio of PMMA to PVDF from 1:99 to 99:1.

In still yet another embodiment the present invention contemplates that the ratio of PMMA to PVDF is 10:90, 15:85, 20:80, 25:75, 30:70, 35:65, 40:60, 45:55, 50:50, 55:45, 60:40, 65:35, 70:30, 75:25, 80:20, 85:15, or 90:10.

In still yet another embodiment the present invention contemplates that the nanofibers have an average fiber diameter of about: 500 nm, 550 nm, 600 nm, 650 nm, 700 nm, 750 nm, 800 nm, 850 nm, 900 nm, 950 nm, or 1000 nm.

In still yet another embodiment the present invention contemplates that a mean flow pore diameter of at least: 1.0 microns, 1.5 microns, 1.75 microns, 2.0 microns, 2.25 microns, 2.5 microns, 2.75 microns, 3.0 microns, 3.5 microns, or 4.0 microns.

In still yet another embodiment the present invention contemplates that the non-woven fiber membrane has pores, wherein at least 90% of pores have a diameter of between 2.75 microns and 3.25 microns. In still yet another embodiment the present invention contemplates that at least 95% of pores have a diameter of between 2.75 microns and 3.25 microns. In still yet another embodiment the present invention contemplates that at least 99% of pores have a diameter of between 2.75 microns and 3.25 microns.

In still yet another embodiment the present invention contemplates that the non-woven fiber membrane has a thickness of from 25 to 250 microns. In still yet another embodiment the present invention contemplates that the non-woven fiber membrane has a thickness of from 100 to 175 microns. In still yet another embodiment the present invention contemplates that the non-woven fiber membrane has a thickness of about 150 microns.

In still yet another embodiment the present invention contemplates that the non-woven fiber membrane further comprises a surfactant.

In still yet another embodiment the present invention contemplates that the non-woven fiber membrane has a capillary flow time of from 75 to 300 seconds. In still yet another embodiment the present invention contemplates that the non-woven fiber membrane has a capillary flow time of from 125 to 250 seconds. In still yet another embodiment the present invention contemplates that the non-woven fiber membrane has a capillary flow time of from 175 to 200 seconds.

In still yet another embodiment the present invention contemplates that the non-woven fiber membrane passes a detector bead mobility test for beads having a size of from 40 to 600 nm. In still yet another embodiment the present invention contemplates that the non-woven fiber membrane passes a detector bead mobility test for beads having a size of from 200 to 440 nm. In still yet another embodiment the present invention contemplates that the non-woven fiber membrane passes a detector bead mobility test for beads having a size of about 400 nm.

In still yet another embodiment the present invention contemplates that the non-woven fiber membrane having a protein binding capacity of at least about 70 to 120 µg/cm$^2$ for a thickness of at least about 40 to 60 microns.

In an embodiment of the present invention a device is contemplated for detecting an analyte in a sample comprising an assay developing region comprising a non-woven fiber membrane comprising a non-woven fiber membrane comprising nanofibers having an average fiber diameter from 200 nm to 1000 nm, wherein the membrane has a mean flow pore diameter of greater than about 1 micron and a porosity of at least 80%.

In another embodiment the present invention contemplates that the device is a lateral flow device.

In yet another embodiment the present invention contemplates that comprises a sample port designed to receive the sample, a conjugate pad, the assay developing region comprising the non-woven fiber membrane and an absorbent pad, wherein the conjugate pad, the non-woven fiber membrane and the absorbent pad are connected to permit capillary flow communication with each other.

In still yet another embodiment the present invention contemplates that the
    conjugate pad of the device contains particles conjugated
       to a first analyte binding agent that specifically binds to
       the analyte.

In still yet another embodiment the present invention contemplates that the assay developing region of the device comprises a test region immobilized therein a second analyte binding agent that specifically binds to the analyte.

In still yet another embodiment the present invention contemplates that the assay developing region of the device comprises a control region immobilized therein a particle binding agent that specifically binds to the particles.

In still yet another embodiment the present invention contemplates that the analyte is a metabolite, a hormone, a therapeutic drug, a drug of abuse, a peptide, an antibody or an antigen.

In still yet another embodiment the present invention contemplates that the analyte is luteinizing hormone, human chorionic gonadotrophin, cholesterol or glucose.

In still yet another embodiment the present invention contemplates that the method of detecting an analyte in a sample comprising contacting the analyte to the assay developing region of the device.

In an embodiment of the present invention a method is contemplated for producing an electrospun non-woven fiber membrane, said membrane comprising nanofibers having an average fiber diameter from 200 nm to 1000 nm, wherein the membrane has a mean flow diameter of greater than about 1 micron and a porosity of at least 80%, said method comprising electrospinning a polymer preparation comprising a solvent onto a non-porous film substrate.

In another embodiment of the method of the present invention contemplates that the non-porous film substrate is insoluble in the solvent for polymer preparation and the non-porous film substrate has no electric charge.

In yet another embodiment of the method of the present invention contemplates that the polymer preparation is selected from the group consisting of 1) a melt or 2) a solution of a polymer or a blend of polymers.

In still yet another embodiment of the method of the present invention contemplates that the polymer preparation comprises one or more polymers selected from: nylon-46, nylon-66, polyurethane (PU), polybenzimidazole, polycarbonate, polyacrylonitrile, polyvinyl alcohol, polylactic acid (PLA), polyethylene-co-vinyl acetate (PEVA), PEVA/PLA, polymethylmethacrylate (PMMA), PMMA/tetrahydroperfluorooctylacrylate (TAN), polyethylene oxide (PEO), collagen-PEO, polystyrene (PS), polyaniline (PANI)/PEO, PANI/PS, polyvinylcarbazole, polyethylene terephthalate (PET), polyacrylic acid-polypyrene methanol (PAA-PM), polyamide (PA), silk/PEO, polyvinylphenol (PVP), polyvinylchloride (PVC), cellulose acetate (CA), PAA-PM/PU, polyvinyl alcohol (PVA)/silica, polyacrylamide (PAAm), poly(lactic-co-glycolic acid) (PLGA), polycarprolactone (PCL), poly(2-hydroxyethyl methacrylate) (HEMA), poly (vinylidene difluoride) (PVDF), PVDF/PMMA, polyether imide (PEI), polyethylene glycol (PEG), poy(ferrocenyldimethylsilane) (PFDMS), Nylon6/montmorillonite (Mt), poly(ethylene-co-vinyl alcohol), polyacrylnitrile (PAN)/$TiO_2$, polycaprolactone (PCL)/metal, polyvinyl porrolidone, polymetha-phenylene isophthalamide, polyethylene (PE), polypropylene (PP), nylon-12, polyethylene terephthalate (PET), polyethylene naphthalate (PEN), polyether sulfone (PES), polyvinyl butyral (PVB), or PET/PEN In still yet another embodiment of the method of the present invention contemplates that the polymer is selected from PMMA, PVDF, or a blend of PMMA and PVDF. In still yet another embodiment the present invention contemplates that the blend of PMMA and PVDF has the weight ratio between PMMA to PVDF of 1:99 to 99:1. In still yet another embodiment the present invention contemplates that the weight ratio of PMMA to PVDF is 10:90, 15:85, 20:80, 25:75, 30:70, 35:65, 40:60, 45:55, 50:50, 55:45, 60:40, 65:35, 70:30, 75:25, 80:20, 85:15, or 90:10.

In still yet another embodiment of the method of the present invention contemplates that the polymer preparation comprises PMMA and/or PVDF dissolved in a solvent selected from N,N-Dimethylacetamide (DMAC), N,N-Dimethylformamide (DMF), or a mixture thereof. In still yet another embodiment the present invention contemplates that the solvent further comprises acetone.

In still yet another embodiment of the method of the present invention contemplates that the polymer preparation comprises about 5% to 20% by weight of PMMA, PVDF, or a blend thereof in the polymer solution.

In still yet another embodiment of the method of the present invention contemplates that the polymer preparation comprises 15%, 16%, 17%, 18%, 19%, or 20% by weight of the blend of PMMA and PVDF, wherein the ratio of PMMA to PVDF in the blend is 75:25, 60:40, or 50:50, and wherein PMMA and/or PVDF is dissolved in a solvent selected from DMAC, DME, or a mixture thereof. In still yet another embodiment the present invention contemplates that the solvent further comprises acetone.

In still yet another embodiment of the method of the present invention contemplates that the viscosity of the polymer preparation comprising PMMA and/or PVDF in the solvent of DMAC and/or DMF and/or acetone is between: 200 centipoise (cP) to 5000 cP, 300 cP to 2000 cP, 400 cP to 1000 cP, 500 cP to 900 cP, 600 cP to 800 cP, or 700 cP to 800 cP.

In still yet another embodiment of the method of the present invention contemplates that the non-porous polymer film substrate comprises polyethylene with carbon, polyimide with carbon, low-density polyethylene (LDPE) with an anti-static additive, polypropylene with anti-static additive, acrylonitrile butadiene styrene with anti-static additive, nylon, static dissipative high molecular weight polyethylene (UHMWPE), polypropylene spun-bound with antistatic treatment, LDPE, polycarbonate, UHMWPE, polyvinyl chloride, polyethylene terephthalate (PET), PMMA, PVDF, or PMMA/PVDF.

In still yet another embodiment of the method of the present invention contemplates that the non-porous polymer film substrate has a bulk electrical resistivity of $10^8$ Ω-cm to $10^{12}$ Ω-cm.

In still yet another embodiment of the method of the present invention contemplates that the nanofibers are electrospun at a voltage between: 30 to 120 kV, 40 to 110 kV, 50 to 100 kV. 60 to 90 kV, or 70 to 80 kV.

In still yet another embodiment of the method of the present invention contemplates that the method further comprises having a distance between electrodes from 150 to 300 mm, 160 to 290 mm, 170 to 280 mm, 180 to 270 mm, 190 to 260 mm, 200 to 250 mm, 210 to 240 mm, or 220 to 230 mm.

In still yet another embodiment of the method of the present invention contemplates that the method further comprises having a dispensing device orifice of between 0.4 to 0.8 mm, 0.45 to 0.75 mm, 0.5 to 0.6 mm, 0.55 to 0.65 mm, or 0.6 mm.

In still yet another embodiment of the method of the present invention contemplates that the method further comprises having a carriage speed from 50 to 150 mm/sec, 60 to 140 mm/sec, 70 to 130 mm/sec, 80 to 120 mm/sec, 90 to 110 mm/sec, or 100 mm/sec.

In still yet another embodiment of the method of the present invention contemplates that the method further comprises having a wire speed from 1 to 5 mm/sec, 2 to 4 mm/sec, or 3 mm/sec.

In still yet another embodiment of the method of the present invention contemplates that the method further comprises having a speed of air-in from 60 $m^3$/hr to 120 $m^3$/hr, 70 $m^3$/hr to 110 $m^3$/hr, 80 $m^3$/hr to 100 $m^3$/hr, or 90 $m^3$/hr and the speed of air-out is between 100 $m^3$/hr to 140 $m^3$/hr, 110 $m^3$/hr to 130 $m^3$/hr, or 120 $m^3$/hr.

In still yet another embodiment of the method of the present invention contemplates that the method further comprises having a temperature in the spinning chamber from 25 to 50° C., 30 to 45° C., 35° C. to 40° C., or 40 to 45° C.

In still yet another embodiment of the method of the present invention contemplates that the method further comprises having a relative humidity in the spinning chamber from 10 to 35%, 15 to 30%, or 20% to 25%.

In still yet another embodiment of the method of the present invention contemplates that the method further comprises having a dew point in the spinning chamber from 2.0° C. to 6.0° C., 2.2° ° C. to 5.8° C., 2.4° C. to 5.6° C., 2.6° C. to 5.4° C., 2.8 to 5.2° C., 3.0° ° C. to 5.0° C., 3.2° C. to 4.8° C., 3.4° C. to 4.6° C., 3.6° C. to 4.4° C., or 3.8° C. to 4.2° C.

In still yet another embodiment of the method of the present invention contemplates that the method further comprises having a per wire line speed from 0.5 cm/min to 5.0 cm/min, 1.0 cm/min to 4.5 cm/min, 1.5 cm/min to 4.0 cm/min, 2.0 cm/min to 3.5 cm/min, or 2.5 cm/min to 3.0 cm/min.

In still yet another embodiment of the method of the present invention contemplates that the electrospinning is needle-electrospinning or needleless electrospinning.

BRIEF DESCRIPTION OF THE DRAWINGS

FIGS. 3.1 and 3.2 show scanning electron micrographs (SEM) of air-cast Hi-Flow™ Plus Nitrocellulose membrane. FIG. 3.1: The top surface at 1000×. FIG. 3.2: The cryo-fractured cross-section at 600×.

FIG. 22 shows a plot of fiber mat thickness produced on a selection of the films (1-5, 5b-8b, 12, 17) from Table 5 with increasing bulk resistivity generated under the same electrospinning conditions over the same spinning time of 10 minutes and film width of 40 cm. This illustrates that there is an optimal range of bulk electrical resistivity for peak fiber mat thickness or productivity.

FIGS. 26.1 and 26.2 show SEM images of electrospun fibers. FIG. 26.1 shows a SEM image of electrospun fibers on the air side. FIG. 26.2 shows a SEM image of electrospun fibers on the LDPE side. The electrospun fibers are produced from 17% w/v PMMA5 (BS572):PVDF6 (Kynar® 761) in DMAC onto a moving web of LDPE film.

FIGS. 28.1 to 28.3 show SEM images of the electrospun sample in FIG. 27 at 3 different dew points. FIG. 28.1 shows a SEM image of the electrospun sample in FIG. 27 at a dew point of 11.8° C. FIG. 28.2 shows a SEM image of the electrospun sample in FIG. 27 at a dew point of 3.2° C. FIG. 28.3 shows a SEM image of the electrospun sample in FIG. 27 at a dew point of 2.6° C.

(BS572):PVDF6 (Kynar® 761) at two known % relative humidities produced by the same electrospinning parameters.

Figure 31:
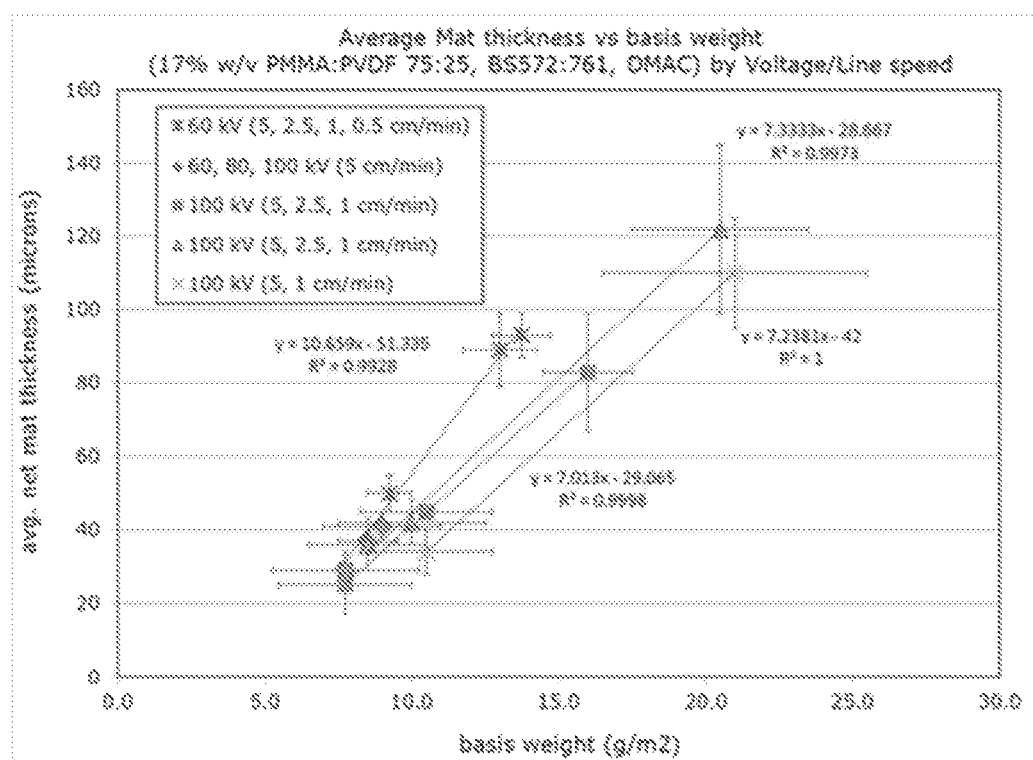

FIG. 31 shows the linearity of average net electrospun fiber mat thickness against basis weight for the several conditions of voltage and line speeds in Table 6.

Figure 32:
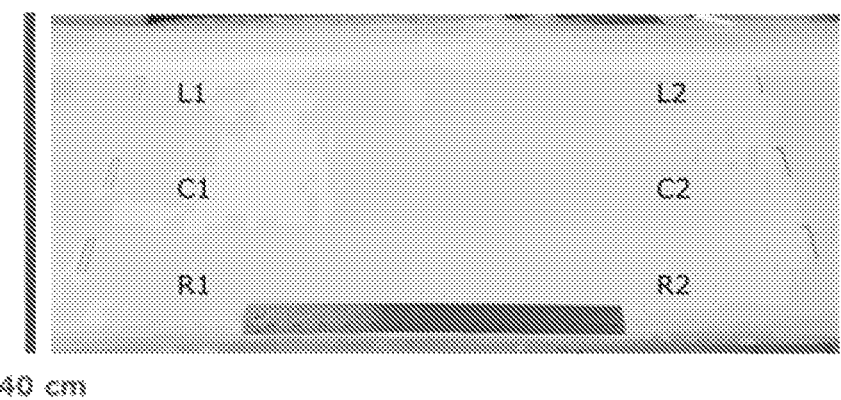

FIG. 32 shows an image of the sampling area (60×40 cm) and locations cross and down-web used to measure electrospun fiber mat thickness to determine productivity and uniformity.

FIG. 33.1 shows a plot of average net mat thickness and basis weight for the solution and constant 60 kV voltage against 1/line speed electrospinning experiments detailed in Table 6.

FIG. 33.2 shows a plot of the average net mat thickness of the aforementioned experiment (FIG. 33.1) at constant 60 kV voltage vs 1/line speed collected on a moving web of 100 μm thick LDPE film (#12 in Table 5) overlayed with mats electrospun under identical conditions with the exception of 100 kV on a moving web of Permastat LDPE PE700AS film (#7b in Table 5).

Figure 34:
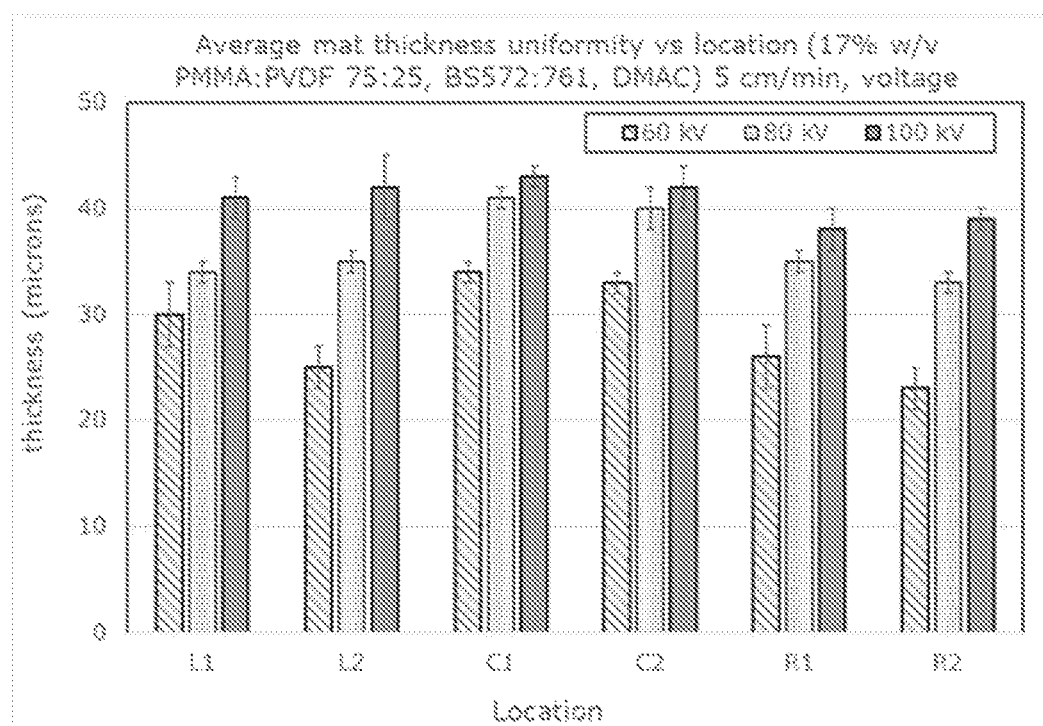

FIG. 34 shows a plot of thickness and uniformity of the sample locations detailed in FIG. 32 for the solution and constant line speed against voltage electrospinning experiments detailed in Table 6.

Figure 35:
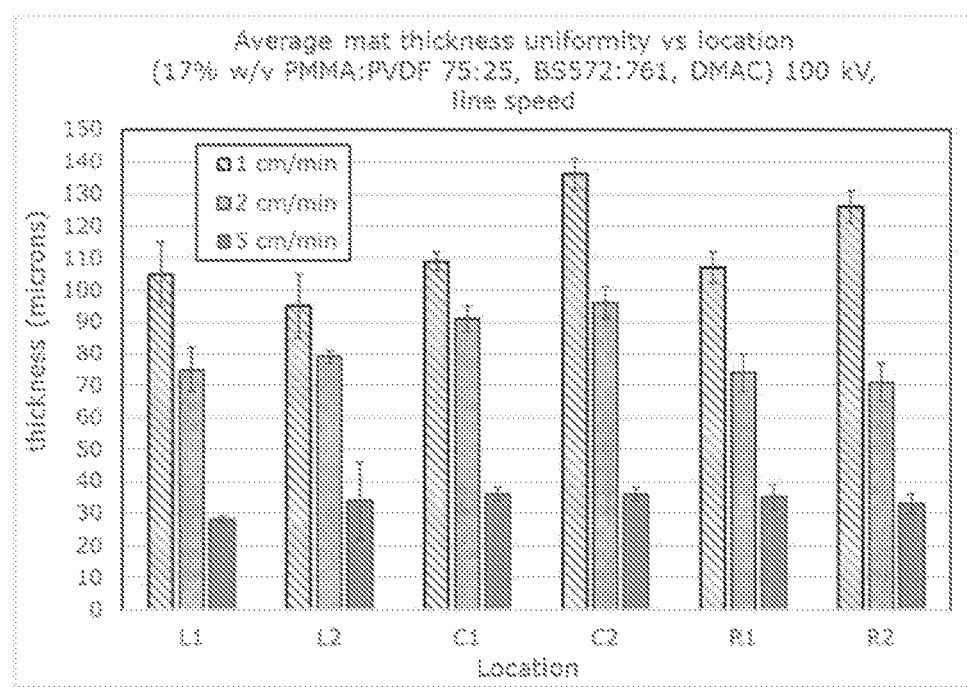

FIG. 35 shows a plot of thickness and uniformity of the sample locations detailed in FIG. 32 for the solution in Table 6 at 100 kV against line speed.

FIGS. 36.1 to 36.3 show SEM images of the experiments in FIG. 35. FIG. 36.1 shows an SEM cross-section image (600× magnification) of the fiber mat produced in FIG. 35 at 1.0 cm/min line speed. FIG. 36.2 shows an SEM cross-section image (2000× magnification) of the fiber mat produced in FIG. 35 at 2.0 cm/min line speed. FIG. 36.3 shows an SEM cross-section image (2000× magnification) of the fiber mat produced in FIG. 35 at 5.0 cm/min line speed.

Figure 37:
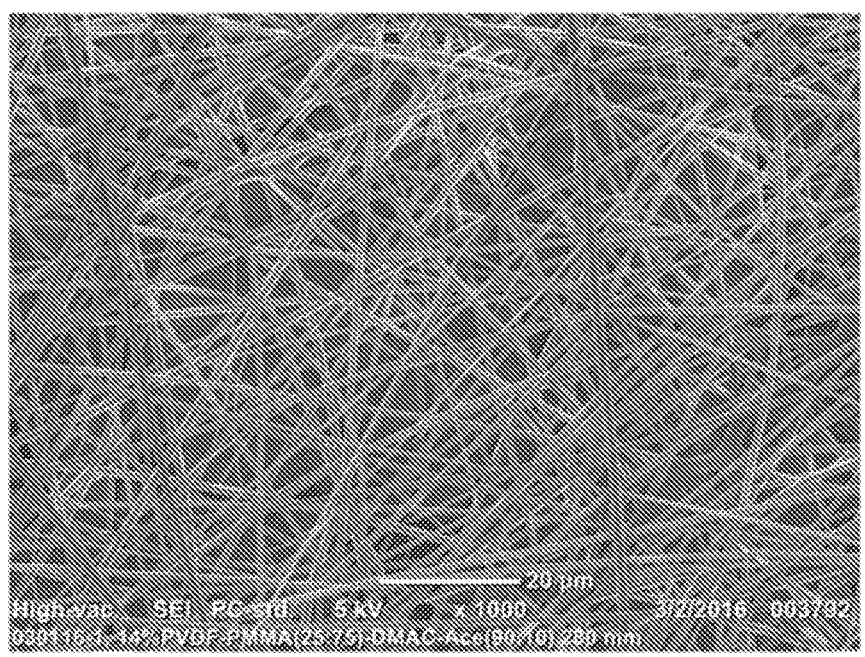

FIG. 37 shows an SEM image of 733±263 nm fibers electrospun at 30 kV from 14% w/v PMMA5 (BS572):PVDF6 (Kynar® 761) at a ratio of 75:25 in 90:10 DMAC:acetone at temperature of 35° C. and relative humidity of 45%.

FIGS. 38.1 and 38.2 show plots of pore size distribution versus average diameter for air-cast nitrocellulose and an electrospun non-woven fiber mat. FIG. 38.1 shows a plot of pore size distribution against average diameter of an unbacked nitrocellulose membrane (Hi-Flow™ Plus 180 UB, MilliporeSigma) produced by air-casting. FIG. 38.2 shows a plot of pore size distribution versus average diameter of an electrospun non-woven fiber mat with average fiber diameter of about 700 nm electrospun from a 17% w/v solution of PMMA5 (BS572):PVDF6 (Kynar® 761) at a ratio of 75:25 in DMAC.

Figure 39:
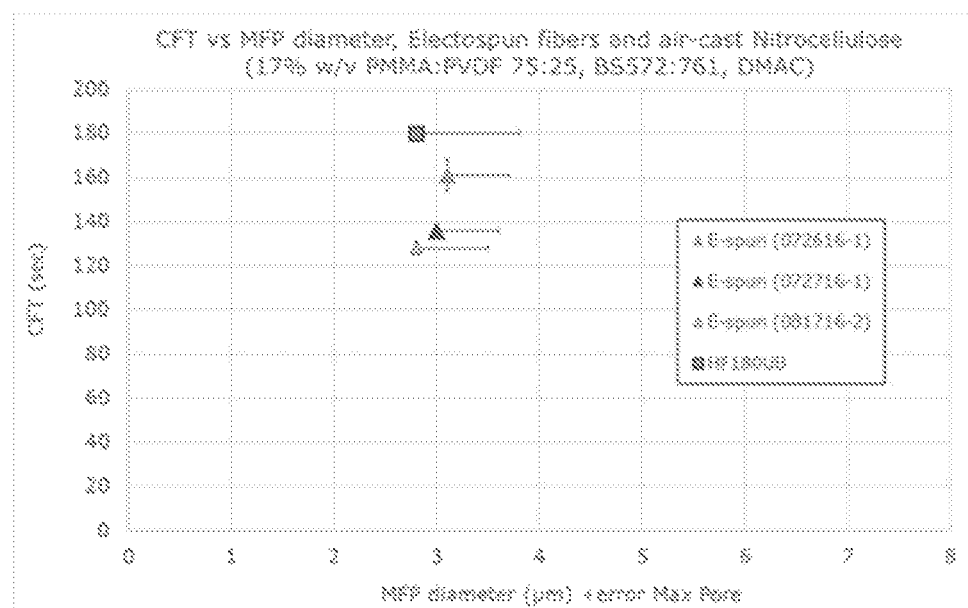

FIG. 39 shows a plot of CFT against MFP with the positive error bar extended to show the maximum flow pore diameter for air-cast nitrocellulose and electrospun non-woven fiber mats having CFTs of about 135 to 180 seconds.

Figure 40:
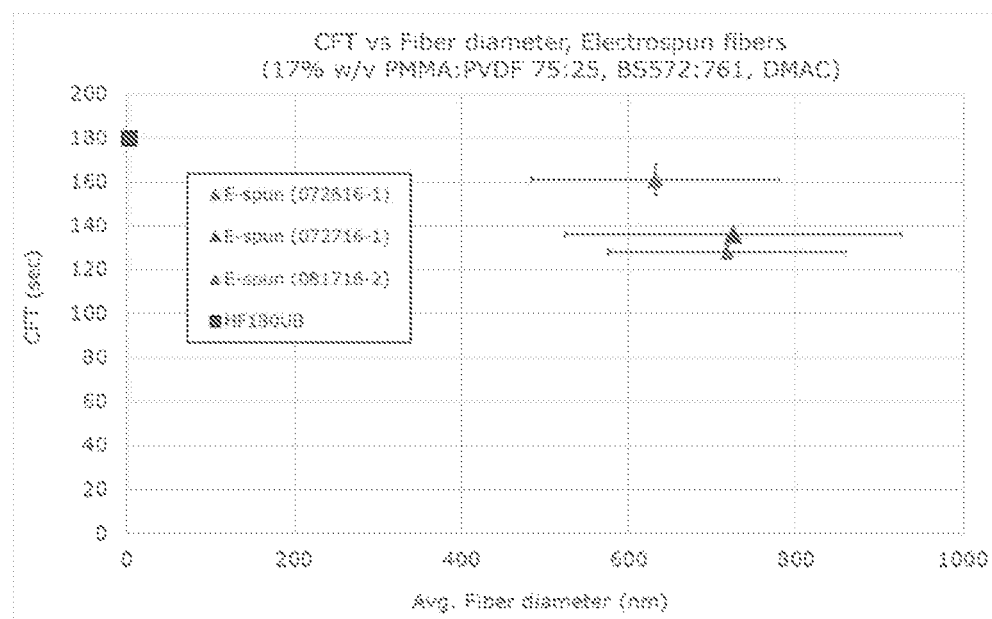

FIG. 40 shows a plot of CFT against average fiber diameter to show the relationship of CFT to average fiber diameter.

Figure 41:
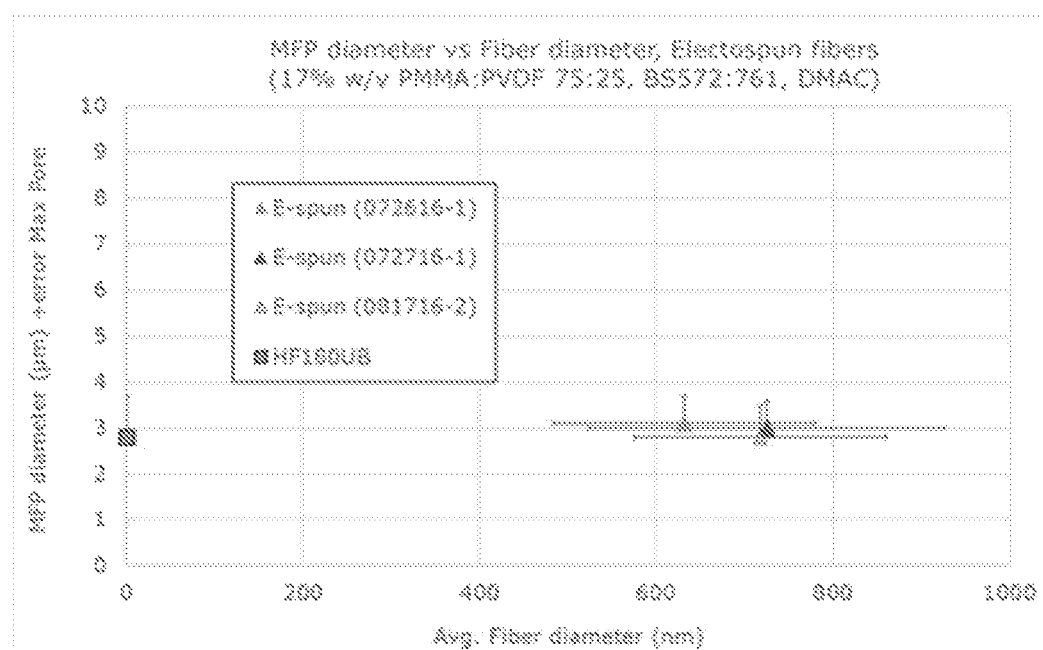

FIG. 41 shows a plot of MFP with the positive error bar extended to show the maximum flow pore diameter versus average fiber diameter to show the relationship of MFP to average fiber diameter of the electrospun fiber mat membranes.

Figure 42:
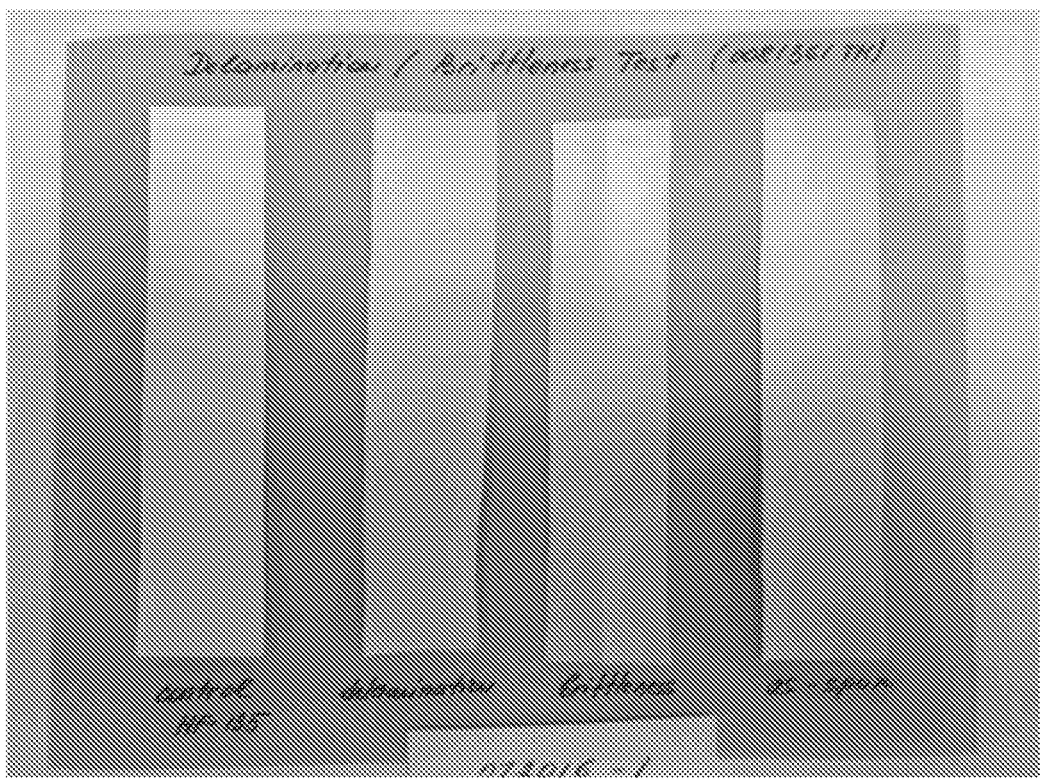

FIG. 42 shows four test strips tested for delamination and brittleness. From left-to-right the samples show that an air-cast nitrocellulose (Hi-Flow™ Plus 135) and electrospun non-woven fiber mat membrane collected on a corona treated side of LDPE film (delamination, brittlenesss, and as spun) all pass the delamination and brittleness testing.

FIGS. 43.1 and 43.2 show images of delamination and shrinkage testing of electrospun fiber mats with average fiber diameters of about 700 nm on LDPE film post IPA/water wetting, surfactant treatment, and air drying. FIG. 43.1 shows an image of duplicate 56 mm circular die cut electrospun membrane with average fiber diameters of about 700 nm spun on corona treated side of LDPE after IPA/water wetting, surfactant treatment, and air drying to show good adhesion and no shrinkage/delamination of the fiber mat. FIG. 43.2 shows an image of duplicate rectangular cut electrospun membranes with average fiber diameters of about 700 nm spun onto the non-corona treated side of LDPE to allow for delamination after IPA/water wetting, surfactant treatment, and air drying. The figures show the shrinkage is minimal post drying even when intentionally allowed to delaminate from the film substrate.

FIG. 44.1 shows a SEM image cross-section of electrospun non-woven fibers directly spun onto a conductive polyimide film (Kapton® XC, DuPont) side containing a pressure sensitive acrylic adhesive as a method to improve adhesion.

FIGS. 44.2 and 44.3 are an image and SEM cross-section image of an electrospun non-woven fiber mat that was directly spun onto GL-187® adhesive from Lohmann Corporation (Orange, VA) that was coated onto Permastat LDPE PE700AS film (#7b in Table 5).

FIGS. 44.4 and 44.5 are an image and SEM cross-section image of an electrospun non-woven fiber mat that was electrospun onto and transferred from the non-adhesive and non-corona treated side of the Permastat LDPE PE700AS film (#7b in Table 5) onto GL-187® adhesive from Lohmann Corporation (Orange, VA) that was coated onto Permastat LDPE PE700AS film (#7b in Table 5).

FIGS. 45.1 to 45.2 show images of electrospun fiber mats on the non-adhesive and adhesive sides of Kapton® XC film, post IPA/water wetting, surfactant treatment, and air drying. FIG. 45.1 shows an image of replicate samples of electrospun fibers spun on the non-adhesive side of Kapton® XC film, where the fiber mat delaminates post IPA/water wetting, surfactant treatment, and air drying. FIG. 45.2 shows an image of replicate samples of electrospun fibers spun on the acrylic adhesive side of Kapton® XC film, where the fiber mat remains well bonded post IPA/water wetting, surfactant treatment, and air drying.

Figure 46:
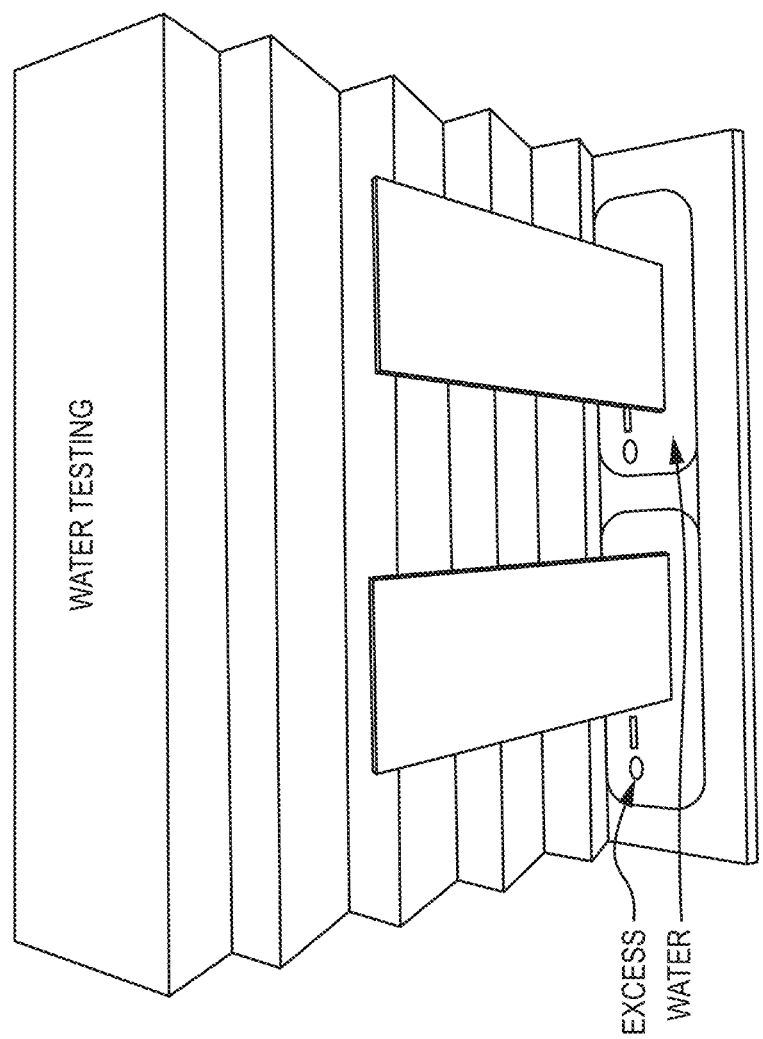

FIG. 46 shows an image of a custom test stand used to measure CFT and bead mobility.

FIGS. 47.1 and 47.2 show images of membranes post the latex detector bead mobility test. FIG. 47.1 shows an image of duplicate electrospun membranes with an average fiber diameter of 632±212 nm and about 200 second CFT that pass the bead mobility test, along with a passing Hi-Flow™ Plus135 control. FIG. 47.2 shows an image of duplicate electrospun membranes with an average fiber diameter of 432±95 nm and about 300 second CFT that fails the bead mobility test, with obvious visual failure of the beads to travel the full 4 cm.

FIGS. 48.1 and 48.2 show SEM image cross-sections of Hi-Flow™ Plus 135 and a latex bead passing electrospun fiber mat sample with 400 nm beads visible in the cross-section. FIG. 48.1 shows a SEM image cross-section of Hi-Flow™ Plus 135 sample that passes the latex bead mobility test with beads visible in the cross-section. FIG. 48.2 shows a SEM image cross-section of an electrospun fiber sample that passes the latex bead mobility test with beads visible in the cross-section.

Figure 49:
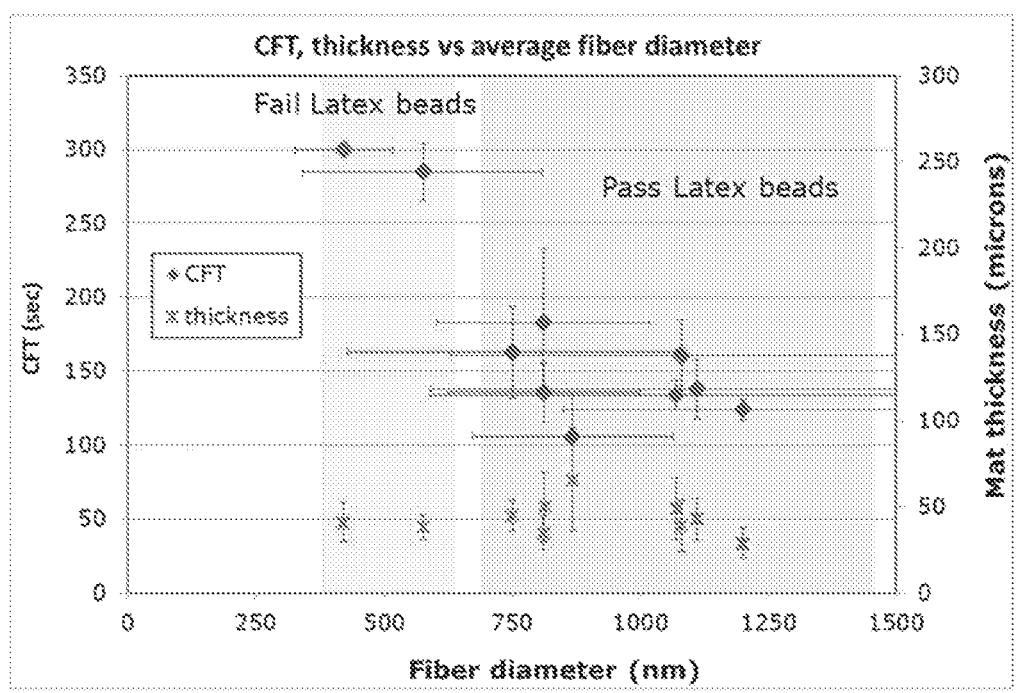

FIG. 49 shows a plot of CFT versus average fiber diameter of electrospun non-woven fiber mat membranes at similar net mat thicknesses. Shaded regions indicate whether the membranes passed/failed the latex bead mobility test.

Figure 50:
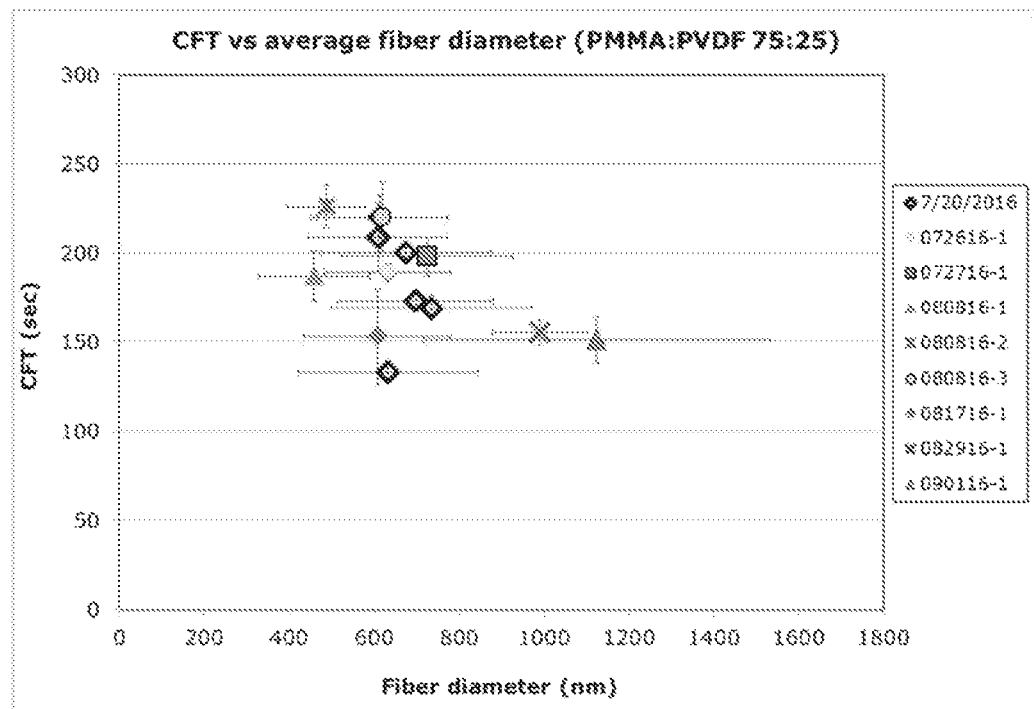

FIG. 50 shows a plot of additional samples measured for CFT versus average fiber diameter of electrospun non-woven fiber mat membranes that were electrospun on a moving web of LDPE. The solution was 17% w/v of PMMA5 (BS572):PVDF6 (Kynar® 761) at ratio of 75:25 in DMAC where the different fiber diameters were the result of uncontrolled dew point.

Figure 51:
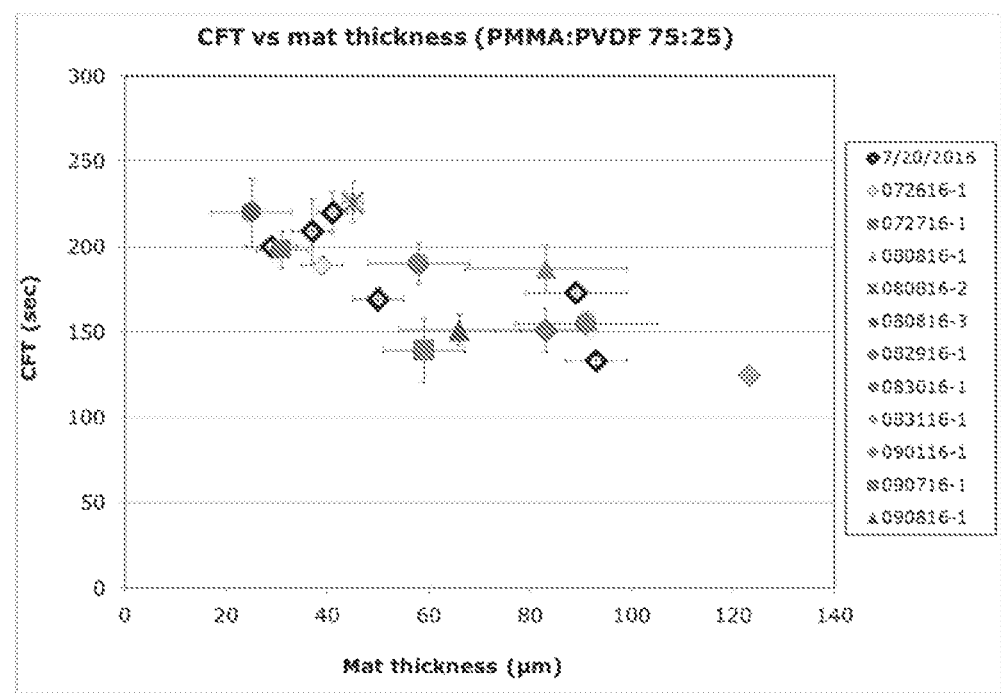

FIG. 51 shows a plot of CFT versus average net fiber mat thickness for electrospun non-woven fiber mats having about 700 nm average fiber diameters.

FIGS. 52.1 and 52.2 show the correlation between CFT, relative humidity, and mat thickness. FIG. 52.1 shows a plot of CFT versus relative humidity % for electrospun fiber membranes of different mat thicknesses and the Hi-Flow™ Plus 135 nitrocellulose control. FIG. 52.2 shows a plot of CFT against membrane mat thickness at different equilibrated relative humidity %.

Figure 53:
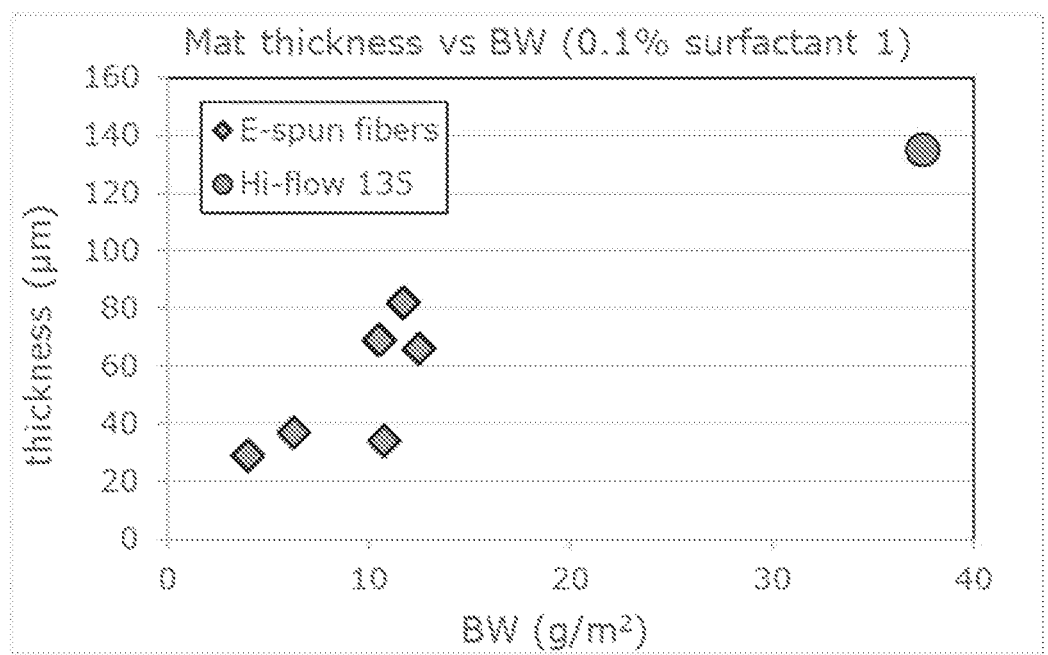

FIG. 53 shows a plot of mat thickness against basis weight for electrospun fibers PMMA:PVDF 75:25 having about 700 nm average fiber diameters and Hi-Flow™ Plus 135 control.

FIGS. 54.1 and 54.2 show plots of CFT versus wt % surfactant treatment concentration for Surfactant 1 and Surfactant 2 for electrospun non-woven fiber mats of different thicknesses. FIG. 54.1 shows a plot of CFT against wt % Surfactant 1 treatment. FIG. 54.2 shows a plot of CFT against wt % Surfactant 2 treatment.

Figure 55:
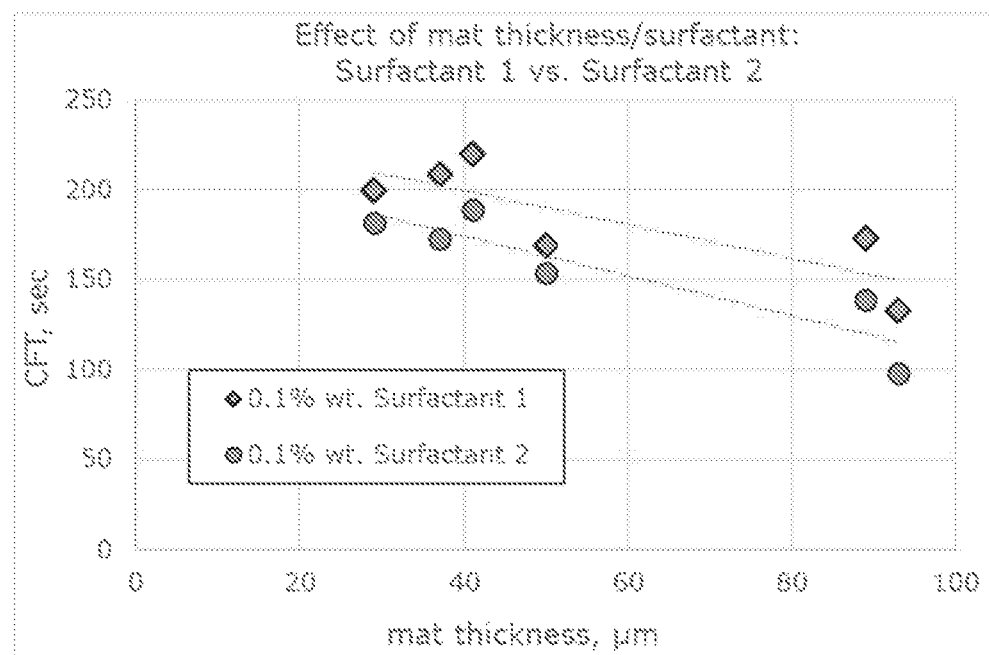

FIG. 55 shows a plot of CFT against average net fiber mat thickness for treatments of 0.1% wt Surfactant 1 and Surfactant 2.

FIGS. 56.1 and 56.2 shows plots of IgG binding against wt % surfactant treatment concentrations for electrospun non-woven fiber mats of different thicknesses. FIG. 56.1 shows a plot of IgG binding versus wt % Surfactant 1 treatment concentration. FIG. 56.2 shows a plot of IgG binding against wt % Surfactant 2 treatment concentration.

Figure 57:
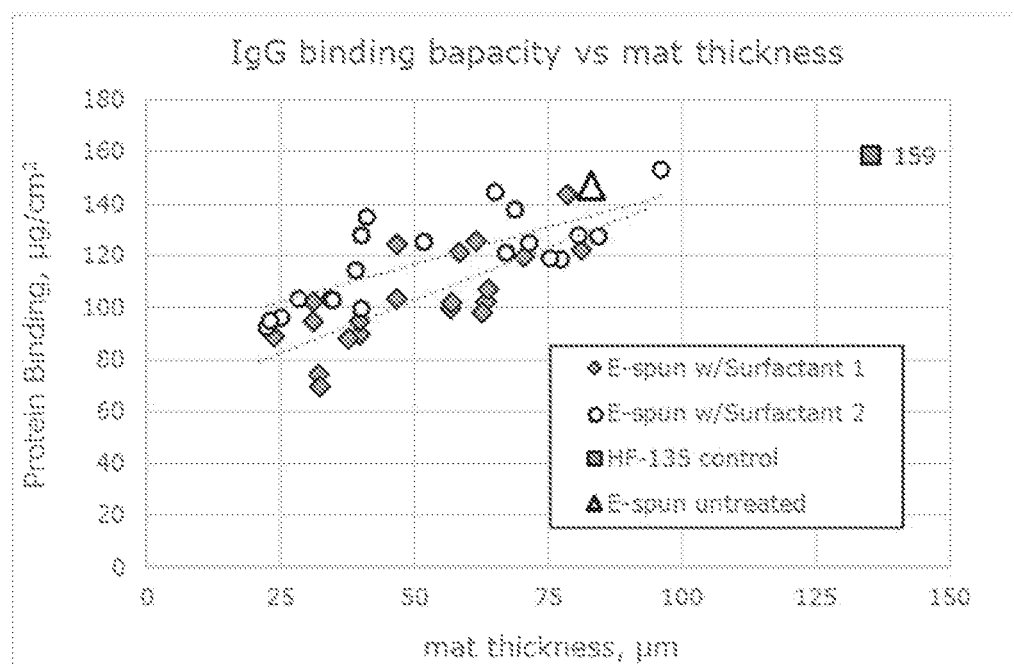

FIG. 57 shows a plot of IgG binding against average net fiber mat thicknesses of ~700 nm PMMA:PVDF (75:25) fibers treated with various wt % of Surfactant 1 and Surfactant 2 and Hi-Flow™ Plus 135 control.

FIG. 58.1 shows an image of the protein striping quality for samples from Table 9.1.

FIG. 58.2 shows an image of protein striping samples from left to right of a Hi-Flow™ Plus 135 control and replicate samples of electrospun non-woven fiber mat membranes PMMA:PVDF (70:30) treated with 0.07 and 0.09% surfactant 2 (Example 20) for protein (IgG) solution conditions detailed in Table 9.2.

FIG. 58.3 shows an image of protein striping samples from left to right of duplicate Hi-Flow™ Plus 135 controls and replicate samples of electrospun non-woven fiber mat membranes PMMA:PVDF (70:30) treated with 0.07 and 0.09% surfactant 2 (Example 20) for protein (IgG) solution conditions detailed in Table 9.3.

Figure 59:
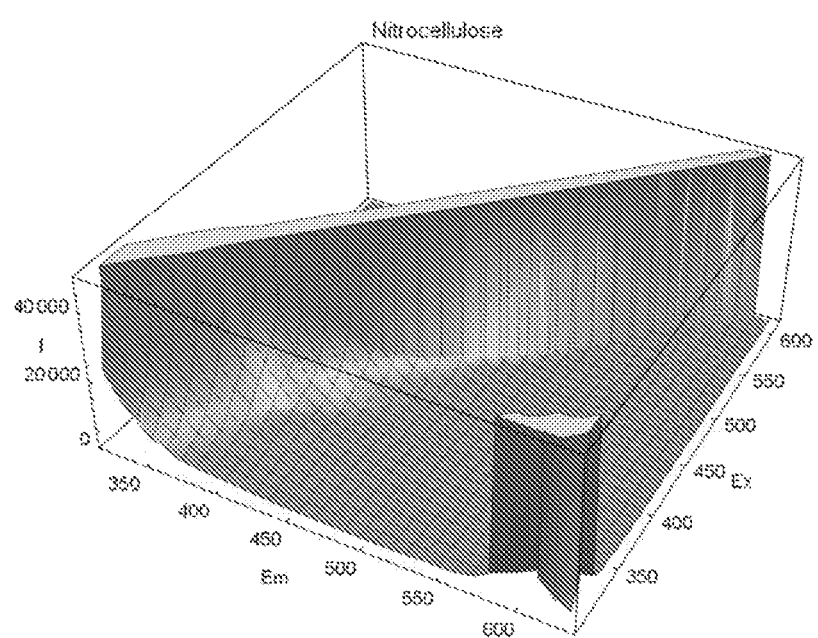

FIG. 59 shows fluorescence spectrum of intensity versus excitation (300-610 nm) and emission wavelengths (320-630 nm) for the Hi-Flow™ Plus 135 nitrocellulose control membrane.

FIGS. 60.1 and 60.2 show fluorescence spectra of intensity versus excitation (300-610 nm) and emission wavelengths (320-630 nm) for the two ratios of [PMMA:PVDF membrane—Hi-Flow™ Plus 135 nitrocellulose control membrane] to show the electrospun non-woven fiber mats have less fluorescence than the control nitrocellulose. FIG. 60.1 shows fluorescence spectrum of intensity against excitation (300-610 nm) and emission wavelengths (320-630 nm) for the [PMMA:PVDF (75:25) membrane—Hi-Flow™ Plus 135 nitrocellulose control membrane]. FIG. 60.2 shows fluorescence spectrum of intensity against excitation (300-610 nm) and emission wavelengths (320-630 nm) for the [PMMA:PVDF (50:50) membrane—Hi-Flow™ Plus 135 nitrocellulose control membrane].

Figure 61:
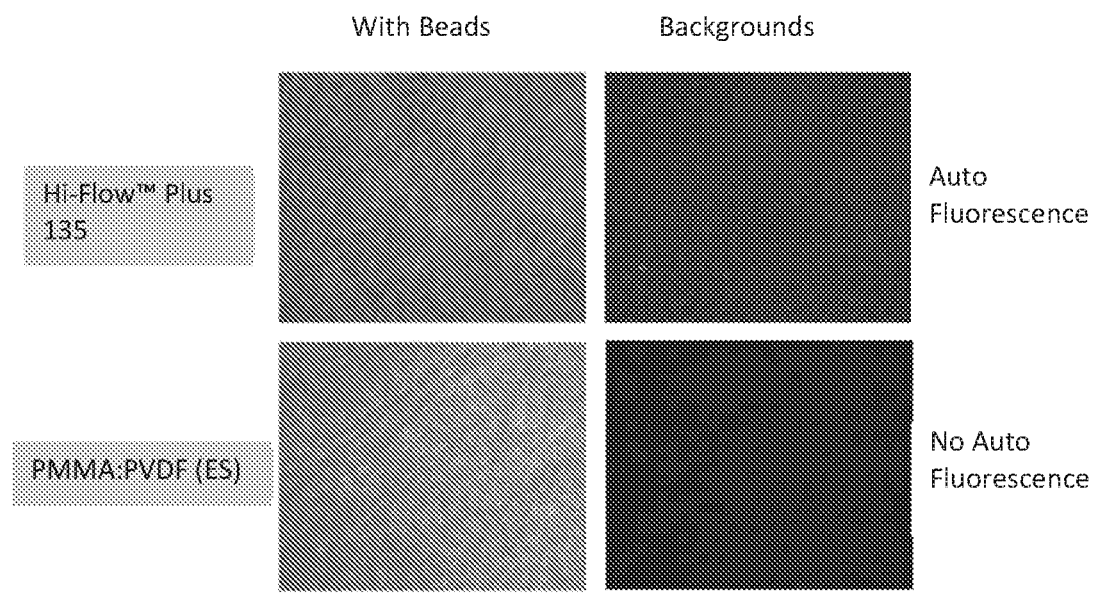

FIG. 61 shows fluorescence microscope images of Hi-Flow™ Plus 135 nitrocellulose control membrane and a PMMA:PVDF (75:25) membrane with and without fluorescently labelled beads at 200× magnification, FITC mode, and constant laser excitation intensity.

Figure 62:
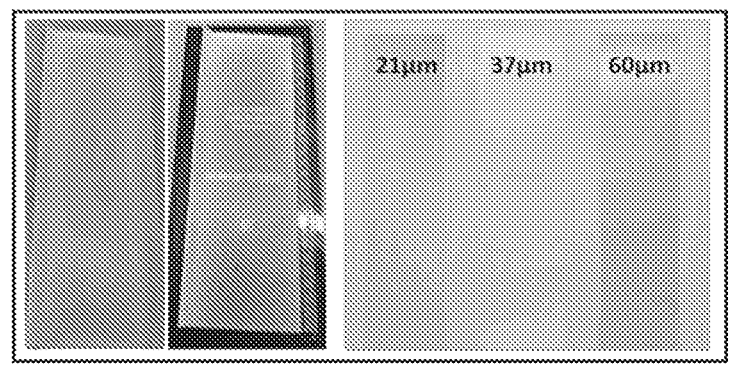

FIG. 62 shows images of electrospun PMMA membranes produced by an exemplary method provided herein having thicknesses of 21 □m, 37 □m and 60 □m.

Figure 63:
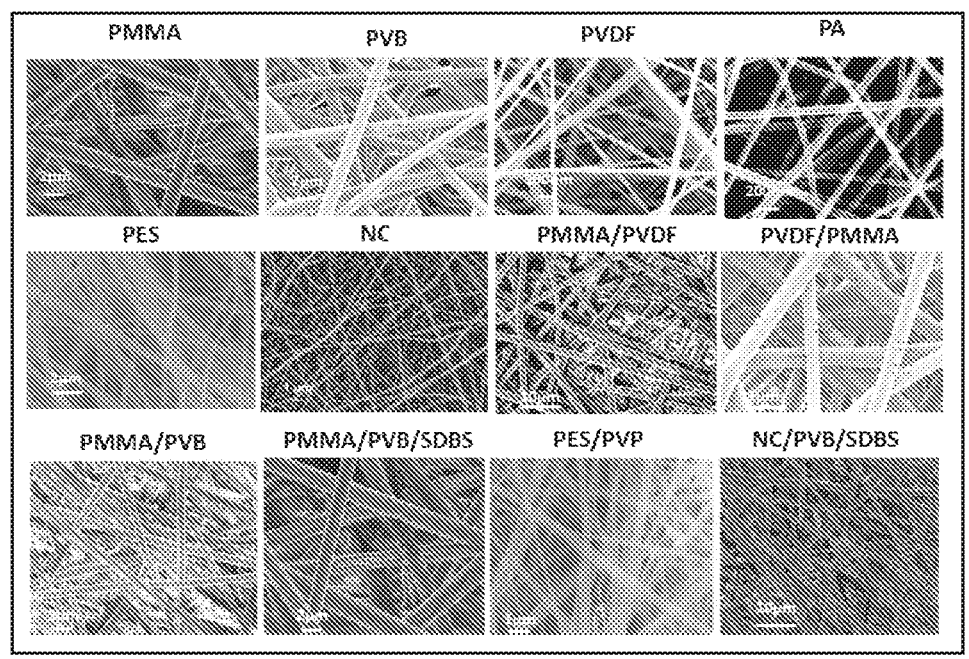

FIG. 63 shows SEMs of electrospun membranes produced by the methods provided herein. The membranes are produced using the following polymers and polymer blends: PMMA, PVB, PVDF, PA, PES, NC, PMMA/PVDF, PVDF/PMMA, PMMA/PVB, PMMA/PVB/SDBS, PES/PVP and NC/PVB/SDBS. The image illustrates the porosity, pore size, and surface morphologies of the electropun membranes. SEM of high magnification shows electrospun membrane with uniform beads-free fibers.

Figure 64:
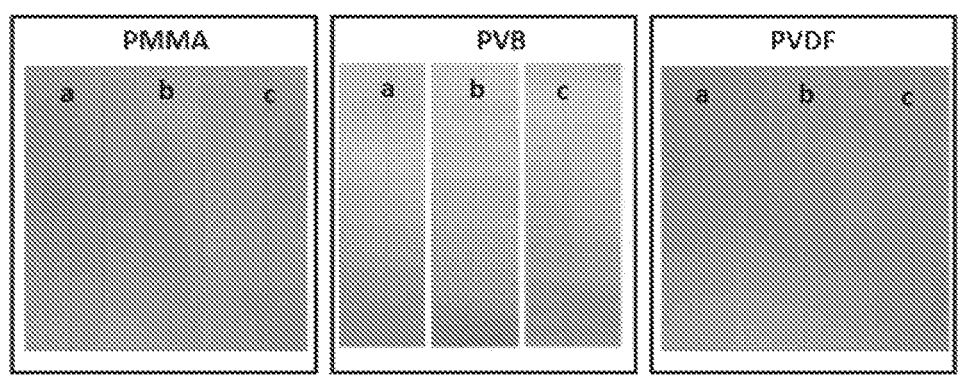

FIG. 64 shows protein binding to the electrospun membranes produced by the methods provided herein. The membranes were electrospun using PMMA, PVB, and PVDF.

Figure 65:
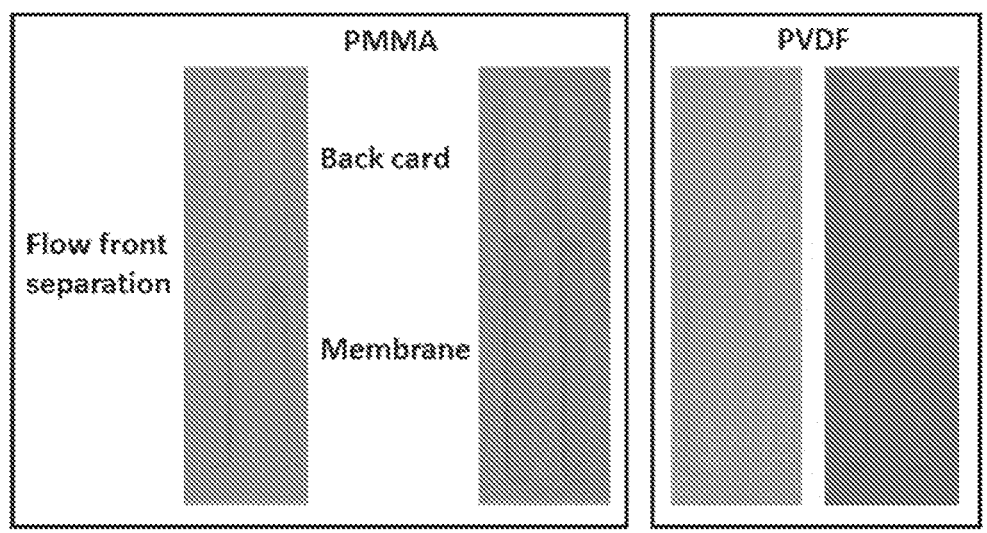

FIG. 65 shows gold nanoparticle mobility studies of the electrospun membranes produced by an exemplary method provided herein.

Figure 66:
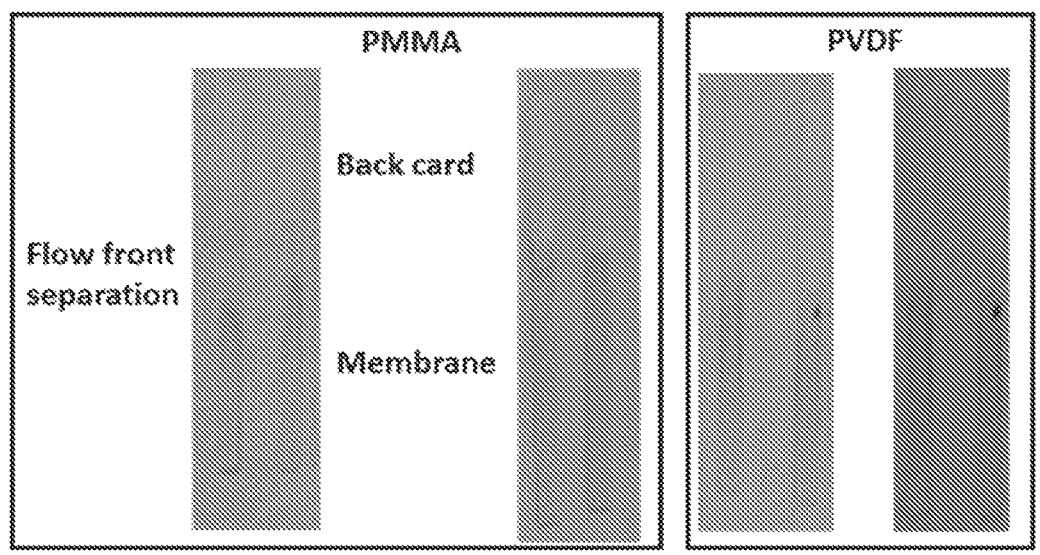

FIG. 66 shows latex mobility studies of the electrospun membranes produced by an exemplary method provided herein. Bead testing mobility of larger 0.4 μm diameter latex beads was evaluated with electropun membranes. Membranes show no flow front separation between the liquid and the latex beads.

Figure 67:
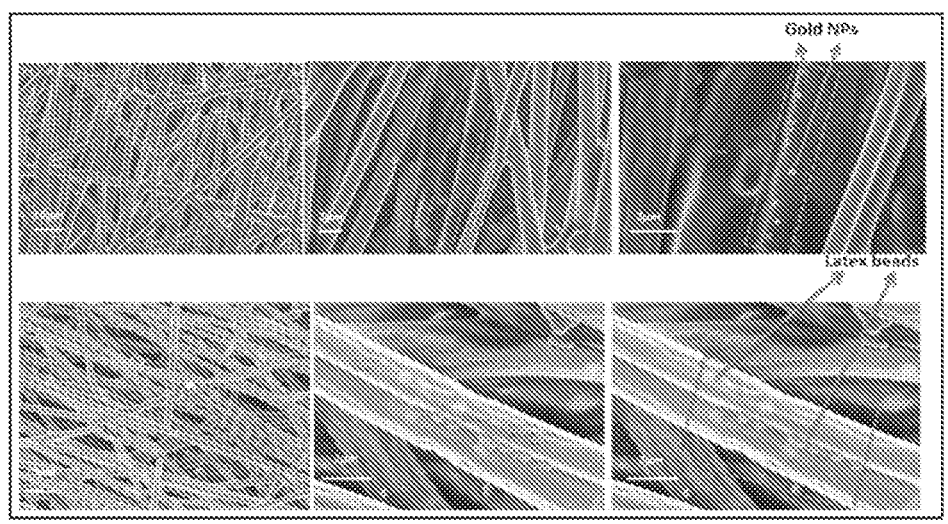

FIG. 67 shows an SEM of PMMA membrane produced by an exemplary method provided herein after gold nanoparticles and latex bead mobility studies. These particles flow along sides of the fibers through interconnected pores without any flow front separation as shown in high magnification SEMs.

Figure 68:
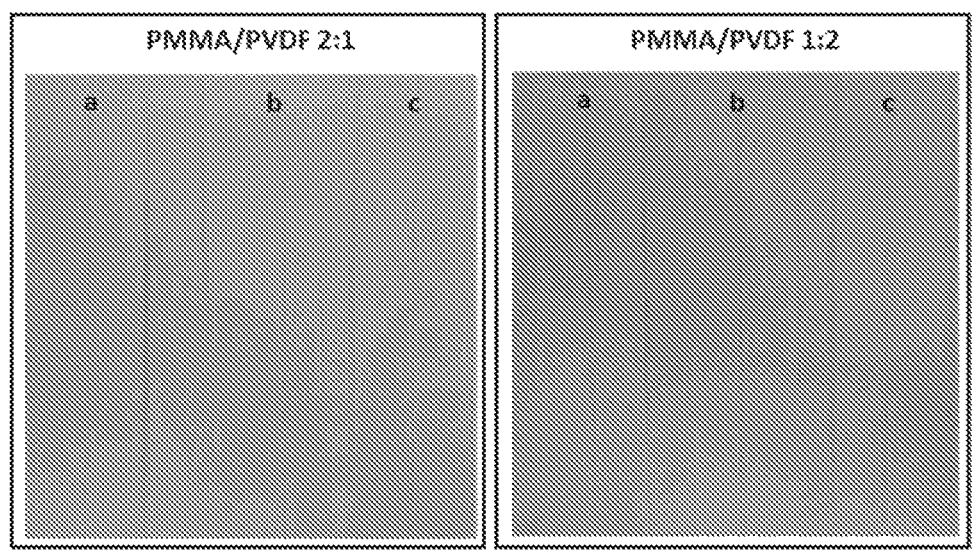

FIG. 68 shows the protein binding of two PMMA/PVDF blend electrospun membranes with differing PMMA/PVDF ratios produced by an exemplary method provided herein. Results show that proteins can be found on the electrospun membranes and its potential properties for lateral application.

Figure 69:
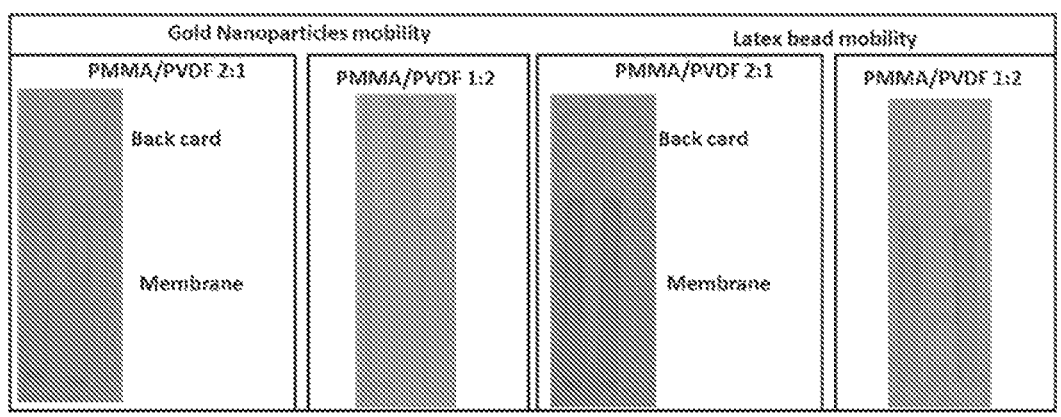

FIG. 69 shows gold nanoparticle mobility studies of two PMMA/PVDF electrospun membranes having different PMMA/PVDF ratios produced by an exemplary method provided herein.

Figure 70:
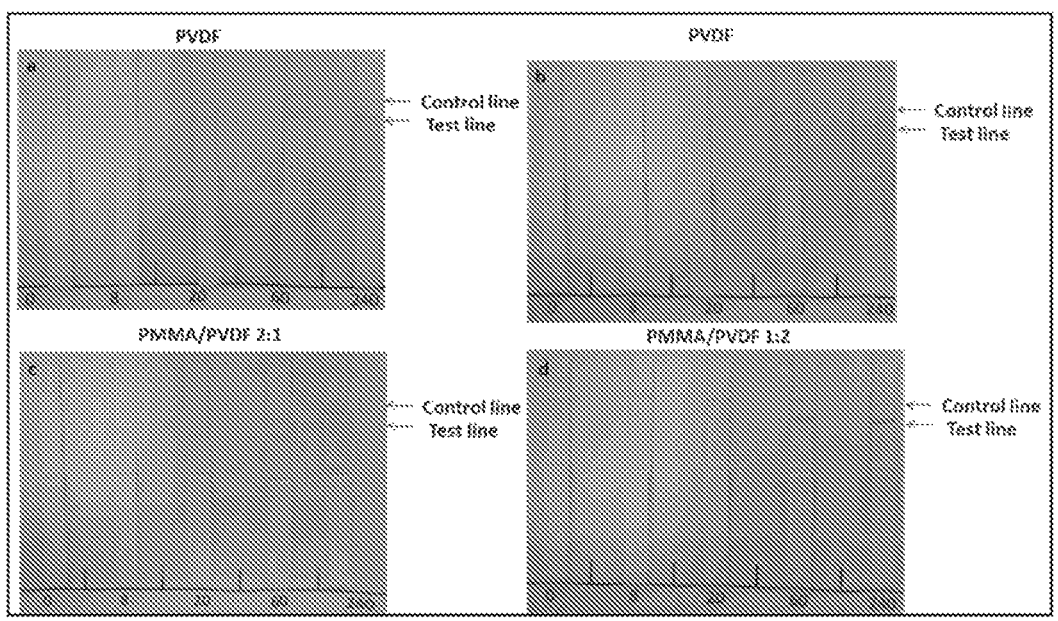

FIG. 70 shows an Hepatitis B assay of (a) PVDF membrane with a thickness 85 (b) PVDF membrane with a thickness 119 μm, (c) 2:1 PMMA/PVDF blend membrane with 68 μm, and (d) 1:2 PMMA/PVDF blend membrane with 65 μm.

FIGS. 71.1 and 71.2 shows passing test results for complete Hepatitis B surface antigen (HBsAg) lateral flow tests on Electrospun non-woven fiber mat membranes (71.1) and Air-cast nitrocellulose (71.2).

FIGS. 72.1 and 72.2 shows passing tests for the hCG (Human chorionic gonadotropin hormone) functionality test to detect pregnancy on Electrospun non-woven fiber mat membranes (72.1) and Air-cast nitrocellulose (72.2).

DETAILED DESCRIPTION

General

A lateral flow diagnostic device operates on a series of capillary beds that are arranged to permit capillary flow communication with each other. Material used in the assay developing regions in the lateral flow devices requires certain properties for optimal performance of the assay. These properties include consistent capillary flow, appropriate detector bead mobility, appropriate detector line formation, high protein binding, and durability.

In certain aspects, provided herein are non-woven fiber membranes (e.g., electrospun or electroblown non-woven fiber mat membranes) that are suitable for use in lateral flow diagnostic devices. In certain embodiments the non-woven fiber membranes provided herein exhibit properties desirable for use in lateral flow diagnostic devices (e.g., consistent capillary flow, appropriate detector bead mobility, appropriate detector line formation, high protein binding, and high durability). In certain embodiments, provided herein are lateral flow diagnostic devices comprising the non-woven fiber membranes provided herein and methods of using such devices. In certain embodiments, provided herein are methods of making such non-woven fiber membranes using needle-electrospinning, needleless electrospinning or electroblowing.

In certain embodiments, the larger diameter electrospun or electroblown fibers disclosed herein produce fiber mats that possess and provide unique properties such as high bulk porosity, large pore size ratings with narrow distributions, high surface area, and high and tunable protein binding. In certain embodiments, the electrospun or electroblown fiber mats disclosed herein have the potential to provide greater lateral flow assay sensitivity and can enable future applications that leverage these aforementioned properties. Also, in some embodiments, the electrospun or electroblown fiber mats are flexible and non-brittle allowing them to be rolled or folded as compared to existing air cast nitrocellulose membranes, which can open the door to non-flat applications.

Definitions

For convenience, certain terms employed in the specification, examples, and appended claims are collected here.

As used herein, the singular forms "a," "an" and "the" are intended to include the plural forms as well, unless the context clearly indicates otherwise.

The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. "About" can mean a range of up to 0-20%, 0 to 10%, 0 to 5%, or up to 1% of a given value. Where the terms "about" or "approximately" are used in the context of compositions containing amounts of ingredients or conditions such as temperature or viscosity, these values include the stated value with a variation of 0-10% around the value (X±10%).

The terms "including," "includes," "having," "has," "with," or variants thereof are inclusive in a manner similar to the term "comprising." The phrases "consisting essentially of" or "consists essentially of" encompass embodiments containing the specified materials or steps and those including materials and steps that do not materially affect the basic and novel characteristic(s) of the embodiments.

Ranges are stated in shorthand to avoid having to set out at length and describe each and every value within the range. Therefore, when ranges are stated for a value, any appropriate value within the range can be selected, and these values include the upper value and the lower value of the range. For example, a range of 0.11.0 represents the terminal values of 0.1 and 1,0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc.

"Nitrocellulose," which is also known as cellulose nitrate, is a polymer formed by nitrating cellulose with a nitrating agent, for example, nitric acid.

As used herein, an "air-cast membrane" is a porous structure formed from polymers dissolved in a solvent through a process of controlled evaporation of the solvent.

As used herein, the phrase "capillary flow porometry" is used interchangeably with the term "porometry" and is a characterization technique based on the displacement of a wetting liquid from the sample pores by applying a gas at increasing pressure.

As used herein the term "mean flow pore size" or "MFP" refers to a pore diameter calculated as the half way point from the flow pressure curve where the wet curve meets the half dry curve in capillary flow porometry. MFP corresponds to the pore size where 50% of the gas flow passes the wet membrane.

As used herein, a "maximum flow pore size" is the first bubble point measured and calculated in pore size where the first flow is detected through a wet membrane in capillary flow porometry.

As used herein, the term "capillary flow time" or "CFT" refers to time taken for a uniform liquid front to travel across 4 cm of a 1×4 cm strip. To measure CFT, a test strip of 1×4 cm is set into a well containing 150 μL of water and the time taken for a uniform liquid front to travel across the full 4 cm length is measured as CFT.

The "detector bead mobility test" examines the ability of a membrane to allow beads of a specific size to freely pass through the pore structure of the membrane without any separation between the liquid flow front and the bead front. Typically, colored beads are used in this test to facilitate visualization of the bead front. A membrane passes the detector bead mobility test only if there is no visible separation of a clear liquid flow front and colored front line of detector beads. Typically, detector bead mobility test is performed on a 1×4 cm test membrane dipped into 25 μL solution containing latex beads of a particular size, where the solution containing the beads is allowed to flow to the top. The liquid front and the bead front are observed to determine whether the test membrane passed the detector bead mobility test.

The term "porosity" is used herein to express the extent of empty spaces in a material and is a fraction of the volume of empty space over the total volume.

Percentage porosity is calculated based on the following equation:

% Porosity=[1−(basis weight/(mat thickness×polymer density))], where the unit for basis weight is g/m$^2$, the unit for polymer density is g/m$^3$, and the unit for mat thickness is m.

The phrase "assay developing region" corresponds to the region of a device designed to indicate the presence or absence of an analyte. Typically, the assay developing region comprises a test region comprising a binding agent that specifically binds to the analyte or conjugate of the analyte with other ingredients used in the device. An assay developing region may also comprise a control region comprising a binding agent that specifically binds to an ingredient used in the device and which is designed to detect that the assay performed as expected.

As used herein, the term "surfactant" refers to a compound that lower the surface tension (or interfacial tension) between two liquids or between a liquid and a solid. Surfactants may act as detergents, wetting agents, emulsifiers, foaming agents, and dispersants. In some instances, surfactants are organic compounds that are amphiphilic, meaning they contain both hydrophobic groups (their tails) and hydrophilic groups (their heads). Thus, a surfactant can contain both a water-insoluble (or oil-soluble) component and a water-soluble component. Surfactants will diffuse in water and adsorb at interfaces between air and water or at the interface between oil and water, in the case where water is mixed with oil. The water-insoluble hydrophobic group may extend out of the bulk water phase, into the air or into the oil phase, while the water-soluble head group remains in the water phase.

Non-Woven Fiber Membranes

In certain aspects, provided herein are non-woven fiber membranes useful for lateral flow diagnostic devices. In certain embodiments, the non-woven fiber membranes provided herein are generated by an electrospinning process. In some embodiments, the electrospinning process is a needle-less electrospinning process. In some embodiments, the electrospinning process is a needle electrospinning process. In some embodiments, the non-woven fiber mats are produced by an electroblowing process.

In some embodiments, the non-woven fiber membranes, electrospun membranes and/or electroblown membranes described herein are comprised of electrospun or electroblown non-woven nanofibers having an average fiber diameter between 200 nm and 1000 nm. In certain embodiments, the nanofibers have an average fiber diameter of at least 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, or 950 nm. In some embodiments, the nanofibers have an average fiber diameter of no more than 1000 nm, 950 nm, 900 nm, 850 nm, 800 nm, 750 nm, 700 nm, 650 nm, 600 nm, 550 nm, 500 nm, 450 nm, 400 nm, 350 nm, 300 nm, or 250 nm. In some embodiments, the average fiber diameter of the nanofibers is at least about 500 nm. In one embodiment, the average fiber diameter of non-woven nanofibers is 200±40 nm, 250±50 nm, 300±60 nm, 350±70 nm, 400±80 nm, 450±90 nm, 500±100 nm, 550±110 nm, 600±120 nm, 650±130 nm, 700±140 nm, 750±150 nm, 800±160 nm, 850±170 nm, 900±180 nm, 950±190 nm, or 1000±200 nm. In certain embodiments, the fiber membranes provided herein comprise of non-woven nanofibers, wherein at least 80%, 85%, 90%, 95%, or 99% of the nanofibers have a fiber diameter of 200±40 nm, 250±50 nm, 300±60 nm, 350±70 nm, 400±80 nm, 450±90 nm, 500±100 nm, 550±110 nm, 600±120 nm, 650±130 nm, 700±140 nm, 750±150 nm, 800±160 nm, 850±170 nm, 900±180 nm, 950±190 nm, or 1000±200 nm. In certain embodiments, the fiber membranes provided herein comprise of non-woven nanofibers, wherein at least 80%, 85%, 90%, 95%, or 99% of the nanofibers have a fiber diameter of about: 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, or 1000 nm.

In some embodiments, the non-woven fiber membranes provided herein have a MFP of at least about 1 micron. In some embodiments, the non-woven fiber membranes provided herein have a MFP of at least about 2 microns. In certain embodiments, the non-woven fiber membranes provided herein have a MFP of at least about: 1.0 micron, 1.2 microns, 1.3 microns, 1.4 microns, 1.5 microns, 1.6 microns, 1.7 microns, 1.8 microns, 1.9 microns, 2.0 microns, 2.1 microns, 2.2 microns, 2.3 microns, 2.4 microns, 2.5 microns, 2.6 microns, 2.7 microns, 2.8 microns, 2.9 microns, 3.0 microns, 3.5 microns, or 4.0 microns. In some embodiments, the MPF of the non-woven fiber membrane is 1 to 4 microns, 1.5 to 4 microns, 2 to 4 microns, 1 to 3.5 microns, 1.5 to 3.5 microns, 2 to 3.5 microns or 2.5 to 3.5 microns. In specific embodiments, the non-woven fiber membranes provided herein have a pore size distribution as shown in FIG. 38.2.

In some embodiments, the non-woven fiber membranes provided herein have a porosity of at least about 70%. In some embodiments the non-woven fiber membrane has a porosity of at least 71%, 72%, 73%, 74%, 75%, 76%, 77%, 78%, 79%, 80%, 81%, 82%, 83%, 84%, 85%, 86%, 87%, 88%, 89%, or 90%. In some embodiments the non-woven fiber membrane has a porosity of 70% to 95%, 70% to 90%, 75% to 90% or 80% to 90%.

In a particular aspect, the non-woven fiber membranes provided herein are comprised of nanofibers that are electrospun, for example, using needle electrospinning or needle-less electrospinning. In some embodiments, the non-woven fiber membranes provided herein are comprised of nanofibers that are electrospun using needle-less electrospinning.

In some embodiments, the non-woven fiber membranes provided herein are comprised of nanofibers made from a polymer or a blend of polymers that is suitable for being electrospun or electroblown into nanofibers. Non-limiting examples of polymers or blends of polymers that can be electrospun or electroblown into nanofibers include: nylon, such as nylon-46, nylon-66, polyurethane (PU), polybenzimidazole, polycarbonate, polyacrylonitrile, polyvinyl alcohol, polylactic acid (PLA), polyethylene-co-vinyl acetate (PEVA), PEVA/PLA, PMMA, PMMA/tetrahydroperfluorooctylacrylate (TAN), polyethylene oxide (PEO), collagen-PEO, polystyrene (PS), polyaniline (PANI)/PEO, PANI/PS, polyvinylcarbazole, PET, polyacrylic acid-polypyrene methanol (PAA-PM), polyamide (PA), silk/PEO, polyvinylphenol (PVP), polyvinylchloride (PVC), cellulose acetate (CA), PAA-PM/PU, polyvinyl alcohol (PVA)/silica, polyacrylamide (PAAm), poly(lactic-co-glycolic acid) (PLGA), polycarprolactone (PCL), poly(2-hydroxyethyl methacrylate) (HEMA), PVDF, PVDF/PMMA, polyether imide (PEI), polyethylene glycol (PEG), poy(ferrocenyldimethylsilane) (PFDMS), Nylon6/montmorillonite (Mt), poly(ethylene-co-vinyl alcohol), polyacrylnitrile (PAN)/TiO$_2$, polycaprolactone (PCL)/metal, polyvinyl porrolidone, polymetha-phenylene isophthalamide, polyethylene (PE), polypropylene (PP), nylon-12, PET, polyethylene naphthalate (PEN), polyether sulfone (PES), polyvinyl butyral (PVB), PET/PEN, or a blend of one or more of these polymers.

Examples of electrospinning certain polymers into nanofibers are provided in the Huang et al. reference (Huang et al., *Composites Science and Technology*, 63 (2003) 2223-2253), which is herein incorporated by reference in its entirety, particularly, Table 1. In certain embodiments, the non-woven fiber membranes provided herein comprise nanofibers composed of a polymer selected from PMMA, PVDF, or a blend of PMMA and PVDF. In some embodiments, the nanofibers are composed of a blend of PMMA and PVDF. In some embodiments, the blend of PVDF has a weight ratio of PMMA to PVDF of from 1:99 and 99:1. In some embodiments, the weight ratio of PMMA to PVDF is about 10:90, 15:85, 20:80, 25:75, 30:70, 35:65, 40:60, 45:55, 50:50, 55:45, 60:40, 65:35, 70:30, 75:25, 80:20, 85:15, or 90:10. In preferred embodiments, the blend of PMMA and PVDF have the weight ratio of PMMA to PVDF from 60:40 to 70:30. In some embodiments, the weight ratio of PMMA to PVDF is about 60:40, 61:39, 62:38, 63:37, 64:36, 65:35, 66:34, 67:33, 68:32, 69:31, or 70:30.

In certain embodiments, the non-woven fiber membranes provided herein have a thickness of from 25 microns to 250 microns, 50 to 225 microns, 75 to 200 microns, 100 microns to 175 microns, or 125 to 150 microns. In some embodiments, the non-woven fiber membranes have a thickness of about 25 microns, 30 microns, 35 microns, 40 microns, 45 microns, 50 microns, 55 microns, 60 microns, 65 microns, 70 microns, 75 microns, 80 microns, 85 microns, 90 microns, 95 microns, 100 microns, 105 microns, 110 microns, 115 microns, 120 microns, 125 microns, 130 microns, 135 microns, 140 microns, 145 microns, 150 microns, 155 microns, 160 microns, 165 microns, 170 microns, 175 microns, 180 microns, 185 microns, 190 microns, 195 microns, or 200 microns In certain embodiments, the non-woven fiber membranes provided herein have a CFT of from: 75 to 300 seconds, 100 to 275 seconds, 125 to 250 seconds, 150 to 225 seconds, or 175 to 200 seconds.

In some embodiments, the non-woven fiber membranes provided herein pass the detector bead mobility test for beads having a size between: 40 to 600 nm, 60 to 580 nm, 80 to 560 nm, 100 to 540 nm, 120 to 520 nm, 140 to 500 nm, 160 to 480 nm, 180 to 460 nm, 200 to 440 nm, 240 to 420 nm, 260 to 400 nm, 280 to 380 nm, 300 to 360 nm, 320 to 340 nm, or about 400 nm.

In even further embodiments, the non-woven fiber membranes provided herein having a thickness of about 40 to 60 microns have a protein binding capacity of at least about: 70 to 120 $mg/cm^2$, 80 to 110 $mg/cm^2$, or 90 to 100 $mg/cm^2$.

In some embodiments, non-woven fiber membranes provided herein provide desirable characteristics, for example, CFTs of 75 to 300 seconds with less deviation, suitable detector bead mobility, suitable protein striping quality, higher and tunable protein binding, higher porosity, higher surface area, similar area ratios, less background autofluorescence, and potential for lower analyte detection limits and potentially more accurate assay quantification. Other beneficial improvements provided by the electrospun or electroblown fiber membranes provided herein include stable synthetic polymers that give better reproducibility in manufacturing, better consistency in the end user applications, longer shelf-life, non-hazardous materials (especially, compared to nitrocellulose), and lower capital investment in manufacturing equipment with smaller square foot requirements than air-casting equipment.

Lateral Flow Diagnostic Devices

In certain aspects, provided herein are devices comprising a non-woven fiber membrane provided herein. In some embodiments, such devices are designed for detecting an analyte in a sample. In some embodiments, the device comprises an assay developing region comprising the non-woven fiber membranes described herein.

Figure 1:
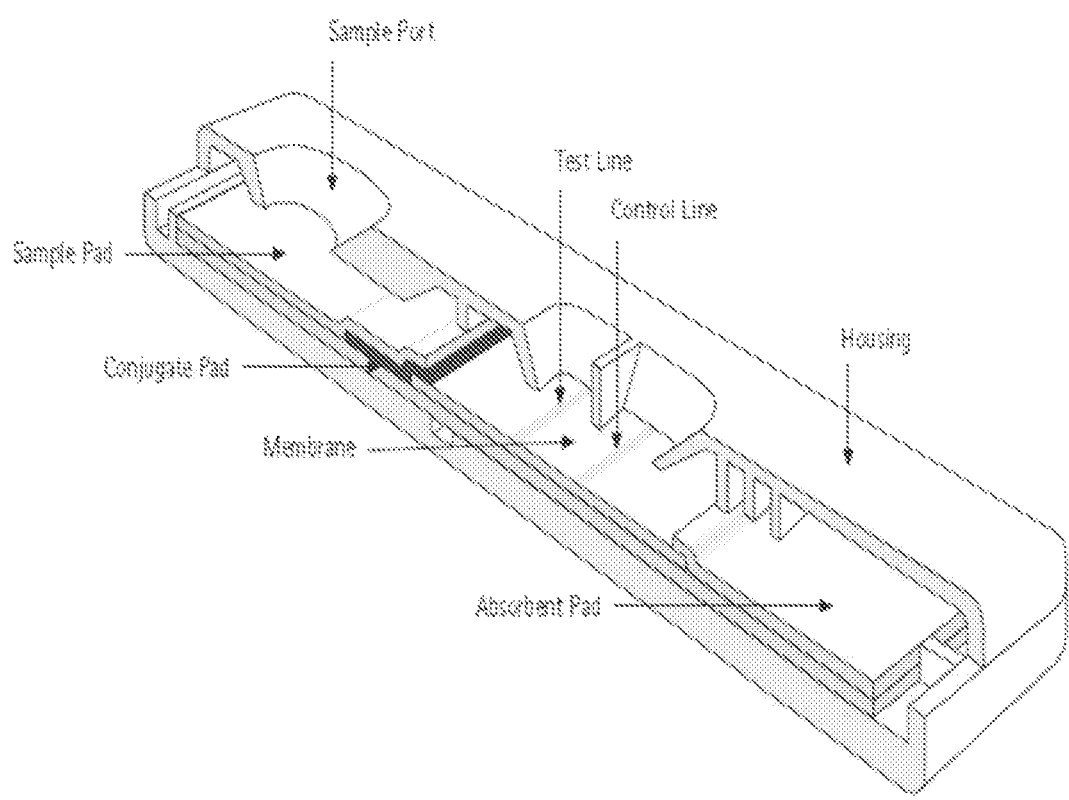
FIG. 1 shows a cross-section of an exemplary lateral flow diagnostic device. In certain embodiments provided herein, the membrane in the developing region of the assay will be an electrospun non-woven fiber mat membrane as disclosed herein.
Figure 2:
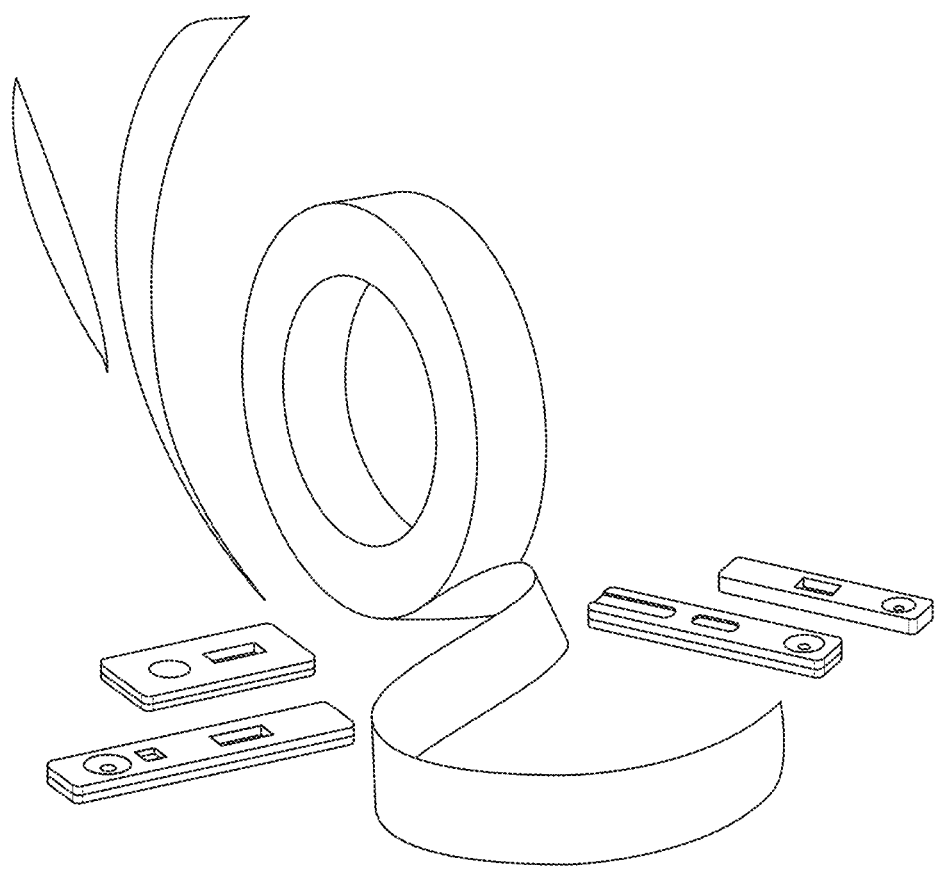
FIG. 2 shows an example of a prior art Hi-Flow™ Plus nitrocellulose membrane on polyethylene terephthalate (PET) backing produced by air-casting.

In certain embodiments, the devices are lateral flow diagnostic devices. A schematic depiction of an exemplary lateral flow diagnostic device is provided in FIG. 1. Certain description of the lateral flow diagnostic devices is provided, for example, in Lateral Flow Immunoassay (2009), Editors: Raphael Wong and Harley Tse (Editor), Humana Press, which is herein incorporated by reference in its entirety.

Additional description of lateral flow diagnostic devices is provided in the Sajid et al. reference, (*J Saudi Chem. Soc.*, (2015); (19) 6: 689-705), which is herein incorporated by reference in its entirety, particularly, Table 2.

In certain embodiments, the lateral flow diagnostic devices provided herein comprise: a sample port designed to receive samples, a conjugate pad, an assay developing region, and an absorbent pad. The conjugate pad, the assay developing region, and the absorbent pad are connected to permit capillary flow communication with each other. In the lateral flow diagnostic devices described herein, the assay developing regions are made from the non-woven fiber membranes described herein.

In typical lateral flow diagnostic devices, a sample pad holds an excess of sample fluid. Once the sample pad is soaked in a sample fluid, the fluid migrates to the conjugate pad, which contains a conjugate of particles and a first binding agent that specifically binds to the analyte. The conjugate pad can contain a dried form of buffer/salt/sugar matrix that provides appropriate conditions for the binding between the analyte and the first binding agent that is immobilized onto the particles. The sample fluid dissolves the buffer/salt/sugar matrix as well as the particles. In a combined transport action, the sample and conjugate mixture flows through the porous structure. During this transport, the analyte binds to the first binding agent conjugated to the particles while migrating further through the assay developing region. The assay developing region has a test region and optionally, a control region, where additional molecules have been immobilized. By the time the sample-conjugate mixture reaches the control and the test regions, the analyte has been bound to the particle and the molecules in the test and the control regions bind the complex of particles-first binding agent-analyte or the particles-first binding agent. As more and more fluid has passed the control and test regions, particles accumulate and the regions change color. After passing these reaction zones, the sample fluid enters the final porous material, the absorbent pad, which acts as a waste container.

In certain lateral flow diagnostic devices described herein, the conjugate pads comprise particles conjugated to a first analyte binding agent that specifically binds to the analyte. The particles conjugated to the first analyte binding agent can be colored particles or chromogenic particles. Non-limiting examples of colored or chromogenic particles include gold particles or latex beads. The particles conjugated to the first analyte binding agent can also be magnetic particles and aggregates, fluorescent materials, or luminescent materials. The particles conjugated to the first analyte binding agent can also be colloidal carbon.

In the lateral flow diagnostic devices described herein, the developing regions of the diagnostic devices are made from the non-woven membranes provided herein. In certain devices, the developing regions comprise a test region comprising immobilized to the test region a second analyte binding agent that specifically binds to the analyte. In certain devices, the developing regions can further comprise a control region comprising immobilized to the control region a particle binding agent that binds to the particles.

The lateral flow diagnostic devices described herein can be designed to detect an analyte selected from a metabolite, hormone, therapeutic drug, drug of abuse, peptide, antibody, and antigen. Certain examples of analytes that can be detected using the lateral flow diagnostic devices provided herein are provided in Table 2 of the Sajid et al. reference. Additional examples of analytes that can be detected using the lateral flow diagnostic devices provided herein include luteinizing hormone, human chorionic gonadotrophin, cholesterol, or glucose.

In some embodiments, provided herein are methods of using the lateral flow diagnostic devices described herein to detect an analyte in a sample. The analyte can be a biological analyte and the sample can be a biological sample, for example, a body fluid or tissue extract.

Non-limiting examples of biological analytes include a metabolite, hormone, therapeutic drug, drug of abuse, peptide, antibody, antigen; and the biological sample is a body fluid. The analytes described in Table 2 of the Sajid et al. reference can be detected in the methods provided herein. Additional examples of analytes that can be detected in the methods provided herein include luteinizing hormone, human chorionic gonadotrophin, cholesterol, or glucose. Even further examples of analytes that can be detected according to the methods provided herein are known or readily apparent to a person of ordinary skill in the art and such embodiments are within the purview of the methods and devices provided herein.

In certain embodiments, the methods provided herein are carried out on a body fluid selected from amniotic fluid, aqueous humor, vitreous humor, bile, blood, cerebrospinal fluid, chyle, endolymph, perilymph, female ejaculate, lymph, mucus (including nasal drainage and phlegm), pericardial fluid, peritoneal fluid, pleural fluid, pus, rheum, saliva, sputum, synovial fluid, vaginal secretion, semen, blood, serum, or plasma.

In other embodiments, the methods provided herein are carried out on an organ or tissue extract. Non-limiting examples of the organ or tissue which can be used to produce an extract include placenta, brain, eyes, pineal gland, pituitary gland, thyroid gland, parathyroid glands, thorax, heart, lung, esophagus, thymus gland, pleura, adrenal glands, appendix, gall bladder, urinary bladder, large intestine, small intestine, kidneys, liver, pancreas, spleen, stoma, ovaries, uterus, testis, skin, blood or buffy coat sample of blood. Additional examples of organs and tissues from any biological source are well known to a person of ordinary skill in the art and such embodiments are within the purview of the methods provided herein.

In certain embodiments, the larger diameter electrospun fibers disclosed herein produce fiber mats that possess and provide unique properties such as high bulk porosity, large pore size ratings with narrow distributions, high surface area, and high and tunable protein binding. In certain embodiments, the electrospun fiber mats disclosed herein have the potential to provide greater lateral flow assay sensitivity and can enable future applications that leverage these aforementioned properties. Also, in some embodiments, the electrospun fiber mats are flexible and non-brittle allowing them to be rolled or folded as compared to existing air cast nitrocellulose membranes, which can open the door to non-flat applications.

Methods of Making Non-Woven Fiber Mats

In certain aspects, provided herein are methods of producing the non-woven fiber membranes described herein. Particularly, the methods comprise electrospinning (e.g., needle-less electrospinning or needle electrospinning) or electroblowing a polymer preparation onto a non-porous film or porous substrate potentially followed by transfer to a film substrate using any method of adhesion to produce the non-woven fiber membranes provided herein.

Electrospinning is process of producing nanofibers from a mixture of polymers, for example, polymer solution or polymer melt. The process involves applying an electric potential to such a polymer solution or polymer melt. Certain details of the electrospinning process for making an electrospun nanofiber mat or membrane, including suitable apparatuses for performing the electrostatic spinning process, are described in International Patent Application Publications WO2005/024101, WO2006/131081, and WO2008/106903, each of which is incorporated herein by reference in its entirety.

During electrospinning process, fibers are ejected or spun from a spinning electrode by applying a high voltage to the electrodes and a polymer solution where fibers are charged or spun toward a collecting electrode and collected as a highly porous non-woven mat on a substrate between the electrodes.

Figure 4:
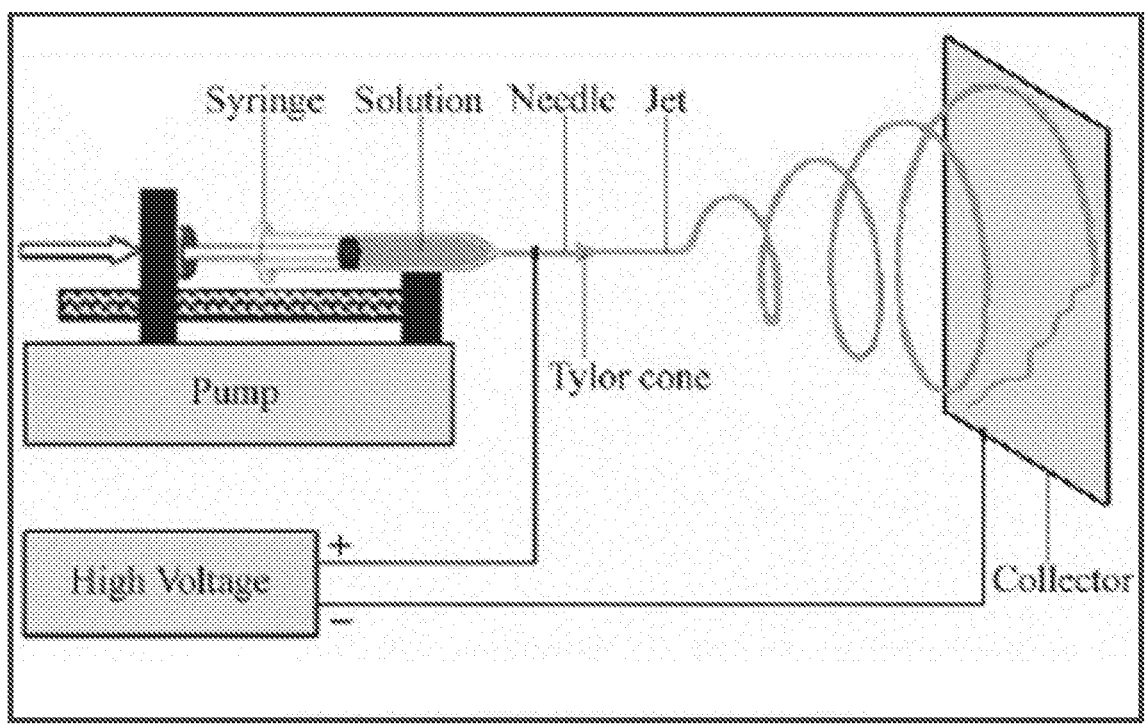
FIG. 4 shows a schematic of an exemplary needle electrospinning process. The spinning electrode is a metal syringe that also dispenses the polymer solution via a syringe pump.

Two methods to electrospinning are needle and needle-less electrospinning. Needle electrospinning (FIG. 4) is typically set up where the spinning electrode is a metal syringe, which also dispenses the polymer solution via a syringe pump. Needle electrospinning set-ups are typically performed in custom lab scale or smaller commercially produced machines.

Needle-less electrospinning provides greater productivity of fiber mass/time and the ability to operate on a wider area and on moving basis to collect continuous roll stock of non-woven fiber mat membranes. Examples of commercial needle-less electrospinning equipment include ELMARCO, s.r.o. (Liberec, Czech Republic). ELMARCO electrospinning machines function with two types of dispensing of the polymer solution onto the spinning electrode.

Figure 5:
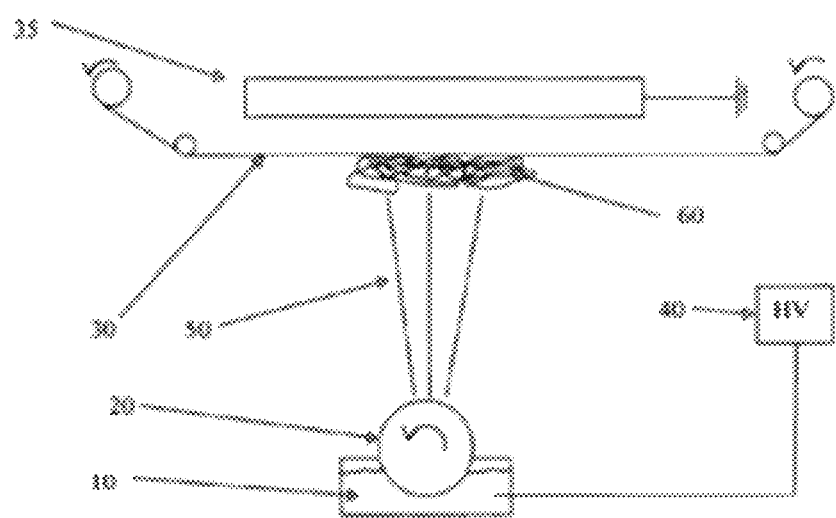
FIG. 5 shows a schematic representation of an exemplary needleless electrospinning process, depicting a rotating wire electrode, where 10 is polymer bath, 20 is rotating spinning electrode, 30 is collection substrate, 35 is collecting electrode, 40 is voltage source, and 50 and 60 are fibers.

In some electrospinning methods, in the rotating wire electrode machines the polymer solution is coated on the rotating spinning electrode in a coating bath (FIG. 5). ELMARCO models NSLAB200A and NS3A1000U (listed in Table 1) feature this technology with maximum voltage of 82 kV and widths of 20 and 100 cm. Certain other embodiments involve fixed unwinding wire electrode(s) for spinning, where the polymer solution is capillary dispensed via a moving head. These machines have max voltage of 100 kV and widths of 50 and 160 cm. This technology is available in models NS1WS500U and NS8S1600U (also listed in Table 1).

TABLE 1

Specifications of the ELMARCO s.r.o. (Liberec, Czech Republic) needle-less electrospinning machines.

| | Rotating wire electrode | Fixed wire electrode |
|---|---|---|
| Manufacturer | ELMARCO | ELMARCO |
| System | NSLAB200S/NS3A1000U | NS1WS500U/NS8S1600U |
| Continuous | Yes | Yes |
| Solution application | Open pan dip coating | Capillary coating |
| Width (cm) | 20/100 | 50/160 |
| Max Voltage (kV) | 82 | 100 |

In some embodiments, the nanofiber compositions are made from a single nanofiber, wherein the single nanofiber is made by a single pass of a moving collection apparatus positioned between the spinning and the collector electrodes. A fibrous web of nanofibers can be formed by one or more spinning electrodes running simultaneously above/below the same moving collection apparatus.

In some embodiments, the non-woven fiber membranes provided herein are generated through an electroblowing process. An exemplary electroblowing process is provided in US. Pat. Pub. No. 2007/0075015, which is hereby incorporated by reference. For example, in some embodiments the fiber mat can be generated through the use of a fine fiber spinning apparatus comprising a spinning beam comprising at least one spinning beam comprising a spinning nozzle, a blowing gas injection nozzle and a collector, the spinning beam and the collector having high-voltage electrostatic weld maintained therebetween. A polymer solution comprising a polymer and a solvent is supplied to the spinning nozzle a polymer, which compressively discharges the polymer solution from the spinning nozzle while blowing the solution with a blowing gas discharged from the gas injection nozzle to form a fibrous web of fibers, and collecting the fibrous web on a moving collection apparatus in a single pass beneath a single spinning beam. In some embodiments, thermal calendaring can be used to reduce the thickness and increase the density and solidity of the resulting medium, and reduce the size of the pores.

The electrospun or electroblown fiber mat membranes provided herein have a different 3-dimensional morphology compared to air-cast membranes, where the porosity results from the non-woven overlapping of polymer fibers with sub-micron to micron sized average fiber diameters that proportionally produce the pore size diameter ratings.

The electrospun or electroblown non-woven fiber mat membranes provided herein provide specific advantages. For example, in certain embodiments, needle-less electrospinning can be scaled-up to continuous roll manufacturing to produce electrospun non-woven fiber mat membranes on non-porous substrates that can be used in lateral flow diagnostics devices. The non-woven fiber mat membranes provided herein can be effectively electrospun or electroblown onto non-porous film or porous substrates with productivity, uniformity, and adhesion on moving substrates.

The polymer solutions, for example, polymer types, grades, mix ratios, mass percentages, solvents, and viscosities, disclosed herein as well as the electrospinning conditions, for example, machine type, film substrate specifications, voltages, dew points, and line speeds, can be used to make continuous roll stock of electrospun non-woven fiber mat membranes on non-porous films. Specific blends of different polymers, for example, percentage solids, ratios, solvents, viscosities, and different grades of polymers can be used to produce required fiber diameters to produce non-woven fiber mat membranes having desirable properties, for example, MFP, porosity, and thickness, for use in lateral flow diagnostic devices.

Figure 6:
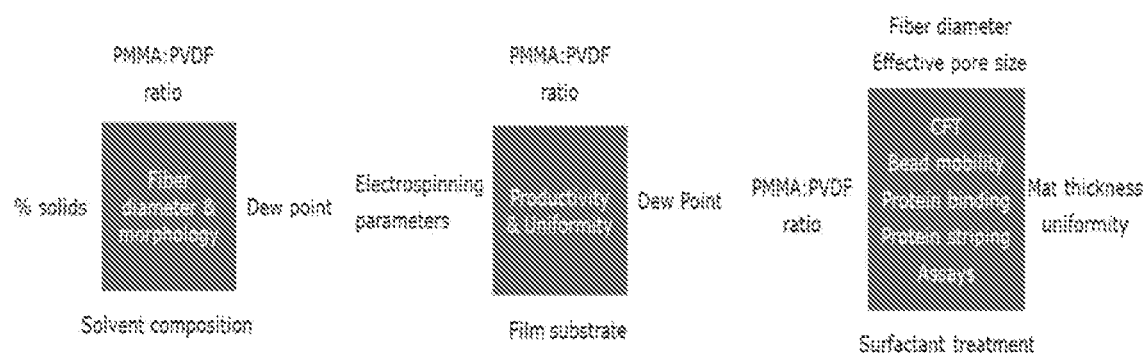
FIG. 6 shows that electrospun fiber diameter and morphology are predominantly controlled by PMMA:PVDF ratio, % solids, solvent, and dew point. The electrospun non-woven fiber mat productivity and uniformity are controlled by four parameters, namely, PMMA:PVDF ratio, electrospinning parameters, dew point, and film substrate. Properties that affect performance of membranes in the lateral flow diagnostic devices, such as CFT, detector bead mobility, protein binding, protein striping, and functional assay performance, are fiber diameter/effective pore size, PMMA:PVDF ratio, surfactant treatment, mat thickness, and uniformity.

The process of producing fibers via electrospinning also has several parameters that control fiber diameters and mat properties. In addition to electrospinning technology, other parameters can be controlled to provide fibers and mats with desirable properties. FIG. 6 indicates that four parameters (PMMA:PVDF ratio, % solids, dew point, and solvent composition) control fiber diameter and morphology. Also, four parameters (PMMA:PVDF ratio, electrospinning parameters, dew point, and film substrate) contribute to non-woven fiber mat productivity and uniformity. Additionally, four parameters (fiber diameter/effective pore size, PMMA:PVDF ratio, surfactant treatment, and mat thickness and uniformity) contribute to the properties relevant for use in lateral flow diagnostic assay applications, namely, CFT, detector bead mobility, protein binding, protein striping, and functional assay performance. The electrospinning parameters that can be controlled during electrospinning nanofibers include voltage, air flow, electrode distance, substrate line speed, carriage speed, dispensing orifice, and spinning electrode wire speed.

The polymer preparations that can be electrospun or electroblown for producing the non-woven fiber mat membranes provided herein include a polymer melt or a polymer solution. The polymer melt or the polymer solution can comprise one or more polymers. For example, the polymer preparation can comprise one or more polymers selected from: nylon, such as nylon-46, nylon-66, polyurethane (PU), polybenzimidazole, polycarbonate, polyacrylonitrile, polyvinyl alcohol, polylactic acid (PLA), polyethylene-co-vinyl acetate (PEVA), PEVA/PLA, PMMA, PMMA/tetrahydroperfluorooctylacrylate (TAN), polyethylene oxide (PEO), collagen-PEO, polystyrene (PS), polyaniline (PANI)/PEO, PANI/PS, polyvinylcarbazole, PET, polyacrylic acid-polypyrene methanol (PAA-PM), polyamide (PA), silk/PEO, polyvinylphenol (PVP), polyvinylchloride (PVC), cellulose acetate (CA), PAA-PM/PU, polyvinyl alcohol (PVA)/silica, polyacrylamide (PAAm), poly(lactic-co-glycolic acid) (PLGA), polycarprolactone (PCL), poly(2-hydroxyethyl methacrylate) (HEMA), PVDF, PVDF/PMMA, polyether imide (PEI), polyethylene glycol (PEG), poy(ferrocenyldimethylsilane) (PFDMS), Nylon6/montmorillonite (Mt), poly(ethylene-co-vinyl alcohol), polyacrylnitrile (PAN)/$TiO_2$, polycaprolactone (PCL)/metal, polyvinyl porrolidone, polymetha-phenylene isophthalamide, polyethylene (PE), polypropylene (PP), nylon-12, PET, polyethylene naphthalate (PEN), polyether sulfone (PES), polyvinyl butyral (PVB), or PET/PEN.

In preferred embodiments, the polymer preparations used in the methods of producing the non-woven fiber mat membranes provided herein comprise PMMA, PVDF, or a blend of PMMA and PVDF. In some embodiments, the blend of PVDF has a weight ratio of PMMA to PVDF of from 1:99 and 99:1. In some embodiments, the weight ratio of PMMA to PVDF is about 10:90, 15:85, 20:80, 25:75, 30:70, 35:65, 40:60, 45:55, 50:50, 55:45, 60:40, 65:35, 70:30, 75:25, 80:20, 85:15, or 90:10. In preferred embodiments, the blend of PMMA and PVDF have the weight ratio of PMMA to PVDF from 60:40 to 70:30. In some embodiments, the weight ratio of PPMA to PVDF is about 60:40, 61:39, 62:38, 63:37, 64:36, 65:35, 66:34, 67:33, 68:32, 69:31, or 70:30.

The polymer preparations comprising PMMA and/or PVDF can be a solution of PVDF and/or PMMA in a solvent selected from DMAC, DMF, or a mixture thereof. In certain embodiments, DMAC, DMF, or a mixture of DMAC and DMF can further comprise acetone.

The polymer preparations comprising PMMA and/or PVDF can contain about 5% to 20% by weight of PMMA, PVDF, or a blend thereof. In certain embodiments, the polymer preparations comprising PVDF and/or PMMA contain about 15%, 16%, 17%, 18%, 19%, or 20% by weight of PMMA, PVDF, or a blend thereof. In further embodiments, the polymer preparations comprising PVDF and PMMA contain about 15%, 16%, 17%, 18%, 19%, or 20% by weight of a blend of PMMA and PVDF, wherein the blend of PMMA and PVDF can have the weight ratio between PMMA to PVDF of 60:40, 65:35, 70:30, 75:25, or 80:20, and wherein the solvent comprises DMAC and/or DMF and optionally, further comprises acetone.

In specific embodiments, the viscosity of the solution of PMMA and/or PVDF in the solvent of DMAC and/or DMF and/or acetone is between: 200 centipoise (cP) to 5000 cP, 300 cP to 2000 cP, 400 cP to 1000 cP, 500 cP to 900 cP, 600 cP to 800 cP, or 700 cP to 800 cP.

In one aspect of the methods provided herein, the non-porous film substrate on which the polymer is electrospun is insoluble in the electrospinning solvent and has minimal or no electrical charge. These properties of the non-porous films allow safe moving web operation and enable well packed and uniform fiber mats. Films that do not have electrical charge allow for moving web collection and can be run at higher voltages.

According to certain embodiments, non-porous film substrates are preferred because such substrates provide a smooth non-woven fiber mat surface and are electrically uncharged in high voltage electric fields. Also, films with low electrical resistance, crystallinity, dielectric strength, and non-polar chemistry are preferred in embodiments where the substrate moves during fiber collection. Non-limiting examples of the non-porous polymer films suitable for use in the methods provided herein comprise polyethylene with carbon, polyimide with carbon, low-density polyethylene (LDPE) with an anti-static additive, polypropylene with anti-static additive, acrylonitrile butadiene styrene with anti-static additive, nylon, static dissipative high molecular weight polyethylene (UHMWPE), polypropylene spun-bound with antistatic treatment, LDPE, polycarbonate, UHMWPE, polyvinyl chloride, PET, PMMA, PVDF, and PMMA/PVDF. For use as non-porous film substrates, the polymer composites with anti-static or static dissipative additives or conductive carbon are preferred because these substrates electrically charged less during electrospinning and led to better fiber mat quality (for example, productivity and uniformity) than the films that electrically charged, such as PET, PVC, PC, PMMA, and PVDF.

In certain embodiments, the nanofibers are electrospun at a voltage of between: 30 to 120 kV, 40 to 110 kV, 50 to 100 kV, 60 to 90 kV, or 70 to 80 kV.

In some embodiments, the electrode distance is between: 150 to 300 mm, 160 to 290 mm, 170 to 280 mm, 180 to 270 mm, 190 to 260 mm, 200 to 250 mm, 210 to 240 mm, or 220 to 230 mm.

In further embodiments, the dispensing orifice is between 0.4 to 0.8 mm, 0.45 to 0.75 mm, 0.5 to 0.6 mm, 0.55 to 0.65 mm, or 0.6 mm.

In certain embodiments, the carriage speed is between 50 to 150 mm/sec, 60 to 140 mm/sec, 70 to 130 mm/sec, 80 to 120 mm/sec, 90 to 110 mm/sec, or 100 mm/sec.

In specific embodiments, the wire speed is between 1 to 5 mm/sec, 2 to 4 mm/sec, or 3 mm/sec.

The speed of air-in the electrospinning chamber can be between 60 $m^3$/hr to 120 $m^3$/hr, 70 $m^3$/hr to 110 $m^3$/hr, 80 $m^3$/hr to 100 $m^3$/hr, or 90 $m^3$/hr; whereas, the speed of air-out of the electrospinning chamber can be between 100 $m^3$/hr to 140 $m^3$/hr, 110 $m^3$/hr to 130 $m^3$/hr, or 120 $m^3$/hr.

The temperature in the spinning chamber can be between 25 to 50° C., 30 to 45° C., 35 to 40° C., or 40 to 45° C.

The relative humidity in the electrospinning chamber can be between: 10 to 35%, 15 to 30%, or 20 to 25%.

In particular embodiments, the dew point in the electrospinning chamber can be between: 2.0° C. to 6.0° C., 2.2° C. to 5.8° C., 2.4° C. to 5.6° C., 2.6° C. to 5.4° C., 2.8° C. to 5.2° C., 3.0° C. to 5.0° C., 3.2° C. to 4.8° C., 3.4° C. to 4.6° C., 3.6° C. to 4.4° C., or 3.8° C. to 4.2° C.

In further embodiments, the line speed is between: 0.5 cm/min to 5.0 cm/min, 1.0 cm/min to 4.5 cm/min, 1.5 cm/min to 4.0 cm/min, 2.0 cm/min to 3.5 cm/min, or 2.5 cm/min to 3.0 cm/min for a one wire machine, and adjusted to scale linearly for more wires.

In certain embodiments provided herein, the methods include a surfactant treatment step (e.g., treatment with one or more surfactants, such as surfactant 1 and surfactant 2). Typically, the surfactants used in the methods provided herein contain a lipophilic nonpolar hydrocarbon group and a polar functional hydrophilic group. In some embodiments, the polar functional group may be a carboxylate, ester, amine, amide, imide, hydroxyl, ether, nitrile, phosphate, sulfate, or sulfonate. The surfactants that are useful in the methods provided herein may be used alone or in combination. Accordingly, any combination of surfactants may include anionic, cationic, nonionic, zwitterionic, amphoteric and ampholytic surfactants. In some embodiments, the surfactants for use in the methods provided herein may be anionic, including, but not limited to, sulfonates such as alkyl sulfonates, alkylbenzene sulfonates, alpha olefin sulfonates, paraffin sulfonates, and alkyl ester sulfonates; sulfates such as alkyl sulfates, alkyl alkoxy sulfates, and alkyl alkoxylated sulfates; phosphates such as monoalkyl phosphates and dialkyl phosphates; phosphonates; carboxylates such as fatty acids, alkyl alkoxy carboxylates, sarcosinates, isethionates, and taurates. Examples of carboxylates are sodium cocoyl isethionate, sodium methyl oleoyl taurate, sodium laureth carboxylate, sodium trideceth carboxylate, sodium lauryl sarcosinate, lauroyl sarcosine, and cocoyl sarcosinate. Specific examples of sulfates include sodium dodecyl sulfate (SDS), sodium lauryl sulfate, sodium laureth sulfate, sodium trideceth sulfate, sodium tridecyl sulfate, sodium cocyl sulfate, and lauric monoglyceride sodium sulfate. Examples of sulfonate surfactants include, but are not limited to, alkyl sulfonates, aryl sulfonates, monoalkyl and dialkyl sulfosuccinates, and monoalkyl and dialkyl sulfosuccinamates. Illustrative examples of alky and aryl sulfonates are sodium tridecyl benzene sulfonate (STBS) and sodium dodecylbenzene sulfonate (SDBS). Illustrative examples of sulfosuccinates include, but are not limited to, dimethicone copolyol sulfosuccinate, diamyl sulfosuccinate, dicapryl sulfosuccinate, dicyclohexyl sulfosuccinate, diheptyl sulfosuccinate, dihexyl sulfosuccinate, diisobutyl sulfosuccinate, dioctyl sulfosuccinate, C12-15 pareth sulfosuccinate, cetearyl sulfosuccinate, cocopolyglucose sulfosuccinate, cocoyl butyl gluceth-10 sulfosuccinate, deceth-5 sulfosuccinate, deceth-6 sulfosuccinate, dihydroxyethyl sulfosuccinylundecylenate, hydrogenated cottonseed glyceride sulfosuccinate, isodecyl sulfosuccinate, isostearyl sulfosuccinate, laneth-5 sulfosuccinate, laureth sulfosuccinate, laureth-12 sulfosuccinate, laureth-6 sulfosuccinate, laureth-9 sulfosuccinate, lauryl sulfosuccinate, nonoxynol-10 sulfosuccinate, oleth-3 sulfosuccinate, oleyl sulfosuccinate, PEG-10 laurylcitrate sulfosuccinate, sitosereth-14 sulfosuccinate, stearyl sulfosuccinate, tallow, tridecyl sulfosuccinate, ditridecyl sulfosuccinate, bisglycol ricinosulfosuccinate, di(1,3-di-methylbutyl)sulfosuccinate, and silicone copolyol sulfosuccinates. The structures of silicone copolyol sulfosuccinates are set forth in U.S. Pat. Nos. 4,717,498; and 4,849,127. Illustrative examples of sulfosuccinamates include, but are not limited to, lauramido-MEA sulfosuccinate, oleamido PEG-2 sulfosuccinate, cocamido MIPA-sulfosuccinate, cocamido PEG-3 sulfosuccinate, isostearamido MEA-sulfosuccinate, isostearamido MIPA-sulfosuccinate, lauramido MEA-sulfosuccinate, lauramido PEG-2 sulfosuccinate, lauramido PEG-5 sulfosuccinate, myristamido MEA-sulfosuccinate, oleamido MEA-sulfosuccinate, oleamido PIPA-sulfosuccinate, oleamido PEG-2 sulfosuccinate, palmitamido PEG-2 sulfosuccinate, palmitoleamido PEG-2 sulfosuccinate, PEG-4 cocamido MIPA-sulfosuccinate, ricinoleamido MEA-sulfosuccinate, stearamido MEA-sulfosuccinate, stearyl sulfosuccinamate, tallamido MEA-sulfosuccinate, tallow sulfosuccinamate, tallowamido MEA-sulfosuccinate, undecylenamido MEA-sulfosuccinate, undecylenamido PEG-2 sulfosuccinate, wheat germamido MEA-sulfosuccinate, and wheat germamido PEG-2 sulfosuccinate. Other suitable surfactants include, Hotapur SAS 30 and Genapol UD-070 produced by Clariant Corporation.

In particular methods provided herein for producing the non-woven fiber mat membranes, the electrospinning of the nanofibers can be performed using needle-electrospinning or needleless electrospinning.

EXEMPLIFICATION

Example 1

Polymer and Solvent Selection and Electrospinning Evaluations

The polymers PMMA and PVDF were used to produce electrospun fiber membranes. PVDF was sourced from Arkema having several grades, melt viscosities or molecular weights as detailed in Table 2. Kynar® Flex 2850 is a PVDF/polyhexafluoropropylene copolymer P(VDF/HPA). PMMA was sourced from ALTUGLAS INTERNATIONAL having several grades, melt viscosities or molecular weights as detailed in Table 3. Solvents DMAC and DMF were used for screening because both are solvents for PMMA and PVDF and have lower vapor pressures that are amenable for use in the ELMARCO rotating wire electrode open pan systems, where rapid solvent evaporation can be problematic. Screening of the PMMA and PVDF grades and solvents was conducted by making 15% w/v solutions in DMF and DMAC and checking solutions for their electrospinning qualities as detailed in Tables 2 and 3. Electrospinning was performed on the ELMARCO NSLAB200A unit from Table 1.

Electrospinning parameters were ΔV of 82 kV, 280 mm electrode distance, 60 Hz electrode rotation, stationary 50 micron Melinex® PET film collecting as substrate, and spinning chamber conditions of 22-25° C. temperature and relative humidity of 10-30%. Table 2 shows that PVDF6 (Kynar® 761) had the highest viscosities in DMAC and DMF and the best fiber quality was produced from DMAC.

TABLE 2

Grades and melt viscosities of PVDF or PVDF/HFP polymers from Arkema. 15% w/v solutions were used to screen viscosities, molecular weights, and electrospinning quality.

| ID # | PVDF or VDF/HFP copolymer, Kynar ® grade (Arkema) | MELT VISCOSITY METHOD (ASTM D3835) 230° C. K POISE @ 100 SEC$^{-1}$ | viscosity (cP) 15% w/v in DMAC | Average fiber diameter (nm), (% w/v) | Fiber quality | viscosity (cP) 15% w/v in DMF | Average fiber diameter (nm), (% w/v) | Fiber quality |
|---|---|---|---|---|---|---|---|---|
| PVDF1 | 705 | 2.0-5.0 | 54 | | Fibers and beads | N.T. | | |
| PVDF2 | 711 | 4.0-8.0 | 120 | 240 ± 55 (25) | Fibers and beads | 53 | | Fibers and beads |
| PVDF3 | 720 | 6.0-12.0 | <15% | | | <15% | | |
| PVDF4 | 752 | 6.0-15.0 | 120 | | Fibers and beads | 100 | | Fibers and beads |
| PVDF5 | Flex 2850 | 23.0-27.0 | 124 | 191 ± 42 (25) | Fibers and beads | 100 | 260 ± 64 (30) | Fibers and beads |
| PVDF6 | 761 | 23.0-29.0 | 630 | 360 ± 120 (15) | Fibers only | 325 | 261 ± 57 (15) | Fibers and beads |

Figure 7:
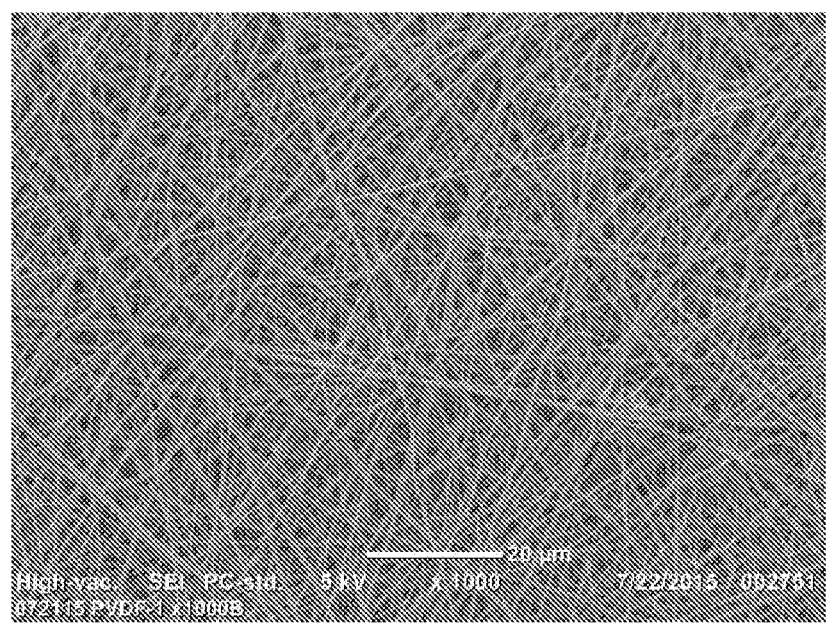
FIG. 7 shows an SEM image of the high fiber quality electrospun from 15% w/v PVDF6 (Kynar® 761) in DMAC (Table 2) yielding an average fiber diameter of 360±120 nm.
Figure 8:
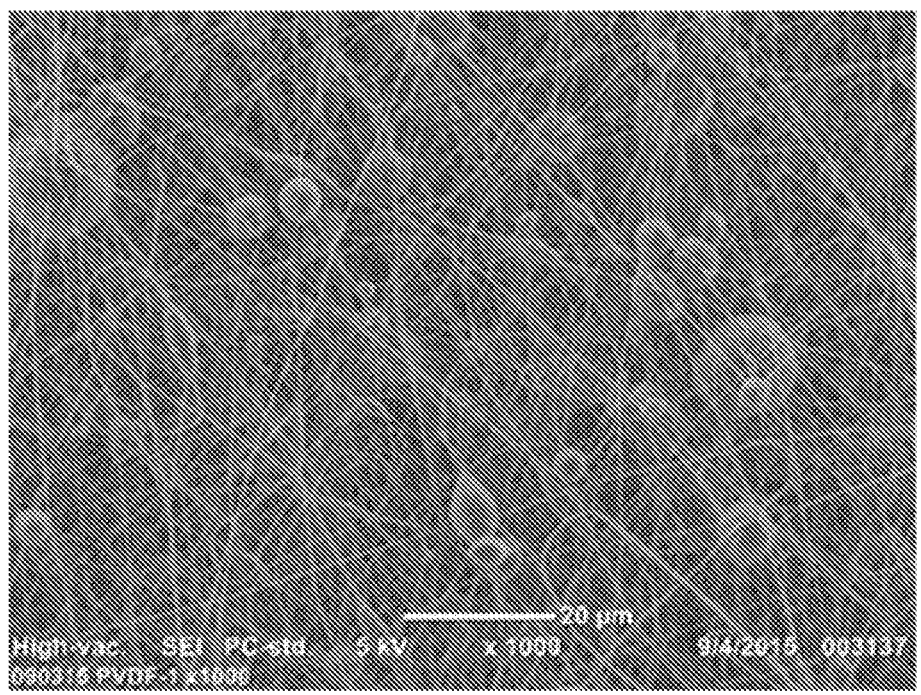
FIG. 8 shows an SEM of the electospun fibers with an average fiber diameter of 240±55 nm and having undesirable beads from a 25% w/v solution of PVDF2 (Kynar® 711) in DMAC.

FIG. 7 shows a sample SEM image of the high fiber quality electrospun from 15% w/v PVDF6 (Kynar® 761) in DMAC (Table 2) yielding an average fiber diameter of 360±120 nm. FIG. 8 shows that a 25% w/v solution of PVDF2 (Kynar® 711) in DMAC (Table 2) produced fibers with an average fiber diameter of 240±55 nm with undesirable beads.

Table 3 shows that 15% w/v PMMA5 (BS572) in DMAC had lower viscosity and better fiber generation than for 15% w/v in DMF. PMMA5 (BS572) produced higher viscosity and average fiber diameters than PVDF6 (Kynar® 761) at 15% w/v in DMAC. BS572 is a pure high molecular weight (HMW) PMMA. Kynar® 761 is a PVDF with a molecular weight of about 450 kilodaltons.

TABLE 3

Grades and viscosities/relative molecular weights of PMMA polymers from ALTUGLAS. 15% w/v solutions were used to screen viscosities, molecular weights, and electrospinning quality.

| ID # | PMMA (ALTUGLAS INTERNATIONAL) | intrinsec viscosity (cm³/g) or Molecular weight | viscosity (cP) 15% w/v in DMAC | Average fiber diameter (nm), (% w/v) | Fiber Quality | viscosity (cP) 15% w/v in DMF | Average fiber diameter (nm), (% w/v) | Fiber quality |
|---|---|---|---|---|---|---|---|---|
| PMMA1 | V920 | Low | 20 | | no/poor fibers | N.T. | | |

TABLE 3-continued

Grades and viscosities/relative molecular weights of PMMA polymers from ALTUGLAS. 15% w/v solutions were used to screen viscosities, molecular weights, and electrospinning quality.

| ID # | PMMA (ALTUGLAS INTERNATIONAL) | intrinsec viscosity (cm³/g) or Molecular weight | viscosity (cP) 15% w/v in DMAC | Average fiber diameter (nm), (% w/v) | Fiber Quality | viscosity (cP) 15% w/v in DMF | Average fiber diameter (nm), (% w/v) | Fiber quality |
|---|---|---|---|---|---|---|---|---|
| PMMA2 | V826 | Medium | 30 | | no/poor fibers | N.T. | | |
| PMMA3 | PRD930 | High | 62 | | no/poor fibers | N.T. | | |
| PMMA4 | PRD521 | Very High | 45 | | no/poor fibers | N.T. | | |
| PMMA5 | BS572 | 170, High | 981 | 2,700 ± 1,300 | good fibers | 3270 | | no/poor fibers |

To produce MFP of more than 2 microns, larger fiber diameters are needed to generate the higher pore size ratings useful in lateral flow diagnostic assays. Because PMMA5 (BS572) electrospun the best quality fibers from DMAC of the grades tested and PVDF6 (Kynar® 761) electrospun the best fiber quality from DMAC, blended ratios of PMMA and PVDF6 (Kynar® 761) as 15% w/v solutions in DMAC were screened for viscosity and electrospun fiber diameter and quality as summarized in Table 4.

TABLE 4

Mixed polymer blend ratios of PMMA grades and PVDF (Kynar ® 761) as 15% w/v solutions in DMAC. Measured solution viscosities and resulting electrospun fiber diameters and quality.

| ID # | PMMA grade | PMMA:PVDF 761 (15% w/v) | viscosity (cP) 15% w/v in DMAC | Average fiber diameter (nm) | Fiber quality |
|---|---|---|---|---|---|
| Mix1 | none | 0:100 | 325 | 166 ± 49 | good fibers |
| Mix2 | BS572 | 20:80 | 560 | 600 ± 290 | good fibers |
| Mix3 | BS572 | 30:70 | 650 | 1,200 ± 320 | good fibers |
| Mix4 | BS572 | 50:50 | 680 | 1,900 ± 930 | good fibers |
| Mix5 | BS572 | 100:0 | 981 | 2,700 ± 1,300 | good fibers |
| Mix6 | PRD930 | 25:75 | 407 | 380 ± 100 | good fibers |
| Mix7 | V920 | 40:60 | 192 | 260 ± 40 | fibers with beads |

Figure 9:
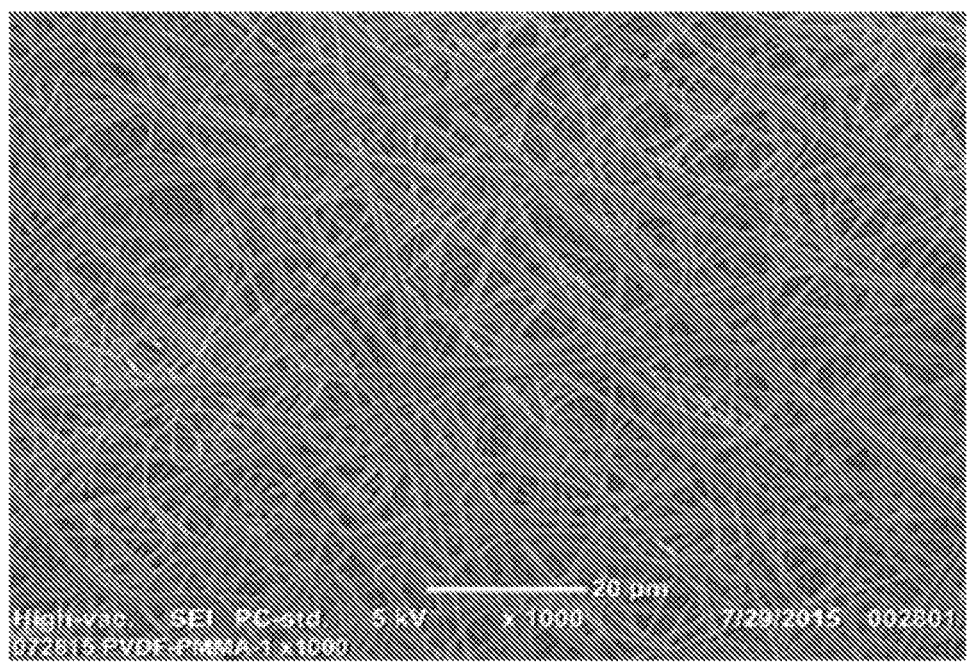
FIG. 9 shows an SEM of the larger diameter fibers (600±290 nm) electrospun from a 15% w/v solution of 20:80 PMMA5 (BS572):PVDF6 (Kynar® 761) in DMAC (Mix2, Table 4).

FIG. 9 shows how a 15% w/v solution of 20:80 PMMA5 (BS572):PVDF6 (Kynar® 761) in DMAC (Mix2, Table 4) produces larger diameter fibers of 600±290 nm. These data demonstrate that the higher viscosity of PMMA (BS572) can be used with varying ratios of PVDF (Kynar® 761) to control the mix viscosity and resulting electrospun fiber diameters. Therefore, blending can be used to produce a range of average fiber diameters that will result in a range of MFP.

Example 2

Advanced Polymer & Solvent Selection

Figure 10:
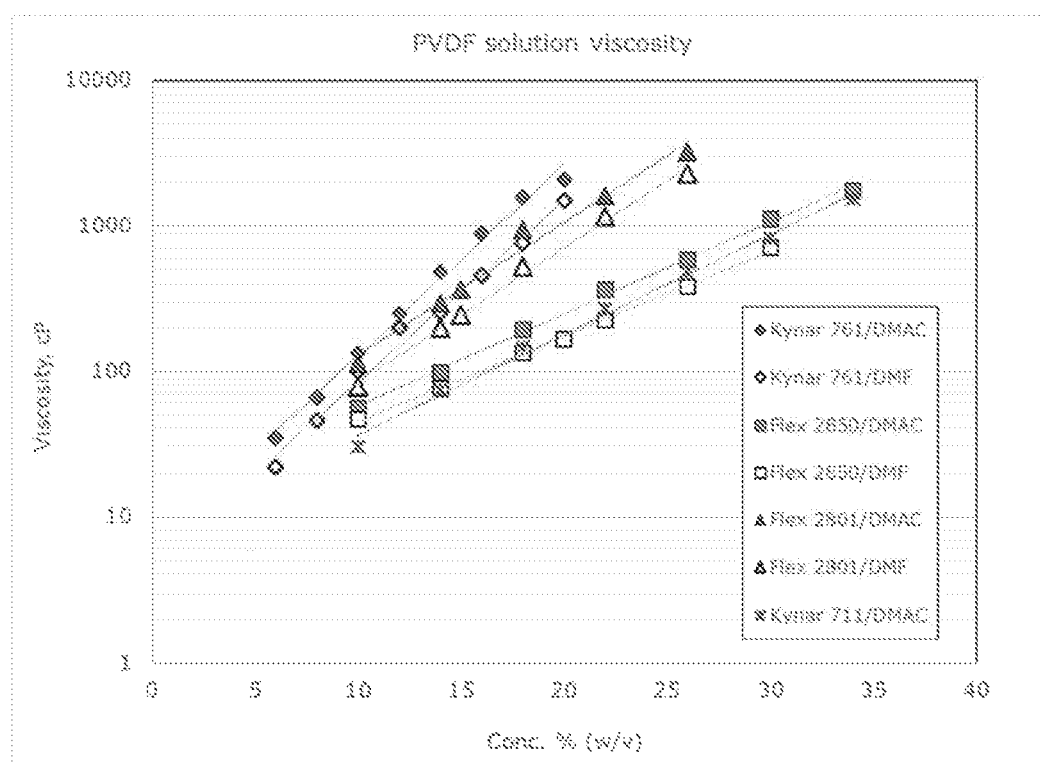
FIG. 10 shows that for various PVDF grades (Table 2), the PVDF6 (Kynar® 761) produced the highest viscosities at the lowest % w/v solutions in DMAC and DMF.
Figure 11:
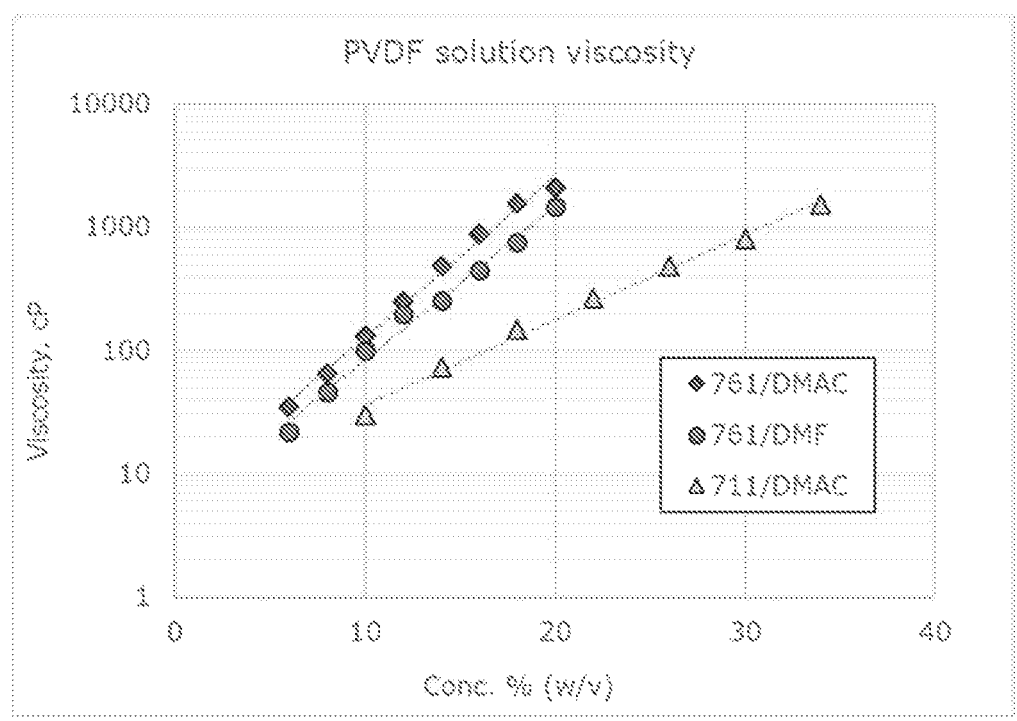
FIG. 11 shows that for PVDF6 (Kynar® 761) DMF was a better solvent than DMAC because of the lower viscosity at the same w/v % and that solution viscosity for PVDF6 is dramatically different from PVDF2 (Kynar® 711).
Figure 12:
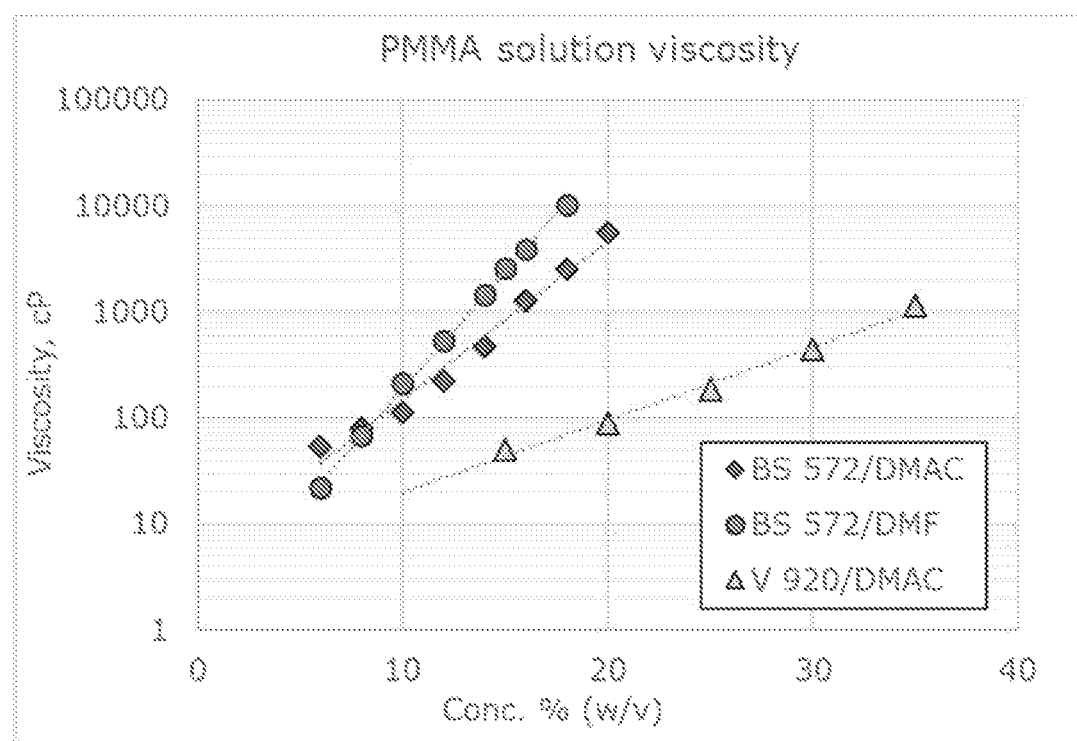
FIG. 12 shows that for the PMMA grades (Table 3), the PMMA5 (BS572) produced higher solution viscosities at lower w/v % in DMAC and DMF than the lower molecular weight PMMA1 (V920) in DMAC.
Figure 13:
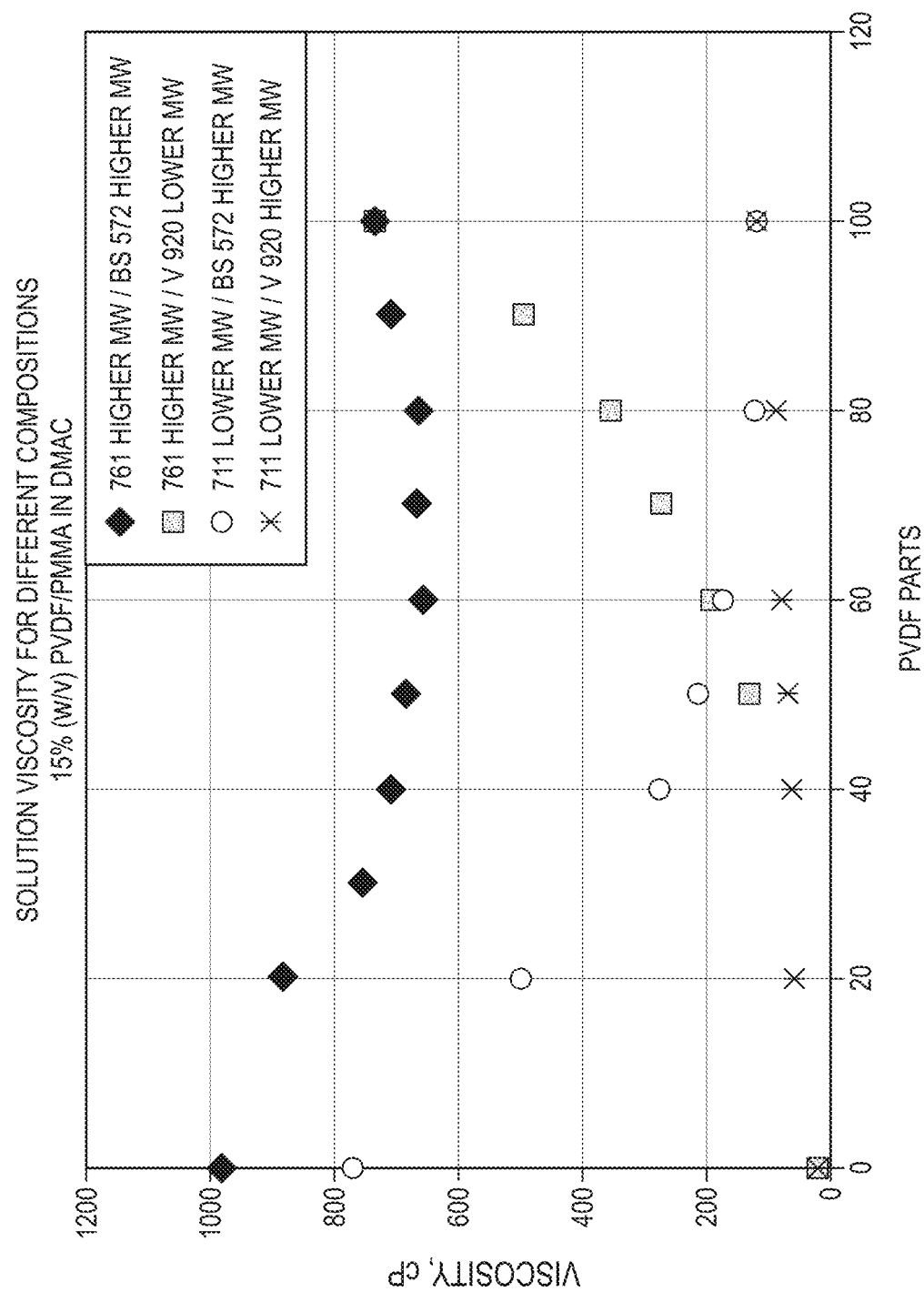
FIG. 13 shows the mix viscosities of 15% w/v solutions against the mix ratios of higher MW PMMA5 (BS572) and PVDF6 (Kynar® 761) with lower MW PMMA1 (V920) and PVDF2 (Kynar® 711).
Figure 14:
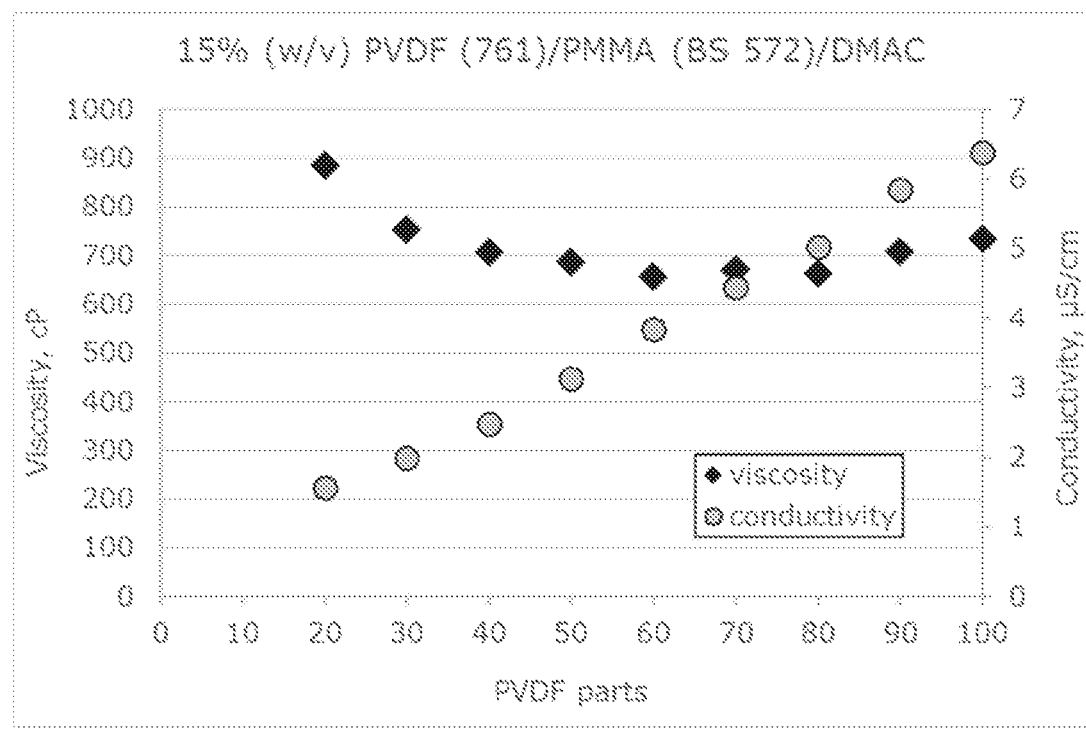
FIG. 14 shows the mix viscosities of 15% w/v solutions against mix ratios of PMMA5 (BS572) and PVDF6 (Kynar® 761) in DMAC with the solution conductivity (µS/cm) on the secondary y-axis.
Figure 15:
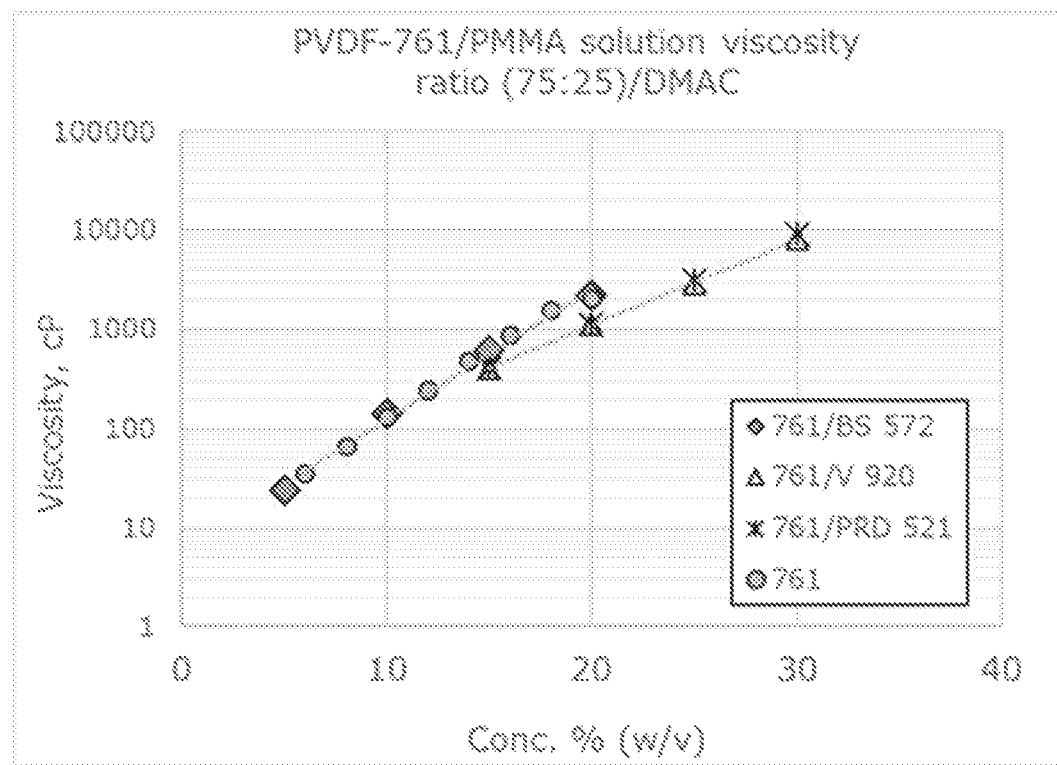
FIG. 15 shows viscosities of increasing w/v % solutions in DMAC of PVDF6 (Kynar® 761) with PMMA [PMMA1 (V920), PMMA5 (BS572), and PMMA4 (PRD521)] as viscosity modifiers in a ratio of 75:25 (PVDF6:PMMA) to verify the PMMA5 (BS572) had the largest impact on viscosity at lower w/v %.
Figure 16:
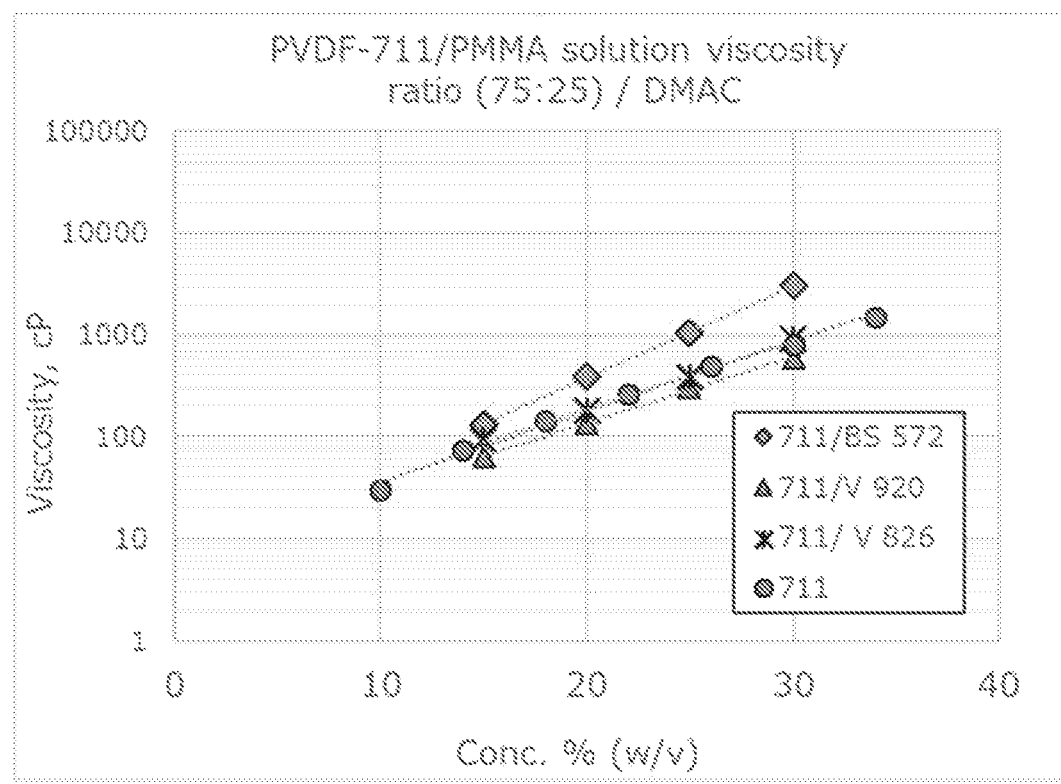
FIG. 16 shows viscosities of increasing w/v % solutions in DMAC of PVDF2 (Kynar® 711) with PMMA [PMMA1 (V920), PMMA5 (BS572), and PMMA4 (PRD521)] as viscosity modifiers in a ratio of 75:25 (PVDF2:PMMA) to verify PVDF6 was the choice for higher viscosity and that PMMA5 (BS572) had the largest impact on viscosity at lower w/v %.

PMMA and PVDF grades described in Tables 2 and 3 were further investigated for viscosity versus % w/v polymer in DMAC and DMF. FIG. 10 shows that for the PVDF grades (Table 2) the PVDF6 (Kynar® 761) produced the highest viscosities at the lowest % w/v solutions in DMAC and DMF. FIGS. 10 and 11 show that for Kynar® 761 DMF was a better solvent than DMAC because of the lower viscosity and that a dramatic solution viscosity difference from Kynar® 711 is observed. However, based on electrospinning evaluations, DMAC was a better solvent for electrospinning Kynar® 761, producing quality fibers, while DMF produced fibers with beads (FIGS. 7 and 8). PVDF2 (Kynar® 711), when electrospun at 25% w/v, in either DMAC or DMF produced fibers with beads (FIG. 8). FIG. 12 shows that for the PMMA grades (Table 3) the PMMA5 (BS572) produced higher solution viscosities at lower w/v % in DMAC and DMF than the lower molecular weight PMMA1 (V920) in DMAC. The viscosity data show that DMAC is a better solvent than DMF for BS572 because it produces lower viscosities at the same % w/v. PMMA5 (BS572) also electrospun higher quality fibers from DMAC and better than PMMA1 (V920) at even higher w/v %. Because the best solvent for PMMA and PVDF for electrospinning was DMAC, mix viscosities at varying ratios of PMMA and PVDF were evaluated for high and low MW/viscosities of PMMA and PVDF. FIG. 13 shows the mix viscosities of 15% w/v solutions versus mix ratios of higher MW PMMA5 (BS572) and PVDF6 (Kynar® 761) with lower MW PMMA1 (V920) and PVDF2 (Kynar® 711). This confirmed that PMMA5 (BS572) and PVDF6 (Kynar® 761) were the grades to choose to produce the highest viscosities at the lowest % w/v to electrospin the largest diameter fibers. FIG. 14 shows the mix viscosities of 15% w/v solutions vs mix ratios of PMMA5 (BS572) and PVDF6 (Kynar® 761) in DMAC with the solution conductivity (μS/cm) on the secondary y-axis. This illustrates that the PVDF6 (Kynar® 761) provides higher solution conductivity. FIG. 15 shows viscosities of increasing w/v % solutions in DMAC of PVDF6 (Kynar® 761) with PMMA [PMMA1 (V920), PMMA5 (BS572), and PMMA4 (PRD521)] as viscosity modifiers in a ratio of 75:25 (PVDF6:PMMA) to verify that PMMA5 (BS572) had the largest impact on viscosity at lower w/v %. FIG. 16 shows viscosities of increasing w/v % solutions in DMAC of PVDF2 (Kynar® 711) with PMMA [PMMA1 (V920), PMMA5 (BS572), and PMMA4 (PRD521)] as viscosity modifiers in a ratio of 75:25 (PVDF2:PMMA) to verify PVDF6 was the choice for high viscosity and that PMMA5 (BS572) had the largest impact on viscosity at lower w/v %. The aforementioned solution viscosities confirmed that PMMA5 (BS572) and PVDF6 (Kynar® 761) produce the highest viscosities at the lowest % w/v to electrospin the fibers with the largest diameter and best quality.

Example 3

PMMA5 (BS572) and PVDF6 (Kynar® 761) Polymers in DMAC

Figure 17:
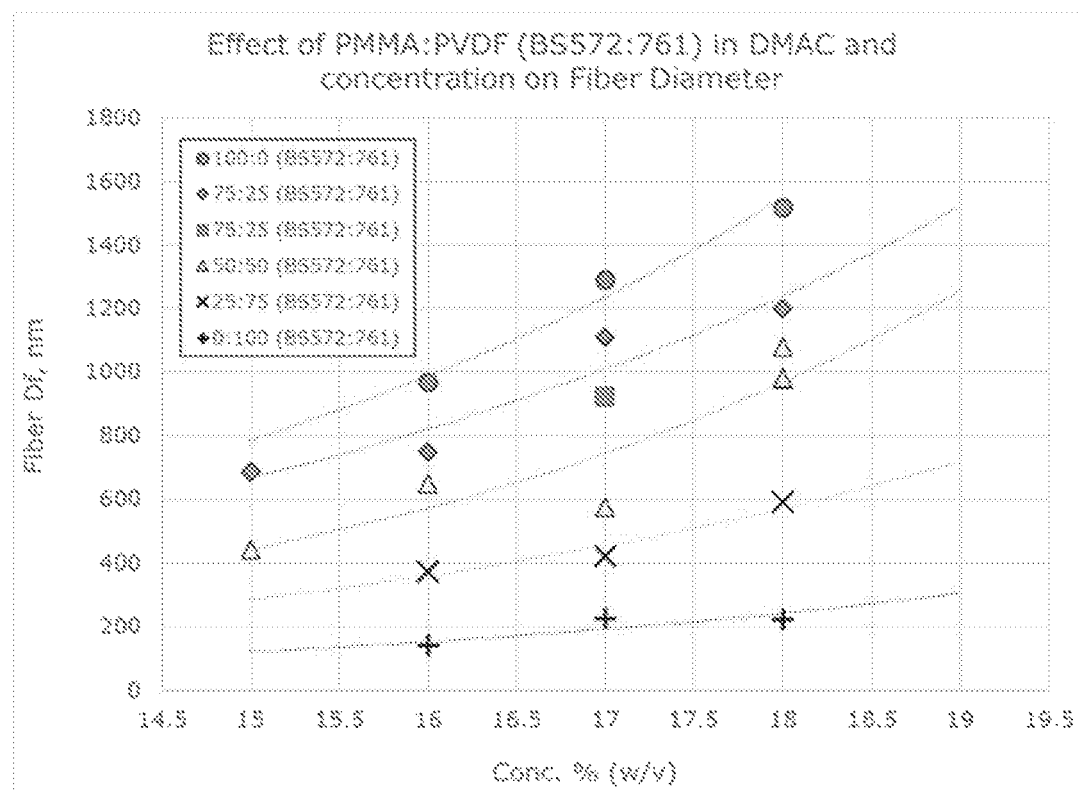
FIG. 17 shows that 15-18 w/v % solutions in DMAC of PMMA5 (BS572):PVDF6 (Kynar® 761) at mix ratios of 100:0, 75:25, 50:50, 25:75, and 0:100 can control the electrospun fiber diameters.
Figure 18:
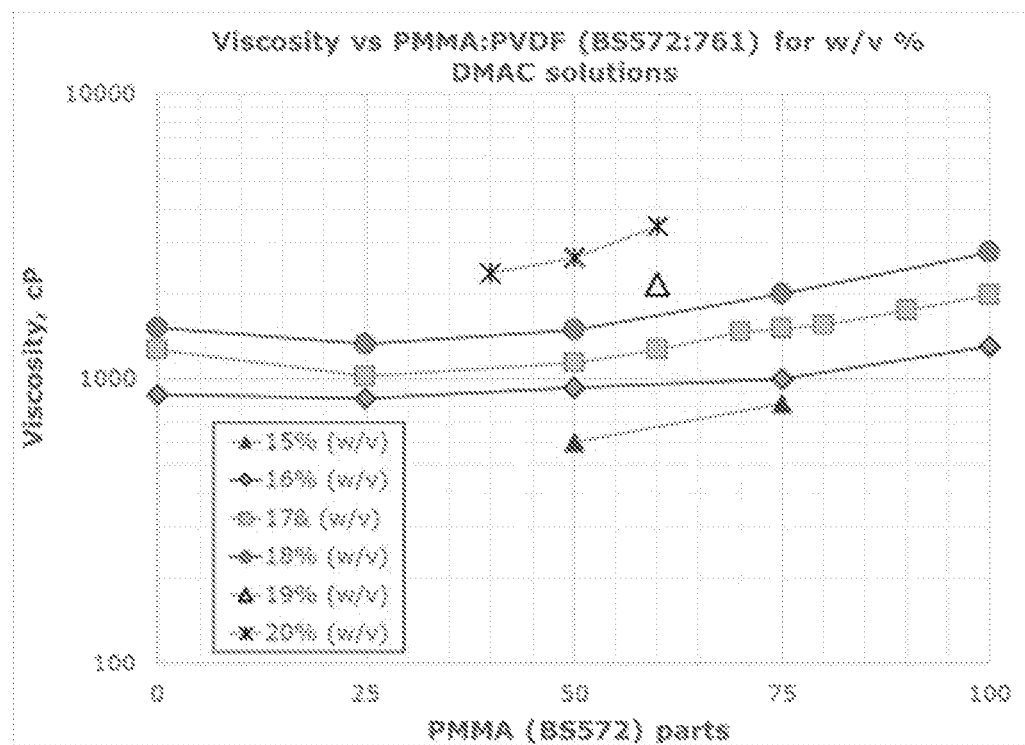
FIG. 18 shows that increasing the PMMA5 (BS572) to PVDF6 (Kynar® 761) ratio and increasing concentrations of 15-20% w/v produces higher viscosities.
Figure 19:
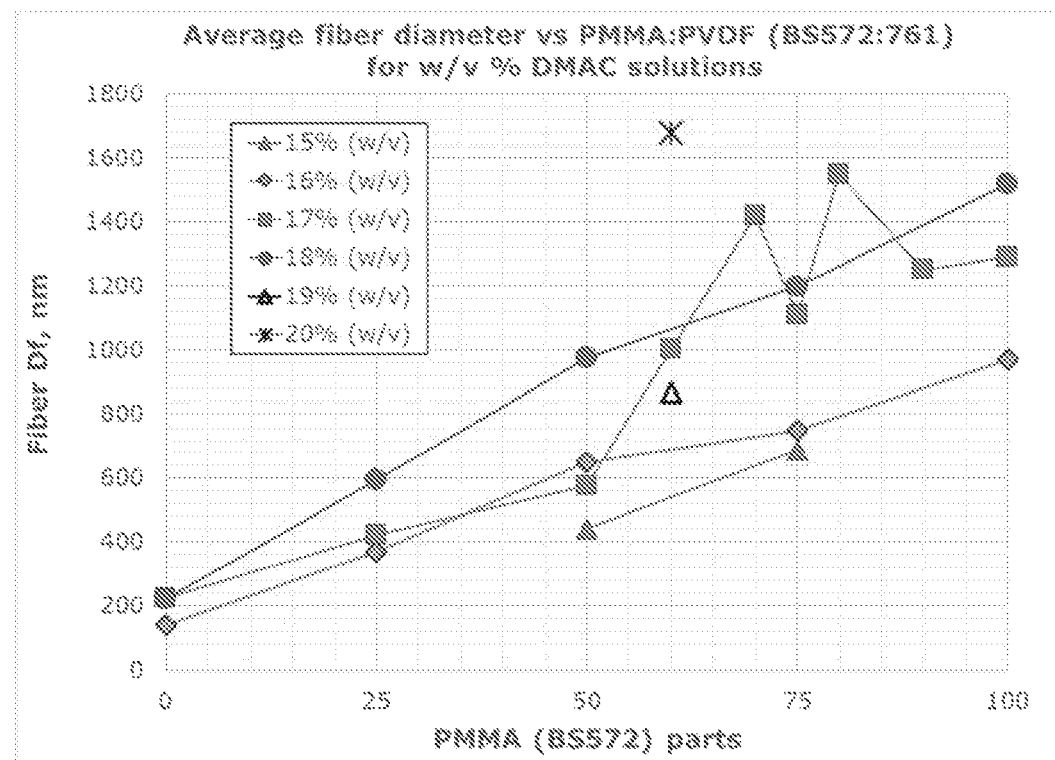
FIG. 19 shows that increasing the PMMA5 (BS572) to PVDF6 (Kynar® 761) ratio and increasing concentrations of 15-20% w/v produces higher average fiber diameters produced by electrospinning.

More investigations of viscosity and electrospinning fibers were performed once PMMA5 (BS572) and PVDF6 (Kynar® 761) were proven to be the viable polymer grades to produce fiber diameters with the resulting MFP for use in lateral flow diagnostic applications. Electrospinning was performed on the ELMARCO NS1WS500U unit from Table 1, and fibers were collected on 50 μm Melinex PET or a moving web of 100 μm LDPE at 40 cm width. Typical electrospinning parameters were ΔV of 60-100 kV, 240 mm electrode distance, 0.6 mm dispensing orifice, carriage speed of 100 mm/sec, wire speeds of 1-3 mm/sec, air in at 80 m³/hr, air out at 120 m³/hr, and spinning chamber conditions of 30-40° C. and Relative Humidity of 10-30% controlled by the use of a dehumidifier. The use of the fixed wire machine with dispensing head allows for electrospinning of higher w/v % solutions and viscosities, with the upper viscosity limitation of about 4,000 centipoise (cP). Increasing w/v % solutions of 15-18% in DMAC of PMMA5 (BS572):PVDF6 (Kynar® 761) at mix ratios of 100:0, 75:25, 50:50, 25:75, and 0:100 were made and electrospun under the aforementioned conditions to determine the resulting average fiber diameters as plotted in FIG. 17. The data illustrate that higher average fiber diameters are directly proportional to higher % w/v concentrations and higher ratios of PMMA5 (BS572) to PVDF6 (Kynar® 761). Therefore, fiber diameter and resulting pore size rating can be tuned with polymer concentration and PMMA:PVDF ratio. FIG. 18 shows that increasing the PMMA5 (BS572) to PVDF6 (Kynar® 761) ratio and increasing concentrations of 15-20% w/v produce higher viscosities. FIG. 19 shows that the trend that increases viscosity in FIG. 18 also increases the resulting average fiber diameter produced by electrospinning.

Example 4

Non-porous Film Substrate Evaluations

Figure 20:
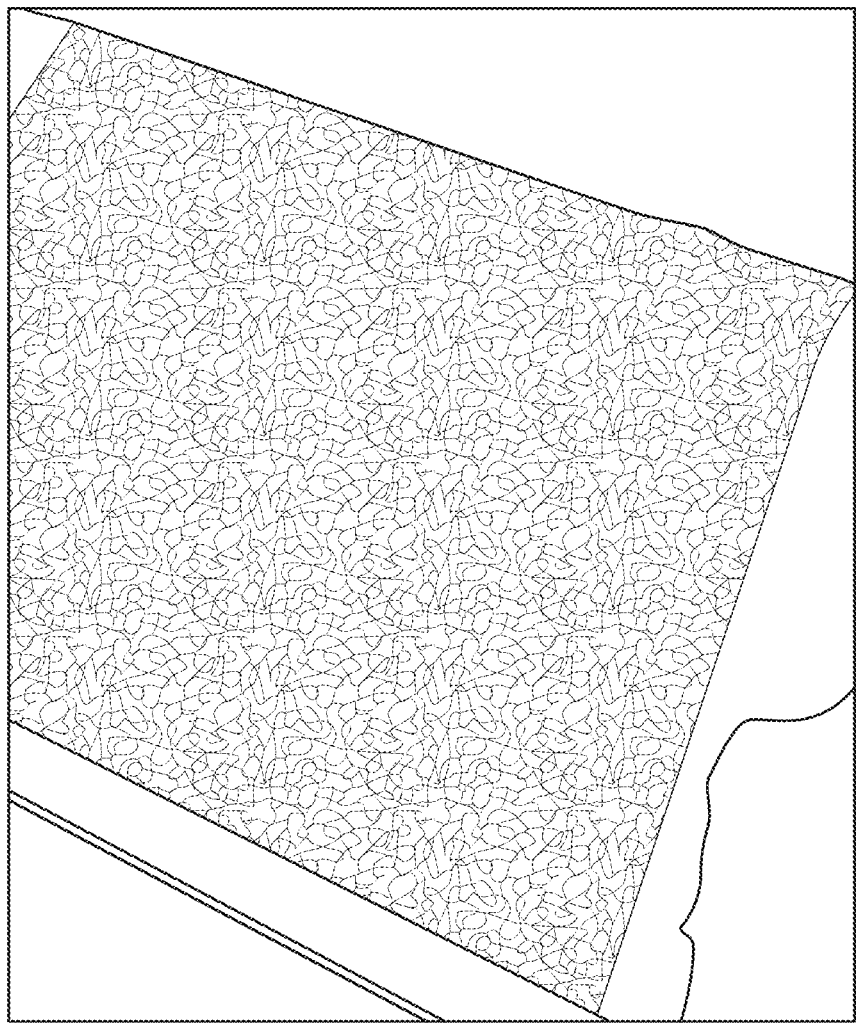
FIG. 20 shows non-uniform electrospun non-woven fiber mat electrospun on stationary Melinex® PET.
Figure 21:
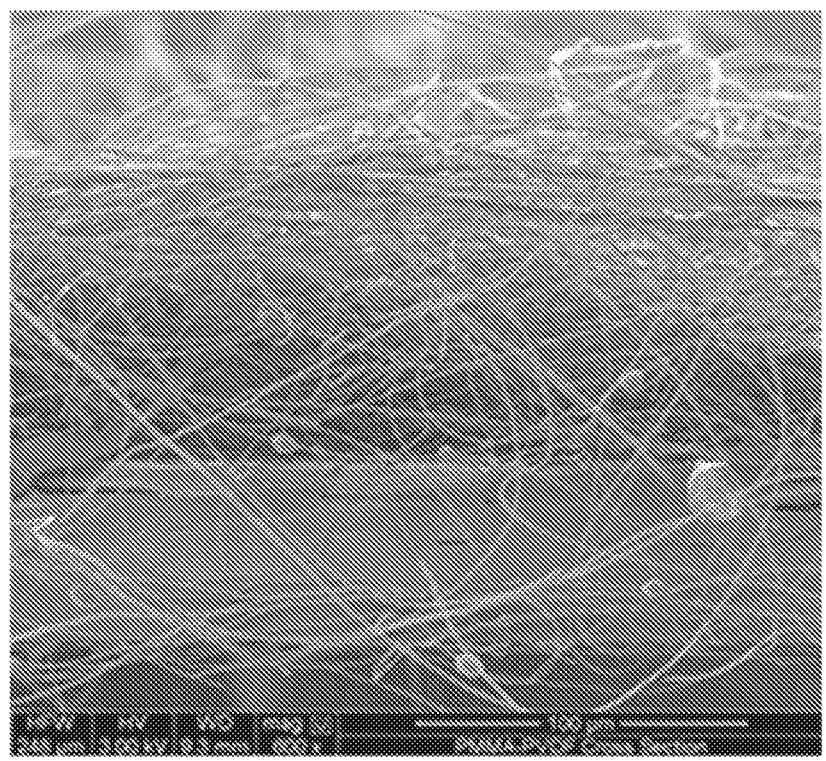
FIG. 21 shows a SEM image of a cross-section of the electrospun non-woven fiber mat quality when electrospinning on stationary Melinex® PET.

Typical air-cast nitrocellulose membranes are brittle and are therefore cast onto non-porous films such as Melinex® PET (DuPont Teijin Films Luxembourg S.A) to provide integrity and for ease of use during assembly of lateral flow diagnostic devices. Electrospun fibers are typically collected on non-woven or porous substrates that allow voltage to pass between the spinning and collecting electrodes and to provide pores for volatilized solvents to pass. Electrospinning on a non-porous substrate or film presents challenges in producing substantial fiber mat thickness, forming uniform coatings, and causing incomplete solvent evaporation or drying of fiber mats. When trying to electrospin a solution of 17% w/v PMMA5 (BS572):PVDF6 (Kynar® 761) in DMAC with a viscosity of about 1500 cP on stationary Melinex® PET, the film became highly electrically charged and the electrospun non-woven fiber mat was non-uniform (FIG. 20). Also, the maximum fiber mat thickness and fiber packing quality were limited (FIG. 21). FIG. 20 shows a center area on the Melinex® PET that was in-line with the electrodes with less fiber coverage. FIG. 20 also shows how the fibers coat the film with a pattern of the electric field trying to go around the film. FIG. 21 shows a SEM image cross-section of the electrospun fibers with poor fiber mat packing on the Melinex® PET film, which is likely a result of the electrical charging of the film. Electrospinning was performed on the ELMARCO NS1WS500U unit from Table 1, and fibers were collected on 50 μm Melinex PET. The typical electrospinning parameters were ΔV of 100 kV, 240 mm electrode distance, 0.6 mm dispensing orifice, carriage speed of 100 mm/sec, wire speeds of 1-3 mm/sec, spinning chamber conditions of 30-40° C., and Relative Humidity of 10-30% controlled by the use of a dehumidifier.

Typically, polymeric films have surface electrical resistivity in Ω/sq from conductive ($10^1$-$10^4$), static dissipative ($10^6$-$10^{12}$), anti-static ($10^{10}$-$10^{12}$), to insulating ($>10^{12}$). Volumetric resistivity is in Ω-cm, obtained by multiplying sheet resistance by thickness. Resistivity can be measured using test method ANSI/ESD STM 11.11.

In certain embodiments, the methods provided herein include electrospinning on non-porous substrates, such as polymer films, which presents challenges of the polymer film's inherent electrical resistivity, polymer chemistry, crystallinity, and solubility. Polymer films need to be insoluble in the electrospinning solvent and need minimal to no electrical charging to allow for safe moving web operation and to enable well packed and uniform fiber mats. A film that does not electrically charge not only allows for moving web collection but also the ability to run at higher voltages. Table 5 is a detailed table of the non-porous films screened in the aforementioned electrospinning conditions. The list is in order of increasing electrical resistance, where Melinex® 401 PET has a higher resistance and resulted in poor performance as an electrospinning substrate (FIGS. 20 and 21).

TABLE 5

Table of non-porous polymeric films screened in order of increasing electrical resistivity. Lists product codes, manufacturer, polymer type, thickness, electrical resistivity, and observed electrical charging when placed in the electric field during electrospinning.

| ID # | Product code | Manufacturer | Polymer | Thickness (μm) | Surface resistivity Sheet/Volume (Ω/sq) | Bulk Resistivity (Ω · cm) | static charging | comments/ solvent compatibility |
|---|---|---|---|---|---|---|---|---|
| 1 | Linqstat XVCF | Caplinq (Canada) | Polyethylene (PE) w/carbon | 70 | 500 | 3.5 | none | |
| 2 | Linqstat MVCF | Caplinq (Canada) | Polyethylene (PE) w/carbon | 100 | $5 \times 10^4$ | 500 | none | |

TABLE 5-continued

Table of non-porous polymeric films screened in order of increasing electrical resistivity. Lists product codes, manufacturer, polymer type, thickness, electrical resistivity, and observed electrical charging when placed in the electric field during electrospinning.

| ID # | Product code | Manufacturer | Polymer | Thickness (μm) | Surface resistivity Sheet/Volume (Ω/sq) | Bulk Resistivity (Ω · cm) | static charging | comments/ solvent compatibility |
|---|---|---|---|---|---|---|---|---|
| 3 | Linqstat VCF | Caplinq (Canada) | Polyethylene (PE) w/carbon | 50 | $2 \times 10^5$ | 1000 | none | |
| 4 | Kapton ® XC | DuPont (USA) | Polyimide (PI) w/carbon | 25 | $5 \times 10^5$-$5 \times 10^7$ | 1250-125000 | none | |
| 5 | PE700ASPL | Wiman film (RTP company MN, USA) | Low density polyethylene (LDPE) w/anti-stat | 200 | $1.5 \times 10^9$ | $3 \times 10^7$ | none | |
| 6 | RTP199X138766BZEG | Wiman film (RTP company MN, USA) | Polypropylene (PP) w/anti-stat | 100 | $1.5 \times 10^9$ | $1.5 \times 10^7$ | none | |
| 7 | PE700AS | Wiman film (RTP company MN, USA) | LDPE w/anti-stat | 100 | $1 \times 10^{10}$-$1 \times 10^{11}$ | $1 \times 10^8$-$1 \times 10^9$ | none | |
| 8 | PermaStat | Wiman film (RTP company MN, USA) | Acrylonitrile Butadiene Styrene (ABS) w/anti-stat | 150 | $1 \times 10^9$ | $1.5 \times 10^7$ | none | |
| 5b | PE700ASPL | Wiman film (RTP company MN, USA) | PermaStat Plus LDPE | 107 | $2.7 \times 10^{10}$ | $2.9 \times 10^8$ | none | |
| 6b | RTP199X138766BZEG | Wiman film (RTP company MN, USA) | PermaStat Plus PP | 122 | $2.1 \times 10^{10}$ | $2.6 \times 10^8$ | none | |
| 7b | PE700AS | Wiman film (RTP company MN, USA) | PermaStat LDPE | 104 | $2.2 \times 10^{11}$ | $2.3 \times 10^9$ | none | |
| 8b | ABS6600 | Wiman film (RTP company MN, USA) | PermeStat ABS | 127 | $9.0 \times 10^{11}$ | $1.1 \times 10^{10}$ | none | |
| 9 | 8539K201 | McMaster-Carr (NJ, USA) | Nylon | 50 | $5 \times 10^{10}$ | $2.5 \times 10^8$ | none | |
| 10 | 8327K11 | McMaster-Carr (NJ, USA) | static dissipative UHMWPE | 125 | | | none | |
| 11 | 564936664 | Elmarco (Liberec, Czech Republic) | PP spunbond with antistatic treatment | | | | none | |
| 12 | LDPE | AMCOR Flexibles (Spain) | LDPE | 100 | $1 \times 10^{13}$ | $1 \times 10^{11}$ | none | |
| 13 | 85585K102 | McMaster-Carr (NJ, USA) | Polycarbonate | 125 | $1 \times 10^{15}$ | $1.25 \times 10^{13}$ | medium | |
| 14 | 7538T11 | McMaster-Carr (NJ, USA) | Duralar ® (silver PET) | 50 | | | medium | |
| 15 | 85655K11 | McMaster-Carr (NJ, USA) | UHMWPE | 100 | | | medium | |
| 16 | 87875K91 | McMaster-Carr (NJ, USA) | Polyvinylchloride (PVC) | 125 | | | medium | |
| 17 | Melinex ® 401 | DuPont Tejin Films (Luxembourg) | Polyethylene terephthalate (PET) | 50 | $1 \times 10^{16}$ | $5 \times 10^{13}$ | high | |
| 18 | EUROPLEX ® Film HC 99710 | Evonik Cyro (NJ, USA) | Polymethylmethacrylate (PMMA) and Polyvinylidene difluoride (PVDF) | 45 PMMA, 5 PVDF | $1 \times 10^{14}$ | $5 \times 10^{11}$ | medium | no DMF/ DMAC |
| 19 | ACRYLITE ® Film 0F072 | Evonik Cyro (NJ, USA) | PMMA | 75 | $1 \times 10^{14}$ | $7.5 \times 10^{11}$ | medium | no DMF/ DMAC |

Figure 22:
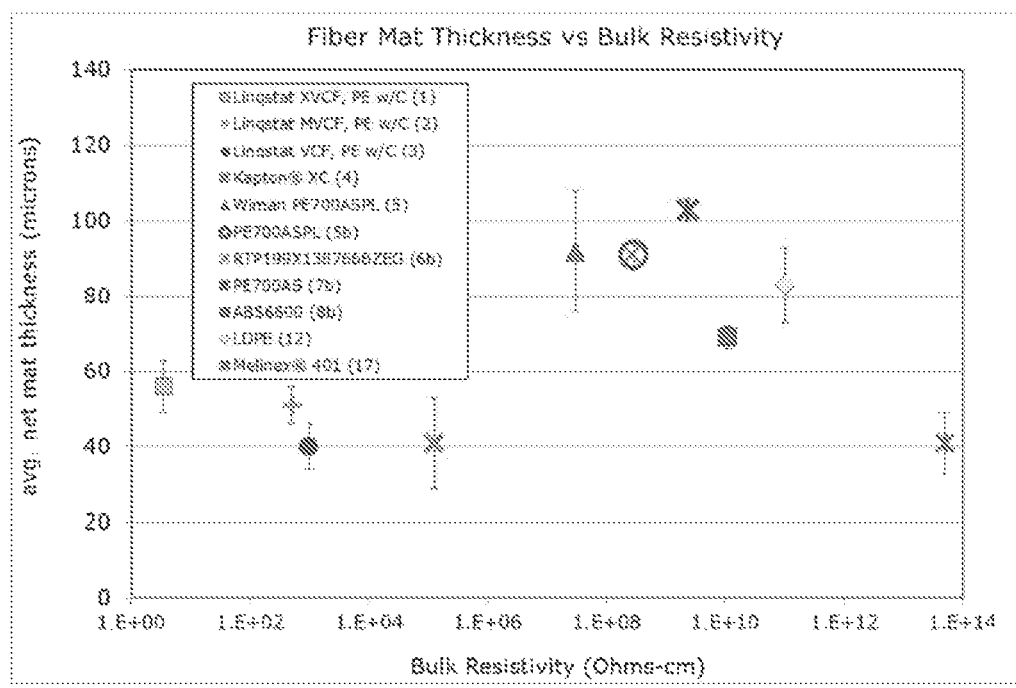
FIG. 22 shows the plot of fiber mat thickness or productivity vs substrate bulk electrical resistivity.

Non-porous films with electrical resistance in the static dissipative to anti-static region with low crystallinity, low dielectric strength, and non-polar chemistry are preferred substrates for electrospinning on fiber mats. Certain preferred substrates are polymer films of LDPE, Nylon, UHMWPE, or polymer composites with anti-static or static dissipative additives or conductive carbon. Poor non-porous film substrates for electrospinning that exhibited high electrical charging included PET, PVC, and PC polymers. The polymers PMMA and PVDF exhibited moderate electrical charging under typical electrospinning conditions. FIG. 22 shows a selection of the films from Table 5 with increasing bulk resistivity and the maximum thickness of the fiber mat generated under the same aforementioned electrospinning conditions over the same spinning time of 10 minutes and film width of 40 cm. FIG. 22 shows films 5, 5b-8b, and 12 from Table 5 electrospun under the same conditions also produced thicker mats than films with lower or higher resistivity of about $10^7$-$10^{12}$ Ω-cm from FIG. 22. Spinning conditions for FIG. 22 were 17% PMMA:PVDF (70:30) in DMAC, 100 kV, 240 cm distance, 2 cm/min line speed, 42° C., 4° C. dew point, where all produced fiber diameters of about 900 nm. Table 5 and FIG. 22 indicate a region of bulk electrical resistivity of about $10^8$-$10^{12}$ Ω-cm has maximum productivity in terms of non-woven fiber mat thickness and no electrical charging of the film. This discovery allows for moving web collection, fiber mat uniformity, thickness productivity, and fiber packing quality. When the substrates were too conductive, asymmetric currents were observed at the spinning and collecting electrodes.

Figure 23:
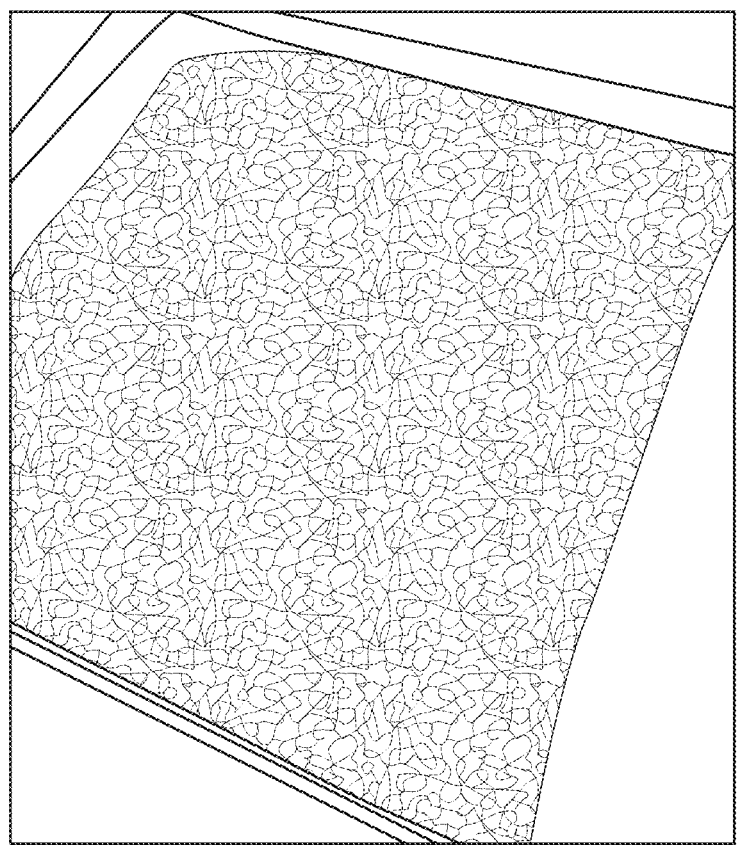
FIG. 23 shows an image of electrospun non-woven fiber mat membrane electrospun on a stationary LDPE film (#12 in Table 5).

Switching to LDPE as the non-porous substrate (#12 in Table 5) allowed for more uniform mats with the LDPE stationary (FIG. 23) compared to Melinex® PET in FIG. 20. LDPE film also produced greater productivity of about 90

μm fiber mat thickness and better fiber packing quality (FIG. 24) compared to Melinex® PET in FIG. 21 under the same electrospinning conditions. Similar results in terms of no film electrical charging, higher productivity, better uniformity, and fiber packing occurred for film ID #s 5 through 12 and 5b-8b in Table 5. FIG. 25 shows the electrospun non-woven fiber mat coated onto the LDPE film with a moving web line speed of 2 cm/min on the outside of the ELMARCO NS1WS500U unit from Table 1. FIGS. 26.1 and 26.2 show SEM images of the air and LDPE sides where similar fiber quality and diameters are observed, indicating that the resulting membrane is symmetrical in terms of pore rating on both sides.

The non-porous substrate used for fiber collection can also function as a permanent support when the fibers have high adhesion to the film surface through surface treatment methods, such as corona, plasma, etching, or roughening or by film chemistry or solvent bonding to the substrate. For example, film #18 in Table 5 can be used or a thin layer of 5 μm polymer that is partially soluble in the electrospinning solvent can be used to solvent bond the fibers to the film substrate. Alternatively, the electrospun non-woven fiber mat membrane can be electrospun onto a film that allows for removal and potential for use of the membrane as an unbacked membrane. This can also be transferred to an alternative film. The transfer option then allows for substrate film of choice (for optical requirements, thickness, etc.); and adhesion can be achieved through, for example, lamination, adhesive, and solvent bonding. Non-woven fiber mats made using electroblowing can be collected onto porous substrates and as aforementioned with electospinning then used in assays unbacked or after transfer to a substrate film.

Example 5

Effect of Relative Humidity/Dew Point on Electrospun Fiber Diameter

Figure 27:
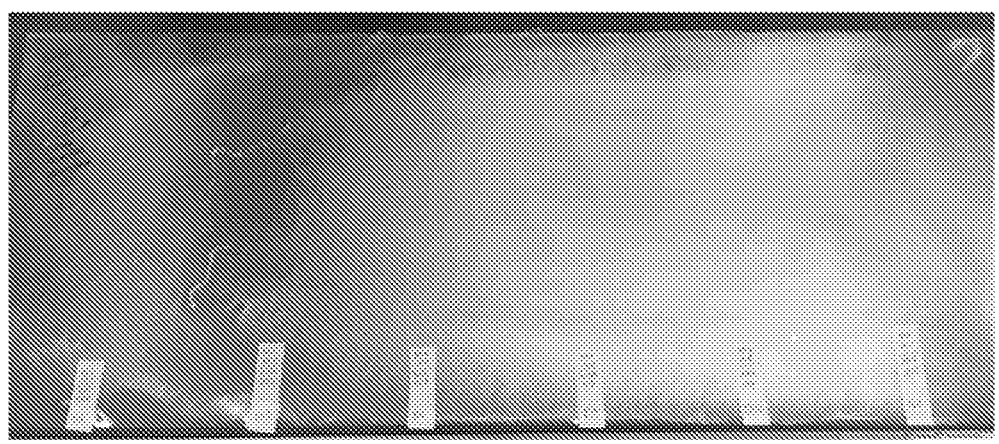
FIG. 27 shows the electrospun fiber mat produced from 17% w/v PMMA5 (BS572):PVDF6 (Kynar® 761) in DMAC at a ratio of 60:40 against decreasing humidity from left to right.
Figure 29:
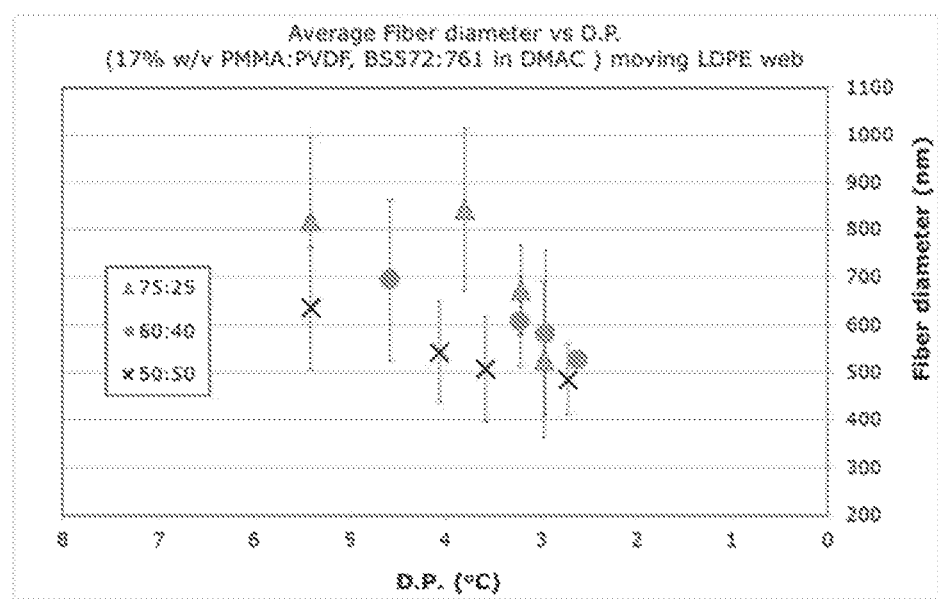
FIG. 29 shows a plot of average fiber diameters against decreasing dew points obtained by electrospinning 17% w/v solutions of PMMA5 (BS572):PVDF6 (Kynar® 761) at ratios of 75:25, 60:40, and 50:50 in DMAC by collecting on moving LDPE webs with reducing humidity.
Figure 30:
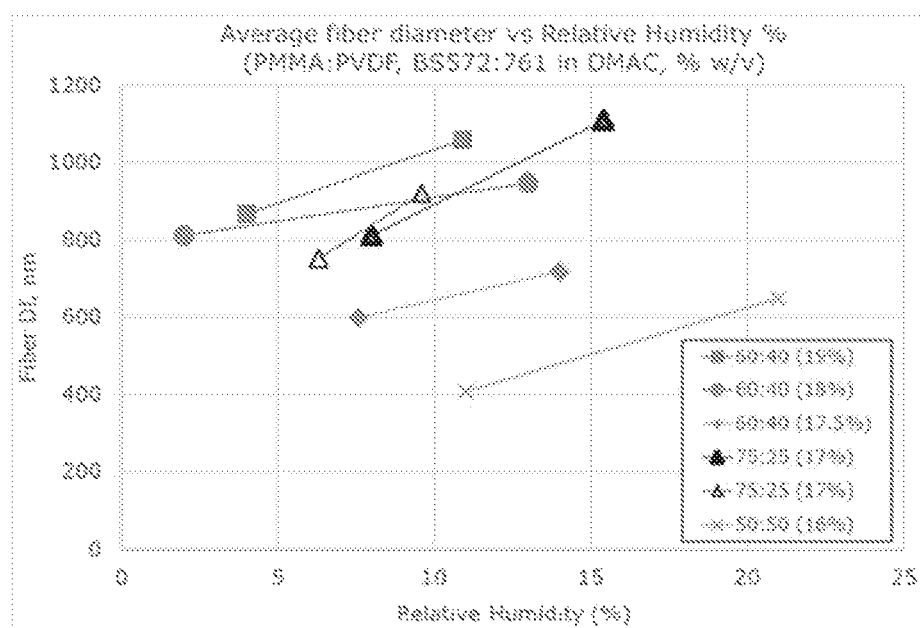
FIG. 30 shows a plot of electrospun average fiber diameters of various w/v % solutions and ratios of PMMA5

Fiber diameter produced by electrospinning was sensitive to the relative humidity or dew point in the electrospinning chamber. Higher relative humidity or dew points produced larger average fiber diameters for the same polymer solutions in terms of w/v % and PMMA:PVDF ratios when electrospun under the same electrospinning parameters. To demonstrate this effect, an experiment with a moving web was conducted to show the effect of relative humidity or dew point on the average fiber diameter. The moving web experiment was conducted under the previously mentioned electrospinning parameters at a line speed of 5 cm/min on LDPE at a starting temperature of 22° C. and relative humidity of about 50%. To determine the effect of the internal spinning chamber relative humidity, a dehumidifier plumbed into the inlet of the spinning chamber was turned on; and dew point was tracked against line speed and location. Solutions of 17% w/v of PMMA5 (BS572):PVDF6 (Kynar® 761) at ratios of 75:25, 60:40, and 50:50 in DMAC were electrospun and collected on moving webs with reducing humidity to determine the effect of dew point on the average fiber diameter. Average fiber diameters were measured at the different calculated dew points using SEM to show that higher dew points produced higher average fiber diameters. FIG. 27 shows an image of the fiber mat produced from the 60:40 PMMA:PVDF ratio with decreasing humidity shown from left to right. FIGS. 28.1, 28.2, and 28.3 show SEM images of the fiber quality and diameters produced at approximate dew points of 11.8° C., 3.2° C., and 2.6° C. FIG. 28.1 at 11.8° C. shows how the dew point was too high to produce dry and well-formed fibers, while FIGS. 28.2 and 28.3 show well-formed fibers of decreasing diameter with dew point. FIG. 29 is a plot of the average fiber diameters against decreasing dew point obtained by electrospinning 17% w/v solutions of PMMA5 (BS572):PVDF6 (Kynar® 761) at ratios of 75:25, 60:40, and 50:50 in DMAC by electrospinning and collecting on a moving web with reducing humidity. FIG. 30 is a plot of electrospun average fiber diameters of various w/v % solutions and ratios of PMMA5 (BS572):PVDF6 (Kynar® 761) at two different relative humidities produced by the same electrospinning parameters.

FIGS. 29 and 30 demonstrate that average fiber diameter is a function of w/v %, PMMA:PVDF ratio and relative humidity or dew point. This means the resulting MFP of electrospun non-woven fiber mats can be controlled through these three factors.

Example 6

Line Speed, Productivity, and Mat Thickness Uniformity

Electrospun non-woven fiber mat membranes collected on non-porous substrates also need to have productivity in terms of mat thickness versus line speed and thickness uniformity to function as membranes in lateral flow diagnostic assays. As shown in FIG. 6, contributing factors to mat membrane productivity and uniformity are the polymer solution (%, ratio), electrospinning parameters, dew point, and film substrate.

Electrospinning was performed on the ELMARCO NS1WS500U unit from Table 1, and fibers were collected on a moving web of 100 μm thick LDPE film (#12 in Table 5) at 40 cm width. Typical electrospinning parameters were ΔV of 60-100 kV, 240 mm electrode distance, 0.6 mm dispensing orifice, carriage speed of 100 mm/sec, wire speeds of 1-3 mm/sec, air in at 80 $m^3$/hr, air out at 120 $m^3$/hr, and spinning chamber conditions of 30-40° C. and relative humidity of 10-30% controlled by a dehumidifier. Table 6 details a series of experiments where the same solution (17% w/v of PMMA5 (BS572):PVDF6 (Kynar® 761) at ratio of 75:25 in DMAC) was electrospun at different voltage differences (ΔV) at the same line speed or fixed ΔV and different substrate line speeds. Samples 072016-1 to -4 were electrospun at 60 kV and line speeds of 0.5, 1.0, 2.5, and 5.0 cm/min. Samples 072016-4 to -6 were electrospun at 5.0 cm/min and voltages of 60, 80, and 100 kV. Average electrospun non-woven fiber mat thicknesses were measured and reported in microns (μm) by making 5 micrometer measurements across a 1×4 cm sample area and subtracting out the film thickness. Basis weight in $g/m^2$ was determine by measuring the mass of the 1×4 cm strip, subtracting the mass of the film, and dividing by the $4 \times 10^{-4}$ $m^2$ area. FIG. 31 shows the linearity of average net electrospun fiber mat thickness vs basis weight for the several conditions of voltage and line speeds in Table 6. Slower line speeds produced thicker mats and higher basis weight. 60 kV at decreasing line speeds produced a similar slope of fiber packing as the fixed line speed and increasing voltage. 100 kV produced higher fiber packing than 60 kV at slower line speeds.

TABLE 6

Sample descriptions that were electrospun at different
delta voltages or substrate collecting line speeds.

| Sample ID | Delta V (kV) | Line speed (cm/min) | average fiber diameter (nm) | Thickness (μm) | Basis weight (g/m$^2$) |
|---|---|---|---|---|---|
| 072016-1 | 60 | 0.5 | 632 ± 212 | 93 ± 6 | 13.8 |
| 072016-2 | 60 | 1.0 | 697 ± 193 | 89 ± 10 | 13.0 |
| 072016-3 | 60 | 2.5 | 734 ± 236 | 50 ± 5 | 9.3 |
| 072016-4 | 60 | 5.0 | 674 ± 201 | 29 ± 5 | 7.8 |
| 072016-5 | 80 | 5.0 | 609 ± 163 | 37 ± 4 | 8.5 |
| 072016-6 | 100 | 5.0 | 612 ± 162 | 41 ± 3 | 9.0 |

FIG. 32 is an image of the sampling area (60×40 cm) and locations cross and down-web used to measure thickness productivity and uniformity. FIG. 33.1 is a plot of the average net mat thickness and basis weight for the solution and constant 60 kV voltage vs 1/line speed electrospinning experiments collected on a moving web of 100 μm thick LDPE film (#12 in Table 5) detailed in Table 6. Both the average net mat thickness and basis weight show that at 60 kV the productivity peaks at a line speed of 1.0 cm/min. FIG. 33.2 is a plot of the average net mat thickness of the aforementioned experiment at constant 60 kV voltage vs 1/line speed collected on a moving web of 100 μm thick LDPE film (#12 in Table 5) overlayed with mats electrospun under identical conditions with the exception of 100 kV onto a moving web of Permastat LDPE PE700AS film (#7b in Table 5). FIG. 33.2 shows that higher productivity or thickness can be achieved on the lower resistance film (#7b vs #12 in Table 5) at higher voltage and faster or the same line speeds. FIG. 34 is a plot of thickness and uniformity of the sample locations detailed in FIG. 32 for the solution and constant line speed vs voltage electrospinning experiments detailed in Table 6. Increasing voltage increased fiber mat thickness with similar cross and down-web uniformity up to about 40 micron thick mats. FIG. 35 is a plot of mat thickness and uniformity of the sample locations detailed in FIG. 32 for the solution in Table 6 at 100 kV against line speed. In this case, faster line speeds or lower mat thickness favored better cross and down-web uniformity; however, slower speeds allowed for thicker mat collection. FIGS. 36.1 to 36.3 shows SEM cross-section images of the samples from FIG. 35 with good correlation of micrometer-measured mat thickness and the observed SEM image cross-section thickness. Productivity in terms of mat thickness or line speed can also be increased through the use of manufacturing machines with more spinning and collecting electrodes, like the ELMARCO NS8S1600U shown in Table 1.

Example 7

Acetone as a Co-Solvent

Table 7 details formulations of lower w/v % of PMMA5 (BS572):PVDF6 (Kynar® 761) at ratio of 75:25 in DMAC with added acetone as a co-solvent and lower resulting viscosities can be used to electrospin larger fiber diameters at lower voltage of 30 kV. The use of a higher vapor pressure co-solvent allows for lower solution viscosities, faster solvent evaporation during electrospinning to produce larger diameter fibers, and the ability to electrospin quality fibers at higher relative humidities by aiding in the volatilization of the lower vapor pressure DMAC solvent. FIG. 37 is a sample SEM image of 733±263 nm fibers electrospun at 30 kV from 14% w/v PMMA5 (BS572):PVDF6 (Kynar® 761) at ratio of 75:25 in 90:10 DMAC:acetone at a temperature of 35° C. and 45% relative humidity.

TABLE 7

Lower w/v % solutions of PMMA:PVDF with DMAC and acetone as a co-solvent. Fibers with larger diameters can be electrospun with lower w/v % and viscosities by using smaller percentages of a solvent with higher vapor pressure.

| PMMA:PVDF (75:25) % w/v | DMAC (parts) | Acetone (parts) | Viscosity (cP) | voltage (kV) | average fiber diameter (nm) |
|---|---|---|---|---|---|
| 10 | 80 | 20 | 110 | 30 | 1600 |
| 10 | 75 | 25 | 99 | 30 | 1700 |
| 12 | 80 | 20 | 245 | 30 | 2200 |
| 12 | 75 | 25 | 207 | 30 | 3800 |
| 14 | 90 | 10 |  | 30 | 733 |
| 14 | 75 | 25 | 443 | 30 | 1490 |

Example 8

Electrospun Non-woven Fiber Mat Membrane Properties

Figure 24:
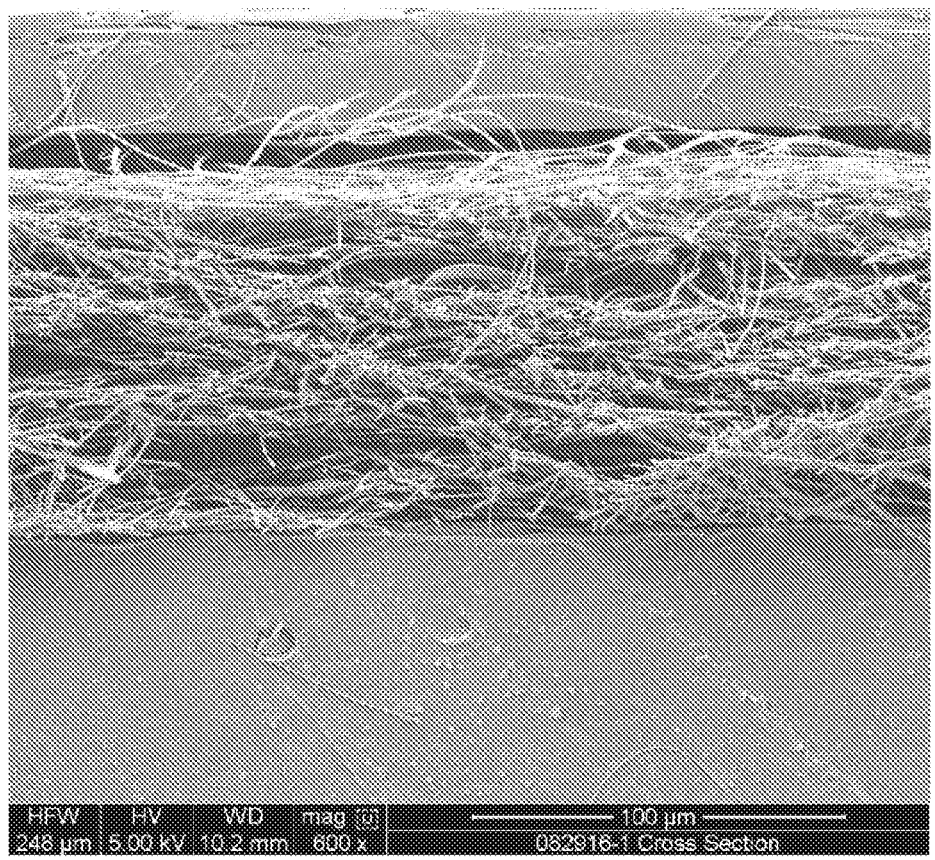
FIG. 24 shows an SEM image cross-section of electrospun fibers on LDPE film (#12 in Table 5) with productivity of about 90 µm fiber mat thickness and better fiber packing quality compared to Melinex® PET of FIG. 21 under the same electrospinning conditions.
Figure 25:
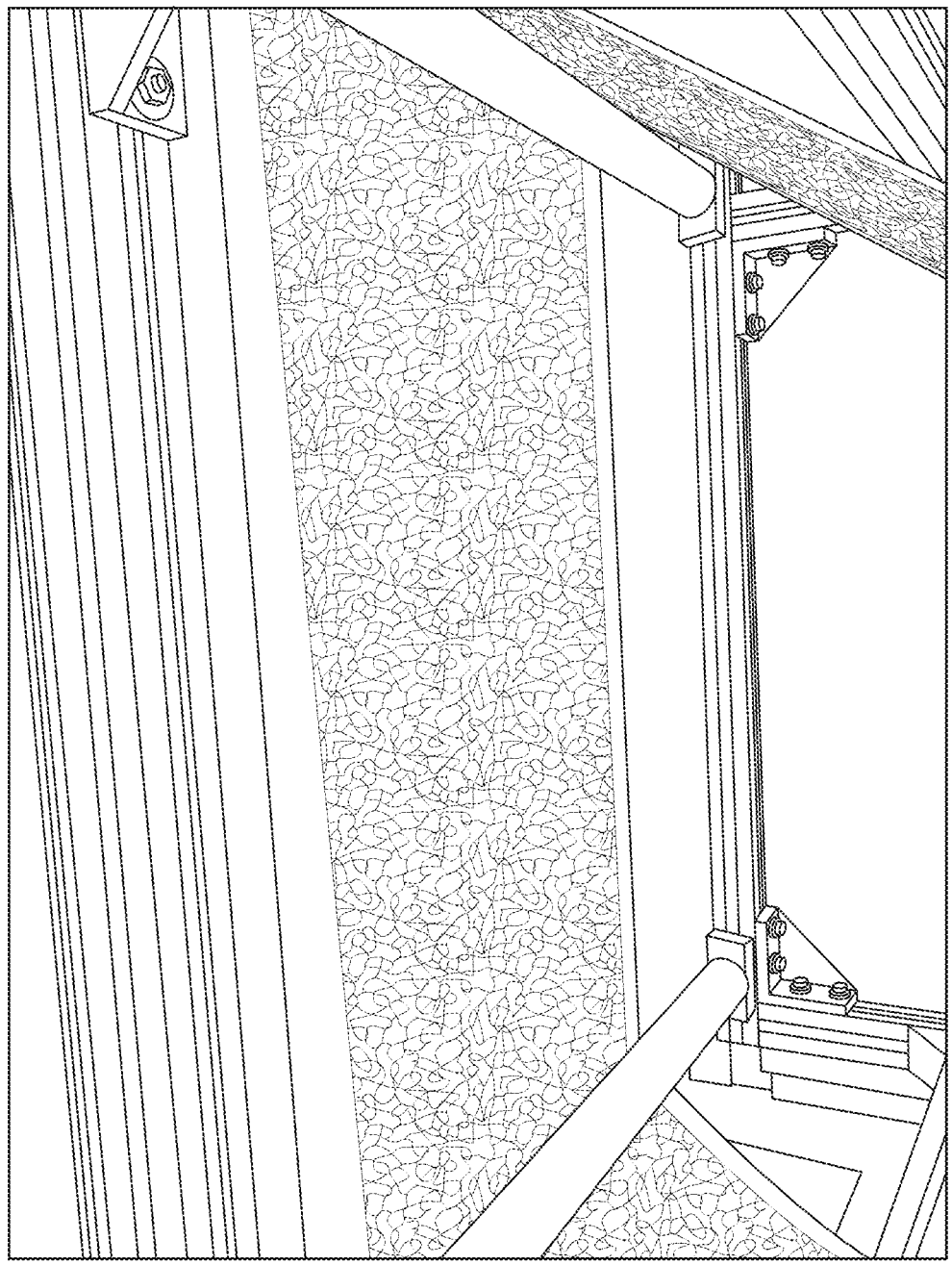
FIG. 25 shows an image of the electrospun non-woven fiber mat coated onto the LDPE film with a moving web line speed of 2 cm/min on the outside of the ELMARCO NS1WS500U unit from Table 1.

The electrospun non-woven fiber mat membranes provided herein have a structurally different 3-dimensional morphology compared to the air-cast membranes (FIG. 24 compared to FIG. 3.2). In the electrospun fiber mat membranes provided herein, the porosity results from non-woven overlapping of polymer fibers with sub- to micron sized average fiber diameters that proportionally produce the pore size diameter ratings. Conventional lateral flow diagnostic membranes are typically composed of nitrocellulose and are brittle. Also, since conventional lateral flow diagnostic membranes are air-cast onto non-porous substrates it makes it challenging to characterize them through traditional membrane techniques such as porometry. Typically, electrospinning produces nanofibers with average fiber diameters <500 nm. Provided herein are electrospun non-woven fiber mat membranes with average fiber diameters of about 500 to 1000 nm producing resulting MFP of higher than 2 microns and porosity greater than 85%. These parameters can make thicknesses of non-woven fiber mat membranes with the useful properties desired in the lateral flow diagnostics assays. Other technologies, such as solvent blowing or electroblowing that produce similar fiber diameters and mats, can be used to form similar lateral flow diagnostic membranes.

Some of the benefits of the electrospun non-woven fiber mats over air-cast nitrocellulose can be explained by the membranes' inherent physical properties. Examples of the membrane characteristics that can be compared are average fiber diameter, MFP, porosity, thickness, uniformity, shrinkage on wetting and drying, mechanical strength, adhesion to substrates, or ability to be unbacked and transferred to film support, CFT, surface area, ratio of internal polymer surface area-to-frontal area, and properties of the base polymer.

Example 9

Porometry

Capillary flow porometry, also known as porometry, is a technique based on the displacement of a wetting liquid from the sample pores by applying a gas at increasing pressure. This can be measured in the normal flow direction perpendicular to a membrane surface of unbacked membranes. A commercially available Capillary Flow Porometer (Model CFP-1200AEX, Porous Materials, Inc. Ithaca, NY), 25 mm disks of membrane, and the fluid Galwick with a surface tension of 15.9 dynes/cm were used to measure the flow rate versus pressure curve to get mean and max flow pore diameters. FIGS. 38.1 and 38.2 show plots of pore size distribution against average diameter for air-cast nitrocellulose and an electrospun non-woven fiber mat. Both the air-cast nitrocellulose and electrospun non-woven fiber mats have CFT of 135-180 seconds and mean flow and max flow pore diameters of about 3 and 3.6 microns, respectively. FIG. 39 shows the plot of CFT against MFP measured by porometry with the positive error bar extending to the max flow pore diameter. As such, two different structure membranes with similar CFTs have similar capillary flow porometry profiles.

FIG. 40 is a plot of the relationship of CFT to average fiber diameter for the same electrospun non-woven fiber mat samples in FIG. 39. FIG. 41 is a plot showing the relationship of MFP diameter to average fiber diameter for the electrospun fiber mats with CFTs of about 135-160 seconds.

Example 10

Delamination, Brittleness, and Wet-Dry Shrinkage

Air-cast nitrocellulose membrane can inherently be brittle and delaminate from the film substrate on which it is cast. Therefore, membrane is tested for delamination and brittleness before Quality control release. Delamination is tested by using 25×2.5 cm membrane test strips and folding and rolling between fingers over in the 25-cm direction to observe if the membrane peels off the substrate. Brittleness is tested by folding 45 degrees along the long axis and checking if cracks are observed. FIG. 42 is an image of 4 test strips tested for delamination and brittleness. From left-to-right the samples show that an air-cast nitrocellulose membrane (Hi-Flow™ Plus 135) and electrospun non-woven fiber mat membrane collected on a corona treated side of LDPE film (delamination, brittleness, and as spun) all pass the delamination and brittleness testing. FIGS. 43.1 and 43.2 show images of delamination and shrinkage testing of electrospun fiber mats with average fiber diameters of about 700 nm on LDPE film post IPA/water wetting, surfactant treatment, and air drying. FIG. 43.1 shows that duplicate electrospun membranes with average fiber diameters of about 700 nm spun on the corona treated side of LDPE do not delaminate or detectably shrink post IPA/water wetting, surfactant treatment, and air drying. FIG. 43.2 shows in triplicate that rectangular cut samples of the electrospun membrane on the non-corona treated side of LDPE film to allow for delamination only have minimal shrinkage post IPA/water wetting, surfactant treatment, and air drying. These experiments show that, unlike air-cast nitrocellulose membranes, the electrospun fibers provided herein with average fiber diameters of about 700 nm adhere well to corona treated LDPE, have minimal wet-dry shrinkage, and have no brittleness.

Example 11

Adhesion

Alternative methods were evaluated for adhesion of the electrospun non-woven fiber mats to a non-porous substrate because of the risks associated with adhesion. Electrospinning directly onto a film with an adhesive layer was investigated as a potential one-step option to get good adhesion onto a smooth non-porous film. To demonstrate the feasibility of this option, electrospun fibers were directly spun onto a 25-micron conductive polyimide film onto the side with a pressure sensitive acrylic adhesive and the side without adhesive (Kapton® XC from DuPont USA). FIG. 44.1 is an SEM image cross-section showing the electrospun fibers are well-bonded to the acrylic adhesive layer on the Kapton® film. FIGS. 45.1 and 45.2 show images of how the fiber mat remains well bonded to the acrylic adhesive side post IPA/water wetting, surfactant treatment, and air drying while the fiber mat delaminates from the non-adhesive side. This provides a novel demonstration of electrospinning onto a non-porous film substrate with an adhesive for bonding. This technology can be used with alternative adhesive chemistries, custom film adhesive combinations, and the use of the commercially available acrylic adhesive GL-187® from Lohmann Corporation (Orange, VA) which is FDA approved, universally used, and well accepted in the lateral flow diagnostics industry. FIGS. 44.2 and 44.3 are an image and SEM cross-section image of an electrospun non-woven fiber mat spun directly onto GL-187® adhesive from Lohmann Corporation (Orange, VA) that was coated onto Permastat LDPE PE700AS film (#7b in Table 5). Customized adhesive thicknesses can also be used with film and fiber mat thicknesses to meet the target thicknesses of 185 and 235 microns most commonly targeted in the lateral flow diagnostic assays. Alternative methods of adhesion of the fiber mats onto films also include corona or plasma treatment, surface etching or roughening, and even binary layer film combinations where spinning can be done onto a thin layer of polymer that is soluble in the electrospinning solvent to allow for vapor solvent bonding of fibers to the substrate. Alternatively, the electrospin fibers can be spun onto a film without adhesion and the fibers can be laminated or transferred to a film with an adhesive with the upper air surface inverted and the film side up. FIGS. 44.4 and 44.5 are an image and SEM cross-section image of an electrospun non-woven fiber mat that was spun onto and transferred from the non-adhesive and non-corona treated side of the Permastat LDPE PE700AS film (#7b in Table 5) onto GL-187® adhesive from Lohmann Corporation (Orange, VA) that was coated onto Permastat LDPE PE700AS film (#7b in Table 5).

Example 12

Electrospun Fiber Characterization by SEM

Electrospun fibers were imaged and average fiber diameters measured via SEM. Samples were prepared by coating with gold or iridium using a Cressington 208HR resolution sputter coater. Cross-sections were prepared by cryo-fracture by immersing in liquid nitrogen and fracture before sputter coating. Typical magnifications were 500-10000× using a FEI Quanta 200F field emission scanning electron microscope at 3/5 kV. Lower magnification samples were imaged using a JEOL JCM-6000PLUS Benchtop SEM. Average fiber diameters and standard deviations were calculated with 10 random fiber measurements.

Example 13

Lateral Flow Diagnostics Applications (references Hi-Flow™ Plus Brochure and Document TB500EN00EM)

The novel formulations and electrospinning process produce electrospun fiber mat membranes with average fiber diameters of greater than 500 nm, MFP ratings of more than 2 microns, and high porosity of higher than 85%. The electrospun membranes have comparable properties and several advantages over the commercially available air-cast nitrocellulose membranes which are currently used in lateral flow diagnostic assays. The electrospun non-woven fiber mat membranes have similar or improved consistency for CFT, detector bead mobility, and protein striping quality. Advantages of the electrospun fiber mat membranes provided herein include highly reproducible fiber diameters with resulting narrow MFP, higher porosity, higher surface area, higher and tunable protein binding, less background auto-fluorescence, potential for lower analyte detection limits, and more accurate assay quantification. Other beneficial improvements of the electrospun fiber mat membranes provided herein are the use of stable synthetic polymers to give better manufacturing reproducibility, end-user application consistency, longer shelf-life, non-hazardous properties (compared to nitrocellulose), and lower capital investment in manufacturing equipment with smaller square foot requirements than air-casting equipment.

Example 14

Surfactant Treatment and CFT

Because air-cast nitrocellulose is naturally hydrophobic, it needs to be treated with surfactant to allow for wetting and aqueous capillary flow. Surfactants are commonly used to pre-treat nitrocellulose membranes for lateral flow diagnostic applications. Typical treatment involves applying a dilute solution of aqueous surfactant at the end of the casting process, followed by drying to leave a coating of surfactant on the membrane for spontaneous aqueous rewetting during use. Treatment of PMMA:PVDF fiber mats can be done by 2 min wetting in 70:30 IPA:water, 10 minute agitated soak in a surfactant solution, and overnight air drying at ambient temperature and relative humidity.

Example 15

CFT

CFT is an industry-standarized test where a test strip of 1×4 cm is set into a well of 150 µL of water and the CFT is measured as the time it takes for a uniform liquid front to travel up the full 4 cm length. The test water should be 21±1° C. and the room relative humidity should be 50±5% (MilliporeSigma test method 000764TM). Typically, CFTs useful in lateral flow diagnosticassays are 75-180 seconds. Generally, faster CFTs provide lower signal intensity while slower CFTs provide more intense signals, all other conditions being equal.

Example 16

Latex Detector Bead Mobility

Functional lateral flow diagnostic assays use colored detector particles to produce the signal lines. One class of particles used is latex beads of 400 nm diameter. Therefore, membranes used in lateral flow assays must permit these beads to pass freely through the pore structure without any separation of the bead front from the liquid front. Hi-Flow™ Plus air-cast nitrocellulose membranes pass such test using a test solution of 0.05% of carboxylate modified 400-nm latex beads (Duke Scientific, DB1040C), 0.1% Tween surfactant, in 1 mg/mL BSA in PBS buffer. The test is performed on a 1×4 cm test membrane using 25 µL of solution. The liquid is allowed to flow to the top, only passing if there is no visible separation of a clear liquid flow front and a colored line of detector beads. Gold nanoparticles of about 40 nm can also be used; however, this test does not represent a quality control test because, if membranes can pass 400-nm latex beads, the membranes would pass 40-nm gold particles. FIG. 46 is an image of a custom test stand used to measure CFT and latex detector bead mobility. FIGS. 47.1 and 47.2 show images of membranes at the end of the latex detector bead mobility test. FIG. 47.1 shows duplicate electrospun non-woven fiber mat membranes with an average fiber diameter of 632±212 nm and about 200 second CFT that pass the bead mobility test, along with a passing Hi-Flow™ Plus 135 nitrocellulose control membrane. FIG. 47.2 is an image of duplicate electrospun membranes with an average fiber diameter of 432±95 nm and about 300-second CFT that fail the bead mobility test, with obvious visual failure of the beads to travel the full 4 cm. FIGS. 48.1 and 48.2 are SEM cross-section images of the bead passing electrospun fiber mat and Hi-Flow™ Plus 135 that show the 400 nm beads present in the cross-section. This demonstrates there is a minimum average fiber diameter and corresponding MFP and porosity required to pass the 400-nm latex beads.

Example 17

CFT Versus Average Fiber Diameter with Latex Bead Mobility Observations

FIG. 49 is a plot of several electrospun non-woven fiber mats at similar net mat thicknesses and their corresponding CFTs against average fiber diameters. The data demonstrate that the larger the average fiber diameter the higher the MFP, which produces a faster CFT or capillary flow. The same membranes were tested for latex bead mobility (FIGS. 47.1 and 47.2), and a minimum average fiber diameter and corresponding MFP or resulting porosity needed to freely pass the 400-nm latex detector beads was observed. FIG. 50 shows that CFT is a function of average fiber diameter. In this example, a solution of 17% w/v PMMA5 (BS572): PVDF6 (Kynar® 761) at ratio of 75:25 in DMAC was electrospun on a moving web of LDPE and the variable average fiber diameters resulted from uncontrolled dew point (higher dew point produced higher fiber diameters).

FIG. 51 shows a plot of CFT against average net fiber mat thickness for electrospun non-woven fiber mats all having about 700 nm average fiber diameters. All samples produced similar fiber diameters because they were electrospun under very close dew points. Mat thickness was controlled by spin time, line speed, and voltage. CFTs were measured at room temperature and relative humidity of 30-40%. The slower CFTs observed on thinner mats was likely an effect of increased evaporation rates due to the high surface area and porosity.

Example 18

CFT vs Mat Thickness and Relative Humidity

Because CFT depends on the relative humidity, CFTs of different fiber mat thicknesses having the same average fiber diameters of about 700 nm were measured under equilibrated and carefully controlled relative humidity in a controlled humidity box. Samples were equilibrated overnight at 30° C. and relative humidities of 10, 50, 75, and 90%. FIG. 52.1 shows a plot of CFT against relative humidity for membranes of different average net thicknesses including the Hi-Flow™ Plus 135's net thickness of 135 µm. Thinner mats produced slower CFTs at low relative humidities because of the competition of evaporation with capillary flow. The data show CFT sensitivity to humidity for the 135-µm thick Hi-Flow™ Plus 135 membrane. CFT release specifications and tolerances are based on testing at 21±1° C. and relative humidity of 50±5%. FIG. 52.2 shows a plot of CFT against membrane mat thickness for different relative humidities, showing the sensitivity of CFT to mat thickness and humidity. Higher thicknesses closer to Hi-Flow™ Plus 135's net thickness of 135 µm were less sensitive to the relative humidity at which the CFT was measured (FIG. 52.1).

Example 19

Porosity, Surface Area, and Surface Area Ratio

Additional properties that contribute to the application of membranes for lateral flow diagnostics includes porosity, surface area, and surface area ratio. Porosity % is calculated by the following equation:

Porosity=[1−(basis weight/(mat thickness×polymer density))], where, units of basis weight, polymer density, and mat thickness are (g/m²), (g/m³), and m, respectively.

Internal surface area in m²/gram is determined as BET surface area using Krypton gas by Micromeritics (Norcross, GA). Surface area ratio is the ratio of internal surface area to frontal surface area, a metric used for assay development to optimize reagent concentrations and assay conditions. Hi-Flow™ Plus membranes typically have surface area ratios of about 100. Surface area ratio is calculated as follows:

Surface area ratio=BET surface area (m²/g)×basis weight (g/m²)

Table 8 details a selection of electrospun non-woven fiber mat membranes and Hi-Flow™ Plus 135 membrane including data for average fiber diameter, average net thickness, basis weight, % porosity, BET surface area (SA), surface area ratio, protein binding, and CFT. Protein binding is calculated in µg/cm³ by normalizing protein binding by unit area µg/cm² with membrane thickness. The electrospun samples are relatively close to Hi-Flow™ Plus 135, although skewed because of being thinner. The fibers have lower mat thickness/basis weight/area ratios and protein binding but have a higher percent porosity and BET SA. FIG. 53 is a plot of mat thickness against basis weight for electrospun fibers and Hi-Flow™ Plus 135 membrane. The basis weight projects to be lower for fibers at similar thicknesses because of the higher porosity and different polymer densities. However, functionality in Lateral Flow Assays is dependent on understanding the membrane's properties. Fibers at similar thickness to air-cast nitrocellulose have lower basis weights, higher porosity, higher surface area, higher protein binding.

TABLE 8

Average fiber diameter, average net mat thickness, basis weight, % porosity, BET surface area, surface area ratio, protein binding, and CFT information for a selection of electrospun non-woven fiber mat membranes and Hi-Flow ™ Plus 135 membrane.

| sample ID | Polymer (ratio) | Surfactant 1 (%) | Fiber diameter (nm) | Avg. mat thickness (µm) | STDEV | Basis weight (g/m²) | STDEV | Porosity (%) |
|---|---|---|---|---|---|---|---|---|
| 072616-1 | PMMA:PVDF 75:25 | 0.1 | 630 ± 150 | 41 | 5 | 7.8 | 1.5 | 84.5 |
| 072716-1 | PMMA:PVDF 85:15 | 0.1 | 725 ± 200 | 30 | 4 | 6.5 | 3.7 | 84.2 |
| 090616-1 | PMMA:PVDF 75:25 | 0.1 | 860 ± 205 | 70 | 11 | 11.5 | 2.0 | 87.7 |
| 091316-2 | PMMA:PVDF 75:25 | 0.02 | 796 ± 190 | 63 | 7 | 10.7 | 1.6 | 87.6 |
|  |  | 0.1 |  | 63 | 7 | 10.7 | 1.6 | 87.6 |
| Hiflow Plus 135 | Nitrocellulose | 0.0625 | NA | 135 | 0 | 37.5 | 0.0 | 84.0 |

| sample ID | BET SA (m²/g) | SA ratio (m2/m²) | protein binding (µg/cm²) | STDEV | CFTAVE (sec) | STDEV | protein binding (µg/cm³) |
|---|---|---|---|---|---|---|---|
| 072616-1 | 1.8 | 14.3 | 95 | 10.6 | 241 | 19 | 23049 |
| 072716-1 | 6.0 | 38.7 | 70 | 4.2 | 217 | 5 | 23233 |
| 090616-1 | 3.1 | 36.0 | 122 | 7.0 | 161 | 7 | 17429 |
| 091316-2 | 2.3 | 24.6 | 121 | 6.0 | 185 | 2 | 19206 |
|  | 3.5 | 37.5 | 98 | 15.0 | 136 | 1 | 15556 |
| Hiflow Plus 135 | 2.4 | 89.2 | 159 | 20.3 | 132 | 1 | 11756 |

Example 20

Effect of Surfactant Treatment Concentration and Type on CFT

The effect of surfactant concentration in the hydrophilic treatment of the electrospun fiber mats on CFT was investigated using two types of surfactant, surfactant 1 and surfactant 2. Electrospun fiber mats of varying thicknesses and average fiber diameter of about 700 nm (composed of PMMA5 (BS572):PVDF6 (Kynar® 761) at ratio of 75:25) were treated with a range of 0.02-0.1% w/w surfactant 1 or surfactant 2 in water. CFT was measured for all samples at room temperature and constant relative humidity. FIG. 54.1 is a plot of the CFTs against surfactant 1 treatment concentration for fiber mats with varying thickness. FIG. 54.2 shows a similar plot of CFT after treatment with surfactant 2 surfactant. Both experiments demonstrate that CFT is a function of the surfactant used to hydrophilize the membrane and that CFT can slightly depend on the surfactant concentration used (higher % leading to lower CFT). FIGS. 54.1 and 54.2 also show that thicker mats have lower CFTs because of the effect of evaporation on the thinner mats causing higher CFTs. FIG. 55 is a plot of CFT against thickness for fiber mats treated with 0.1% surfactant 1 and surfactant 2. As such, surfactant 2 yields lower CFTs and again the CFT on thinner mats is higher because of the competition of evaporation with capillary flow.

Example 21

Protein Binding

Protein binding is an important characteristic of a membrane used in lateral flow diagnostic assays. Quantification of a membrane's protein binding is measured and reported in $\mu g/cm^2$. For reference Hi-Flow™ Plus 135 nitrocellulose typically has a value of about 150 $\mu g/cm^2$. The protein binding of a membrane is determined using goat IgG at a concentration of 1 mg/mL spiked with $^{125}$I-(goat IgG) at a concentration of 0.1 µCi/mL. Membrane disks were wetted out and incubated with the radiolabeled goat IgG in PBS buffer for 2 hours, rinsed, and assayed for bound radioactivity and converted to micrograms of IgG/cm² of membrane. FIGS. 56.1 and 56.2 show that IgG protein binding in $\mu g/cm^2$ depends on mat thickness and the surfactant treatment. For both surfactants protein binding decreases with higher wt % surfactant treatment. FIG. 57 plots IgG binding against the average net fiber mat thicknesses of about 700 nm PMMA:PVDF (75:25) fibers treated with the various wt % of Surfactant 1 and 2 shown in FIGS. 56.1 and 56.2 along with the Hi-Flow™ Plus 135 control. This plot suggests at fiber diameter of about 700 nm and PMMA:PVDF ratio of 75:25, at similar mat thicknesses, the electrospun mats would have similar protein binding as the Hi-Flow™ Plus 135 control. Fibers treated with Surfactant 2 have slightly higher average protein binding (FIG. 57). Also, PVDF likely has a higher protein binding potential than PMMA.

Example 22

Protein Striping

Protein striping line quality is another important attribute required of membranes used in lateral flow diagnostic assays because line quality reflects the resolution of test lines in functional assays. Membrane samples were striped using a Matrix™ 1600 Reagent Dispensing Module (Kinematic Automation, CA, USA) with 2 mg/mL mouse IgG in PBS buffer at different dispensing rates of 4/cm. After drying the mats, they were stained with Ponceau S and rinsed with 1% acetic acid. Protein lines are then qualitatively assessed against Hi-Flow™ Plus 135 controls for line width, consistency, quality, and any artifacts that would negatively impact the function of a lateral flow diagnostic assay. Protein line striping and detection lines on assays can be optimized by changing protein concentration and the dispensing rate. Table 9.1 and FIG. 58.1 summarize a comparison of protein striping quality of electrospun non-woven fiber mat samples against a Hi-Flow™ Plus 135 control. With no significant optimization besides changing line speed, the electrospun fiber mat exhibited line qualities similar to the commercial Hi-Flow™ Plus 135 control (FIG. 58.1). Protein striping can be optimized with dispense rate, line speed, protein concentration, and a thorough evaluation of the thickness, basis weight, surface area, and protein binding capacity of the porous material. Table 9.2 and FIG. 58.2 summarize protein striping quality as a function of protein (IgG) solution conditions detailed in Table 9.2 for pH and conductivity. FIG. 58.2 shows from left to right a Hi-Flow™ Plus 135 control and replicate samples of electrospun non-woven fiber mat membranes PMMA:PVDF (70:30) treated with 0.07 and 0.09% surfactant 2 (Example 20). The observed Protein striping line quality was from best to poorest was solutions 3>4>2>1. Table 9.3 and FIG. 58.3 summarize protein striping quality as a function of protein (IgG) solution conditions detailed in Table 9.3 for pH and conductivity. FIG. 58.3 shows from left to right duplicate Hi-Flow™ Plus 135 controls and replicate samples of electrospun non-woven fiber mat membranes PMMA:PVDF (70:30) treated with 0.07 and 0.09% surfactant 2 (Example 20). The observed Protein striping line quality was from best to poorest was pH 5=6>7.2>8>9. Tables 9.2 and 9.3 and FIGS. 58.2 and 58.3 indicate the best protein striping quality is achieved through solution conditions favoring a cation exchange binding mechanism.

TABLE 9.1

Summary of electrospun non-woven fiber mat membranes, Hi-Flow ™ 135 control, and conditions screened for Protein Striping quality in FIG. 58.1.

| Sample ID | PMMA:PVDF BS572:761 | mat thickness (µm) | fiber diameter (nm) | CFT (sec) | Protein striping pump (µL/cm) | Protein line quality |
|---|---|---|---|---|---|---|
| 072016-2 | 75:25 | 89 ± 10 | 697 ± 183 | 173 ± 6 | 1 | good |
| 072016-6 | 75:25 | 41 ± 3 | 612 ± 162 | 220 ± 12 | 0.5 | good |
| Hi-flow 135 | NA | 135 | NA | 135 | 1 | good |

TABLE 9.2

Summary of protein (IgG) solution conditions screened
for Protein Striping quality in FIG. 58.2.

| Solution | IgG conc. (mg/mL) | Buffer | Salt | pH | Conductivity (mS/cm) |
|---|---|---|---|---|---|
| 1 | 2 | PBS std | 1M NaCl | 8 | 78.1 |
| 2 | 2 | PBS std | — | 8 | 16.12 |
| 3 | 2 | 20 mM Sodium Acetate | — | 5.5 | 3.72 |
| 4 | 2 | PBS std | — | 7.4 | 16.11 |

TABLE 9.3

Summary of protein (IgG) solution conditions screened
for Protein Striping quality in FIG. 58.3.

| Solution | IgG conc. (mg/mL) | Buffer (20 mM) | pH | Conductivity (mS/cm) |
|---|---|---|---|---|
| 5 | 2 | Sodium Acetate | 5 | 1.8 |
| 6 | 2 | Sodium Phosphate | 6 | 3.5 |
| 7 | 2 | Sodium Phosphate | 7.2 | 3.4 |
| 8 | 2 | Sodium Phosphate | 8 | 3.3 |
| 9 | 2 | Trizma ® | 9 | 1.9 |

Example 23

Membrane Background Fluorescence

Because some lateral flow diagnostic assays require detection and/or quantification of fluorescently labelled detector beads, the background fluorescence of the membrane needs to be well. Solid state fluorescence spectroscopy was performed on electrospun fiber membranes with PMMA:PVDF ratios of 75:25 and 50:50 and the Hi-Flow™ Plus 135 nitrocellulose control, which is known to have background fluorescence. The fluorescence spectroscopy was performed by photon counting intensity using a ChronosFD Fluorescence Lifetime Spectrometer (ISS), Vinci2, and spectra processing in Mathematica software. Excitation wavelengths of 300-610 nm and emission wavelengths of 320-630 nm were scanned with PMTs in 10 nm steps. FIG. 59 is the fluorescence spectrum of intensity against excitation and emission wavelengths for the Hi-Flow™ Plus 135 nitrocellulose control membrane that shows fluorescence in the emission region of about 350-500 nm. The large diagonal ridge is from Raleigh scattering. FIGS. 60.1 and 60.2 show the fluorescence spectrum intensity against excitation and emission wavelengths for the PMMA:PVDF ratios of 75:25 and 50:50 minus the Hi-Flow™ Plus 135 nitrocellulose control membrane spectrum. This demonstrates that the electrospun non-woven fibers of PMMA:PVDF have less auto-fluorescence than nitrocellulose membranes.

Example 24

Fluorescence Microscopy for Fluorescent Bead Detection

Fluorescent microspheres and fluorescence microscopy were used to visualize the differences in the Hi-Flow™ Plus 135 nitrocellulose control membrane and electrospun PMMA:PVDF (75:25) membranes in terms of fluorescent bead visibility and signal intensity through the surface porosity of the two different structures and differences in the auto-fluorescence. The experiment was performed using a modification of the aforementioned latex bead mobility test (Example 16). The fluorescent bead test solution was 0.05% fluorescent carboxylated polymer microspheres, 0.4-micron diameter, P(S/V—COOH), Ex max 480 nm, Em. Max 520 nm (FC02F Bangs Laboratories, Fishers, IN), 0.1% Tween surfactant, in 1 mg/mL BSA in PBS buffer. The solution was allowed to flow up the 1×4 cm membrane strips and was air dried before visualization under the fluorescent microscope. A Nikon Eclipse TE2000-U microscope with NIS Elements Imaging software and Ti-LAPP Modular Illumination System in Brightfield and FITC mode were used for analysis (Nikon Instruments Inc. USA). FIG. 61 is a collection of sample images comparing the Hi-Flow™ Plus 135 nitrocellulose control membrane and electrospun PMMA:PVDF (75:25) membranes with and without fluorescent beads at 200× magnification, FITC mode, and constant laser excitation intensity. The figure shows the background fluorescence of the Hi-Flow™ Plus 135 nitrocellulose control membrane, while the electrospun PMMA:PVDF (75:25) membrane has no visual fluorescence. The samples with beads show higher visual emission fluorescence intensity through the non-woven fiber structure of the electrospun PMMA:PVDF (75:25) membrane when compared to the air-cast Hi-Flow™ Plus 135 nitrocellulose control membrane. The higher surface porosity of the electrospun non-woven fiber mat potentially allows for lower detection limits in terms of fluorescence detection during functional assays. Also, no auto-fluorescence of the base electrospun PMMA:PVDF (75:25) membrane makes detection and quantification easier compared to detection and quantification with air-cast Hi-Flow™ Plus 135 nitrocellulose membranes.

Example 25

Advantages of the Electrospun Nanofibers and Membrane Mats

FIG. 6 indicates that four parameters (PMMA:PVDF ratio, % solids, dew point, and solvent composition) control fiber diameter and morphology. Also, four parameters (PMMA:PVDF ratio, electrospinning parameters, dew point, and film substrate) contribute to non-woven fiber mat productivity and uniformity. Additionally, four parameters (fiber diameter/effective pore size, PMMA:PVDF ratio, surfactant treatment, and mat thickness and uniformity) contribute to the properties relevant for use in lateral flow diagnostic applications, namely, CFT, detector bead mobility, protein binding, protein striping, and functional assay performance. The electrospinning parameters that can be controlled during electrospinning nanofibers include voltage, air flow, electrode distance, substrate line speed, carriage speed, dispensing orifice, and spinning electrode wire speed. Table 10 summarizes the properties of the Hi-Flow™ Plus135 air-cast nitrocellulose membrane and typical electrospun PMMA:PVDF membrane.

TABLE 10

Comparison of the properties of Hi-Flow™ Plus 135 nitrocellulose control membrane and an electrospun PMMA:PVDF membrane.

| Parameter | Hi-Flow™ Plus 135 air cast nitrocellulose | Electrospun membrane |
| --- | --- | --- |
| Polymer | Air-cast nitrocellulose | 75:25 to 50:50 (PMMA:PVDF) |
| Fiber diameter (nm) | NA | >500 nm |
| Capillary flow time (sec/4 cm) | 135 ± 34 | 125-200 |
| Thickness (μm) | 135 ± 15 | >80 |
| pass Porosity/Bead mobility | Gold & Latex beads 40, 400 nm | Gold & Latex beads 40, 400 nm |
| Protein Binding (μg/cm$^2$) | typically 100-150 | >90 |
| Protein Striping | Straight/even/unbroken line | Straight/even/unbroken line |
| Sensitivity in Hep B assay (with gold NPs) | Meets | Meets |
| Sensitivity in hCG assay (with latex beads) | Meets | Meets |
| Mechanics (Brittle/Separation) | Some brittleness issues | Non-brittle |
| Visuals (color/surface) | White/smooth | White/smooth |
| Hazard | Hazardous | Non-hazardous |
| Wetting agent | Surfactant | Surfactant |
| Chemical Stability | Degrades | Stable |

Example 26

Additional Examples of Electrospun

14% of PMMA in DMF was prepared by dissolving 7 g of PMMA in 43 g of DMF and stirred for 30 h at room temperature. The final solution was collected in a 10 mL plastic syringe with an 18G (gauge) needle attached and used for electrospinning (NANON-01A electrospinning machine, Japan). The feed rate of the polymer solution was varied from 1 to 5 mL/h, the applied voltage was varied from 10 to 30 kV and the tip-to-collector (support for the membrane) distance was varied from 10 cm to 15 cm. PMMA electrospun membranes were obtained with a feed rate of 5 mL/h, a voltage of 18 kV and needle to collector distance of 15 cm. The membranes with a thickness in the range of 20-120 μm were spun on Melinex polyester backing, were dried at room temperature to remove solvent, and heat-treated at 150° C. to get uniform membranes. Similarly, electrospun membranes were prepared with PVDF, PVB, PA and PES. Table 11 shows the composition of the various membranes, electrospinning conditions and CFTs.

TABLE 11

Polymer electrospun membranes

| Polymer Composition | ES Conditions | Backing film | Membrane Thickness (μm) | CFT (sec) | Comments |
| --- | --- | --- | --- | --- | --- |
| PMMA 14 wt % | DMF, 18 kV, 15 cm, 3 mL/h, 23° C./38% | Melinex | 60 μm | 124 | Microfibers & 60 μm shows good adhesion to Melinex |
| PVB 60H 12 wt % | EtOH, 18 kV, 15 cm, 5 mL/h, 24° C./39% | Aluminum foil | 97 μm | 157 | Microfibers & Membrane prepared using Al foil |
| PVB 60T 12 wt % | EtOH, 18 kV, 15 cm, 5 mL/h, 24° C./39% | Aluminum foil | 100 μm | 430 | Microfibers & Membrane prepared using Al foil, free standing membranes |
| PVB 75H 6.7 wt % | EtOH, 18 kV, 15 cm, 5 mL/h, 24° C./39% | Aluminum foil | 53 μm | 153 | Microfibers & Membrane prepared using Al foil, free standing membranes |
| PVB 60HH 12 wt % | EtOH, 18 kV, 15 cm, 5 mL/h, 24° C./39% | Aluminum foil | 101 μm | 103 | Microfibers & Membrane prepared using Al foil, free standing membranes |
| PVDF 15 wt % | DMAc/Acetone/THF (1:1:0.5) 30 kV, 15 cm, 1 mL/h, 24° C./40% | Melinex | 119 μm | 162 | Nanofibers & Good adhesion to Melinex |

TABLE 11-continued

Polymer electrospun membranes

| Polymer Composition | ES Conditions | Backing film | Membrane Thickness (μm) | CFT (sec) | Comments |
|---|---|---|---|---|---|
| PES 32 wt % | DMAC, 30 kV, 15 cm, 3 mL/h, 23° C./38% | Melinex | 120 μm | 123 | Nanofibers & Poor adhesion to Melinex backing |
| PA B24 22 wt % | AcOH/HCO$_2$H (2:1), 80° C. 5 h then RT 30 kV, 15 cm, 1 mL/h, 23° C./38% | Melinex | 87 μm | 219 | Nanofibers & Poor adhesion to Melinex backing |
| PA B27 22 wt % | AcOH/HCO$_2$H (2:1), 80° C. 5 h then RT 30 kV, 15 cm, 1 mL/h, 23° C./38% | Melinex | 115 μm | 138 | Nanofibers & Poor adhesion to Melinex backing |
| PA B40 20 wt % | AcOH/HCO$_2$H (2:1), 80° C. 5 h then RT 30 kV, 15 cm, 1 mL/h, 23° C./38% | Melinex | 120 μm | 187 | Nanofibers & Poor adhesion to Melinex backing |
| PVP 12 wt % | EtOH, 30 kV, 15 cm, 1 mL/h, 23° C./38% | Melinex | 100 μm | — | Nanofibers & membrane dissolved in surfactant 1 solution |
| Nitrocellulose (NC) 7 wt % | Acetone, 20 kV, 15 cm, 5 mL/h, 23° C./36% | Melinex | 68 μm | — | Nanofibers & Poor adhesion to Melinex backing |

Electrospun membranes with good adhesion to Melinex backing were obtained by varying the solution parameters and electrospinning conditions. FIG. 62 shows the dimensions of the electrospun membranes having various thicknesses produced using PMMA.

The fiber diameters and surface morphologies of electrospun membranes were characterized by a Zeiss Supra Variable Pressure Field Emission Scanning Electron microscope. The fiber diameters were in the range of 200 nm to 2.7 μm, and the surface profile of the membranes are shown in FIG. 63. Membranes have good porosity and pore size, which is more suitable for flow rates and allow Gold nanoparticle and latex bead mobility. The membranes also have adequate protein binding efficiency.

Example 27

Testing of Electrospun Membranes

Protein binding is essential to the function of membranes in lateral flow applications. The membrane should adsorb the required quantity of protein to permit visible reading of the test results. Protein stripping was carried out with the electrospun membranes. Membrane samples were cut (5 cm×15 cm) and pre-wet in ethanol for 1 min and immediately treated with 0.1 wt % surfactant 1 for 30 min and dried. The protein solution dispensed at a rate of 0.5 μl/cm. FIG. 64 shows the results of protein stripping of the electrospun membranes, which show that proteins can be applied to and bind to the electrospun membranes produced by the methods described herein.

The most commonly used detector reagents in lateral flow systems are colloidal gold and latex particles. These particles are generally coupled with a variety of detector reagents and applied on lateral flow membranes. The detector reagents permit the user to visualize the results. Testing the mobility of the gold and latex particles on electrospun PMMA and PVDF membranes was carried out. FIGS. 65 and 66 respectively show the flow fronts of both the gold and latex particles on PMMA and PVDF electrospun membranes. These figures show that the particles flow through the electrospun membranes uniformly and without any flow front separation.

The PMMA electrospun membranes of FIGS. 65 and 66 were examined under SEM to determine the flow pattern of the latex and gold nanoparticles. FIG. 67 shows the SEM images of the PMMA electrospun membranes after the latex and gold particle mobility test. These particles flow along the sides of the fibers within the membrane structure through interconnected pores without any flow front separation.

Example 28

Electrospun Membranes Made Up of Polymer Blends

Electrospun membranes were prepared with various polymer blends. Table 12 shows the list of blended electrospun membranes, together with the conditions employed and the characteristics of the membranes produced.

To prepare 12.5% PMMA/PVDF (2:1 ratio) blended membranes, 5 g of PMMA and 2.5 g of PVDF were dissolved in 60 ml of DMAc/Acetone/THF solvent at room temperature. The electrospinning parameters were as follows: a feed rate of polymer solution was 5 ml/hr, an applied voltage of 20 kV and a collector distance of 15 cm. To prepare 12.5% PMMA/PVDF (1:2 ratio) blended membranes, similar conditions were used; however, the amount of PMMA and PVDF were reversed. The blended membranes were dried at room temperature to remove the residual solvent from the membranes.

TABLE 12

Blend electrospun membranes

| Polymer Composition | ES Conditions | Backing film | Membrane Thickness (μm) | CFT (sec) | Comments |
|---|---|---|---|---|---|
| PMMA/PVDF (2:1) 12.5 wt % | DMAC/Ac/THF (3:7:2), 20 kV, 15 cm, 5 mL/h, 23° C./36% | Melinex | 68 μm | 98 | Microfibers & Good adhesion to Melinex |
| PMMA/PVDF (1:2) 12 wt % | DMF, 18 kV, 15 cm, 5 ml/h, 24° C./30% | Melinex | 65 μm | 179 | Nanofibers & Good adhesion to Melinex |
| PMMA/PVB (0.2%) 14% | DMF, 18 kV, 15 cm, 5 mL/h, 24° C./30% | PHA treated Melinex | 110 μm | 0.7 cm after 10 min | Microfibers & Good adhesion to sticker paper |
| PMMA/PVB (1%)/Surfactant 1 (0.1%) 14 wt % | DMF 18 kV, 15 cm, 5 mL/h, 25° C./30% | Melinex | 64 μm | 307 | Microfibers & Lamination processed membrane |
| PMMA/PVB (0.5%)/Surfactant 1 (0.1%) 14% | DMF 18 kV, 15 cm, 5 mL/h, 25° C./30% | Melinex | 107 μm | 388 | Microfibers & Lamination processed membrane |
| PMMA/PVB (0.5%)/Surfactant 1 (0.1%) 14% | DMF 18 kV, 15 cm, 5 mL/h, 25° C./30% | Sticker paper | 44 μm | 1.8 cm (after 10 min) | Microfibers & Good adhesion to sticker paper |
| PES/PVP (1%) 32% | DMAC, 30 kV, 15 cm, 3 mL/h, 23° C./23% | Melinex | 100 μm | 198 | Nanofibers & Poor adhesion to Melinex backing |
| NC/PVB (0.5%)/Surfactant 1 (0.1%) 17% | EtOH/Acetone/BuOH/ Water (30:20:20:5%) 30 kV, 15 cm, 1 mL/h, 23° C./23% | Melinex | 20 μm | 1.4 cm (after 5 min) | Nanofibers & Poor adhesion to Melinex backing |
| NC/PVB (0.5%)/Surfactant 1 (0.1%) 17% | EtOH/Acetone/BuOH/ Water (30:20:20:5%) 30 kV, 15 cm, 1 mL/h, 23° C./23% | Melinex | 15 μm | 1.6 cm (after 5 min) | Nanofibers & Poor adhesion to Melinex backing |

FIG. 68 shows the protein striping results of the PMMA/PVDF (2:1 ratio) blended and PMMA/PVDF (1:2 ratio) blended membranes. These results show that proteins can be applied to the electrospun blended membranes and the proteins bind to the electrospun membranes.

The mobility of the gold and latex particles on electrospun PMMA and PVDF membranes was tested. FIG. 69 shows the flow fronts of both the gold and latex particles on PMMA/PVDF blended electrospun membranes. These images show that the particles are flowing through the blended electrospun membranes uniformly and without any flow front separation.

As such, methods for producing highly porous electrospun membranes from various polymers PMMA, PVDF, PA, PES and PVB, or combinations thereof are provided. The membranes in the electrospinning method are formed by high surface area micro/nanofibers and the pore size of the membrane can be controlled by changing the diameter of the fiber by blending suitable polymer with different ratios (e.g. PMMA alone μm fibers and PMMA/PVDF were nanofibers).

The production of lateral flow membranes by current air casting method is very slow due to the formation of membranes by phase inversion method, whereas the formation of membrane is instantaneous in the electrospinning methods provided herein. The membranes produced from various polymers and polymer blends using the methods provided herein were evaluated. Membranes provided herein are more sensitive and facilitate detection of lower levels of analytes compared to current lateral flow membranes. FIG. 70 illustrates a Hepatitis B assay where the membranes produced from various polymers and polymer blends were evaluated and the ES membranes are more sensitive than current lateral flow membranes.

Example 29

Functional Lateral Flow Assays Using Aforementioned Structures

Electrospun non-woven fiber mat membranes produced via the aforementioned examples (summarized in Example 25) using needle-less electrospinning were used in fully integrated Lateral Flow Assays and benchmarked against Air-cast nitrocellulose. Examples include a complete Hepatitis B surface antigen (HBsAg) lateral flow test and hCG (Human chorionic gonadotropin hormone) functionality testing to detect pregnancy described by MilliporeSigma Test Method documents 00081440™ and 00081293™.

FIG. 71.2 shows a standard passing test with a positive test line detection at 8 ng/mL in the Hepatitis B surface antigen (HBsAg) lateral flow test using an air-cast nitrocellulose membrane. FIG. 71.1 shows a similar passing HBsAg test using the Electrospun non-woven fiber mat membrane produced in the aforementioned examples, summarized in Example 25. The Electrospun non-woven fiber mat membrane was PMMA:PVDF (70:30) with an average fiber diameter for ~800 nm on LDPE PE700AS film treated with 0.08% surfactant 2.

FIG. 72.2 shows a passing test with positive test line detection at 25 mIU in the hCG (Human chorionic gonadotropin hormone) functionality test to detect pregnancy using an air-cast nitrocellulose membrane. FIG. 72.1 shows a similar passing test with the hCG (Human chorionic gonadotropin hormone) functionality test to detect pregnancy using the Electrospun non-woven fiber mat membrane produced in the aforementioned examples, summarized in Example 25. The Electrospun non-woven fiber mat membrane was PMMA:PVDF (70:30) with an average fiber diameter for ~800 nm on LDPE PE700AS film treated with 0.08% surfactant 2.

Example 30

Electroblowing Fibers

Fibers mats comprising polymer ratios between PMMA: PVDF of about 100:0 to 0:100, particularly, about: 10:90, 15:85, 20:80, 25:75, 30:70, 35:65, 40:60, 45:55, 50:50, 55:45, 60:40, 65:35, 70:30, 75:25, 80:20, 85:15, or 90:10, are made with average fiber diameters of 500-1000 nanometers, mean flow pore ratings of 1-5 microns, and mat thicknesses of 100 microns. In some embodiments, the fiber mats are made on porous substrates using electroblowing or electroblow spinning. The Fibers are spun from 10-20 w/w % solutions of PMMA:PVDF in solvents such as N,N-dimethylacetamide or N,N-dimethylformamide. The resulting polymer solutions are electroblown into fibers by pushing the polymer solutions through small nozzles alongside a flowing pressure field of gas where a high electrical field or potential is maintained from the exiting nozzle and collection area above which a moving porous non-woven collects the fibers. Conditions for electroblowing fibers of 500-1000 nm diameter from the polymer solution include solution flow of 1-10 mL/min from the nozzle into a gas pressure of >1 bar and an electric field of 1 to 100 kV DC. Mat thickness and uniformity can be controlled by adjusting temperature, relative humidity, dew point, non-woven substrate, and the chamber air flow. Electroblown non-woven fiber mats are subject to additional thermal drying, calendaring, and surfactant treatment and drying as post processes. Electroblown non-woven fiber mats are adhered to non-porous substrates using methods in Example 11. The resulting electroblown fiber non-woven mats have properties similar to the previous examples made by electrospinning summarized in Example 25. Similar properties include fiber diameter, mean flow pore size, mat thickness, capillary flow times, bead mobility, protein binding, and protein striping.

Certain aspects of the electroblowing process that can be used in the methods described herein are described in the U.S. Pat. No. 7,846,374, which is incorporated herein by reference in its entirety.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments described herein. Such equivalents are intended to be encompassed by the following claims.

What is claimed is:

1. A non-woven fiber membrane comprising nanofibers comprising a polymer blend of polymethylmethacrylate (PMMA) and poly(vinylidene difluoride) (PVDF), having an average fiber diameter from 200 nm to 1000 nm, wherein the membrane has a mean flow pore diameter of greater than about 1 micron to about 5 microns and a porosity of at least 80% and wherein said membrane is located in an assay developing region within a lateral flow diagnostic device.

2. The non-woven fiber membrane of claim 1, wherein the non-woven fiber membrane is generated by electrospinning.

3. The non-woven fiber membrane of claim 1, wherein the non-woven fiber membrane is generated by electroblowing.

4. The non-woven fiber membrane of claim 1, wherein the mean flow pore diameter is about or greater than about 2 microns.

5. The non-woven fiber membrane of claim 1, wherein the porosity is at least 85%.

6. The non-woven fiber membrane of claim 1, wherein the blend of PMMA and PVDF has the weight ratio of PMMA to PVDF from 1:99 to 99:1.

7. The non-woven fiber membrane of claim 6, wherein the ratio of PMMA to PVDF is 10:90, 15:85, 20:80, 25:75, 30:70, 35:65, 40:60, 45:55, 50:50, 55:45, 60:40, 65:35, 70:30, 75:25, 80:20, 85:15, or 90:10.

8. The non-woven fiber membrane of claim 1, comprising nanofibers having an average fiber diameter of about: 500 nm, 550 nm, 600 nm, 650 nm, 700 nm, 750 nm, 800 nm, 850 nm, 900 nm, 950 nm, or 1000 nm.

9. The non-woven fiber membrane of claim 1, having a mean flow pore diameter of at least: 1.0 microns, 1.5 microns, 1.75 microns, 2.0 microns, 2.25 microns, 2.5 microns, 2.75 microns, 3.0 microns, 3.5 microns, or 4.0 microns.

10. The non-woven fiber membrane of claim 1, said non-woven fiber membrane having pores, wherein at least 90% of pores have a diameter of between 2.75 microns and 3.25 microns.

11. The non-woven fiber membrane of claim 10, wherein at least 95% of pores have a diameter of between 2.75 microns and 3.25 microns.

12. The non-woven fiber membrane of claim 11, wherein at least 99% of pores have a diameter of between 2.75 microns and 3.25 microns.

13. The non-woven fiber membrane of claim 1, said non-woven fiber membrane having a thickness of from 25 to 250 microns.

14. The non-woven fiber membrane of claim 13, said non-woven fiber membrane having a thickness of from 100 to 175 microns.

15. The non-woven fiber membrane of claim 13, said non-woven fiber membrane having a thickness of about 150 microns.

16. The non-woven fiber membrane of claim 1, wherein said non-woven fiber membrane further comprises a surfactant.

17. The non-woven fiber membrane of claim 1, said non-woven fiber membrane having a capillary flow time of from 75 to 300 seconds.

18. The non-woven fiber membrane of claim 17, said non-woven fiber membrane having a capillary flow time of from 125 to 250 seconds.

19. The non-woven fiber membrane of claim 17, said non-woven fiber membrane having a capillary flow time of from 175 to 200 seconds.

20. The non-woven fiber membrane of claim 1, wherein the non-woven fiber membrane passes a detector bead mobility test for beads having a size of from 40 to 600 nm.

21. The non-woven fiber membrane of claim 1, wherein the non-woven fiber membrane passes a detector bead mobility test for beads having a size of from 200 to 440 nm.

22. The non-woven fiber membrane of claim 1, wherein the non-woven fiber membrane passes a detector bead mobility test for beads having a size of about 400 nm.

23. The non-woven fiber membrane of claim 1, the non-woven fiber membrane having a protein binding capacity of about 70 to 120 μg/cm² for a thickness of at least about 40 to 60 microns.

\* \* \* \* \*